(12) United States Patent
Von Keitz et al.

(10) Patent No.: US 9,744,515 B2
(45) Date of Patent: Aug. 29, 2017

(54) MULTIPHASE POROUS FLOW REACTORS AND METHODS OF USING SAME

(71) Applicant: BioCee, Inc., Minneapolis, MN (US)

(72) Inventors: Marc Gregor Von Keitz, Minneapolis, MN (US); Jimmy Lee Gosse, Burnsville, MN (US); Stefan Thust, Minneapolis, MN (US); Thomas Harwood, Minneapolis, MN (US)

(73) Assignee: Calysta, Inc., Menlo Park, CA (US)

( * ) Notice: Subject to any disclaimer, the term of this patent is extended or adjusted under 35 U.S.C. 154(b) by 359 days.

(21) Appl. No.: 14/357,767

(22) PCT Filed: Nov. 13, 2012

(86) PCT No.: PCT/US2012/064896
§ 371 (c)(1),
(2) Date: May 12, 2014

(87) PCT Pub. No.: WO2013/074551
PCT Pub. Date: May 23, 2013

(65) Prior Publication Data
US 2014/0323694 A1    Oct. 30, 2014

Related U.S. Application Data

(60) Provisional application No. 61/600,661, filed on Feb. 19, 2012, provisional application No. 61/559,277, filed on Nov. 14, 2011.

(51) Int. Cl.
*C12M 1/16* (2006.01)
*B01J 15/00* (2006.01)
(Continued)

(52) U.S. Cl.
CPC .......... *B01J 15/005* (2013.01); *B01J 16/005* (2013.01); *B01J 19/249* (2013.01); *C12M 29/04* (2013.01);
(Continued)

(58) Field of Classification Search
CPC .............................. C12M 25/06; C12M 25/18
See application file for complete search history.

(56) References Cited

U.S. PATENT DOCUMENTS

6,100,440 A    8/2000    Tumiatti et al.
6,309,550 B1   10/2001   Iversen et al.
(Continued)

FOREIGN PATENT DOCUMENTS

| NL | DE 202010001678 U1 * | 6/2010 | ........... A01K 1/0047 |
| WO | 2007032810 A2 | 3/2007 | |
| WO | 2011068576 A1 | 6/2011 | |

OTHER PUBLICATIONS

Mandal, Brazilian Journal of Chemical Engineering, vol. 27, No. 02, p. 253-264, 2010.*
(Continued)

*Primary Examiner* — William H Beisner
(74) *Attorney, Agent, or Firm* — Seed IP Law Group LLP

(57) ABSTRACT

PFRs for running multiphasic processes are disclosed. The PFRs are single or multi-chamber devices having at least three types of regions (a liquid-contacting region, a gas-contacting region and a Ssquid-coSection region), and a porous substrate providing fluid communication at least between the liquid-contacting and gas-contacting regions. Removal of liquid from the porous substrate, such as by collecting the liquid as it flows off the bottom of the porous substrate in the Siquid-coSSection region or such as by evaporation of the liquid from the porous substrate in the evaporation region supports a continuous flow process. Methods of using the PFRs are also disclosed, for example methods of using the PFRs as photobioreactors for cultivating photosynthetic microorganisms, for producing fermentable sugars, for producing ethanol, for fermenting synthesis gas and producing single cell protein from natural gas.

17 Claims, 27 Drawing Sheets

(51) Int. Cl.
   *B01J 16/00*     (2006.01)
   *B01J 19/24*     (2006.01)
   *C12M 1/00*      (2006.01)

(52) U.S. Cl.
   CPC .............. *B01J 2219/2453* (2013.01); *B01J 2219/2458* (2013.01); *B01J 2219/2462* (2013.01); *B01J 2219/2472* (2013.01); *B01J 2219/2479* (2013.01); *B01J 2219/2493* (2013.01); *B01J 2219/2497* (2013.01)

(56) References Cited

U.S. PATENT DOCUMENTS

2006/0008634 A1    1/2006   Pickrell
2007/0134790 A1*   6/2007   Gould .................. C12M 23/40
                                                      435/325

OTHER PUBLICATIONS

English language machine translation of DE 202010001678U1 (Jul. 15, 2010), pp. 1-12.*
Written Opinion for PCT/US2012/064896 dated Mar. 25, 2013 (4 pages).
M. Potts et al., "Effects of Water Stress on Cryptoendolithic Cyanobacteria from Hot Desert Rocks," 130 Arch. Microbiol. 267-271 (1981).

* cited by examiner

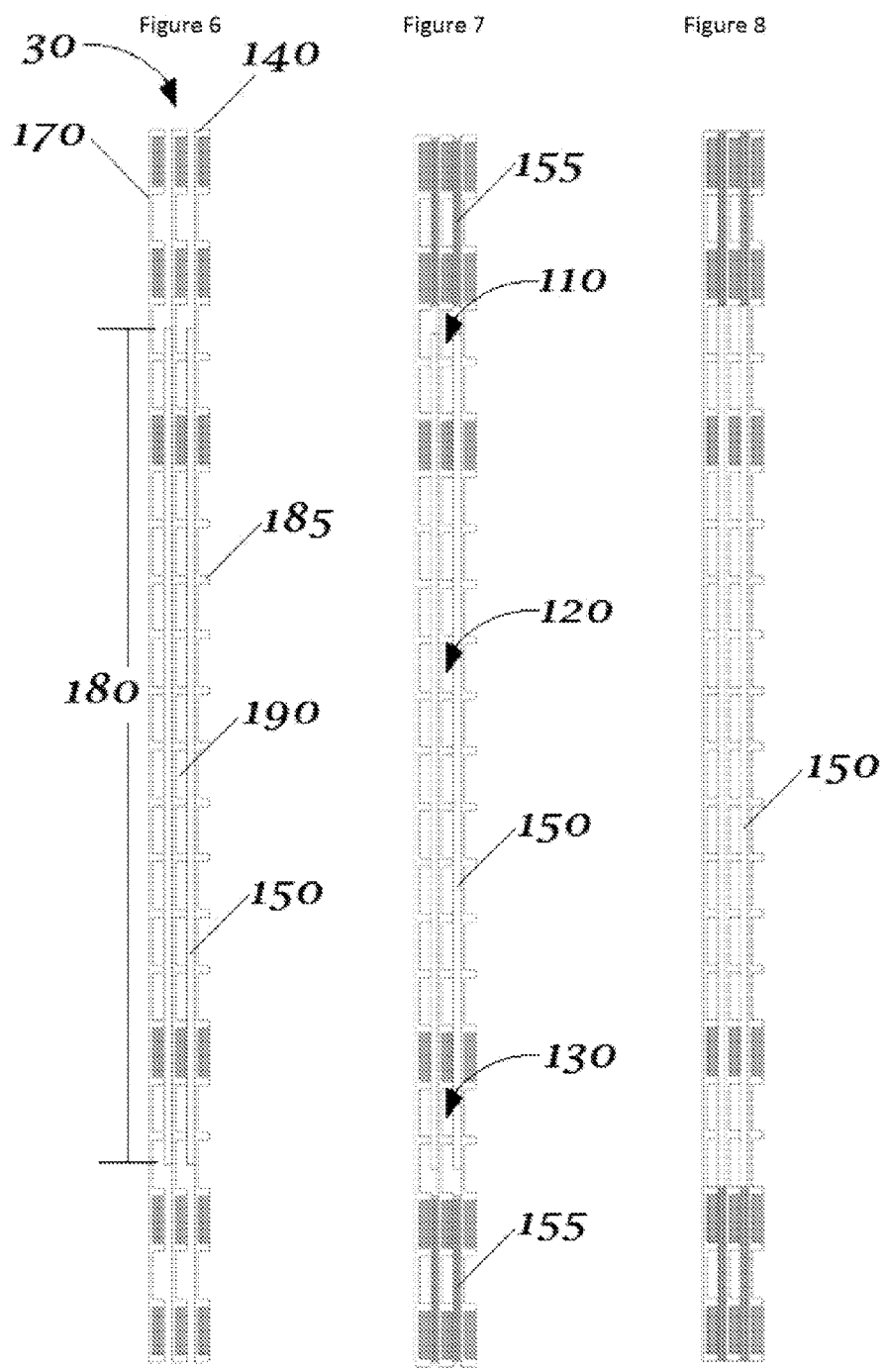

Figure 10
Figure 11
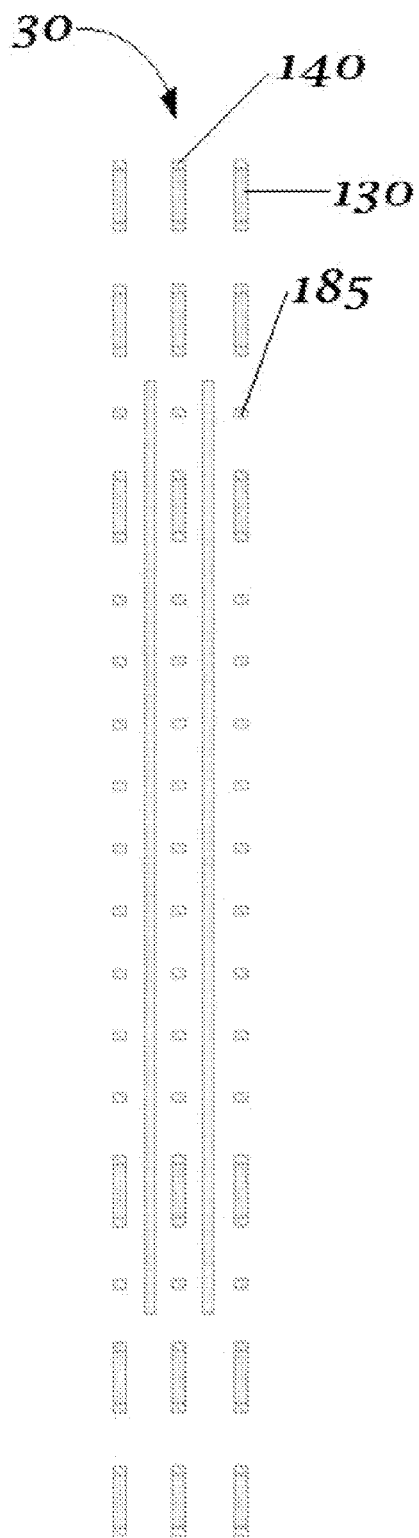
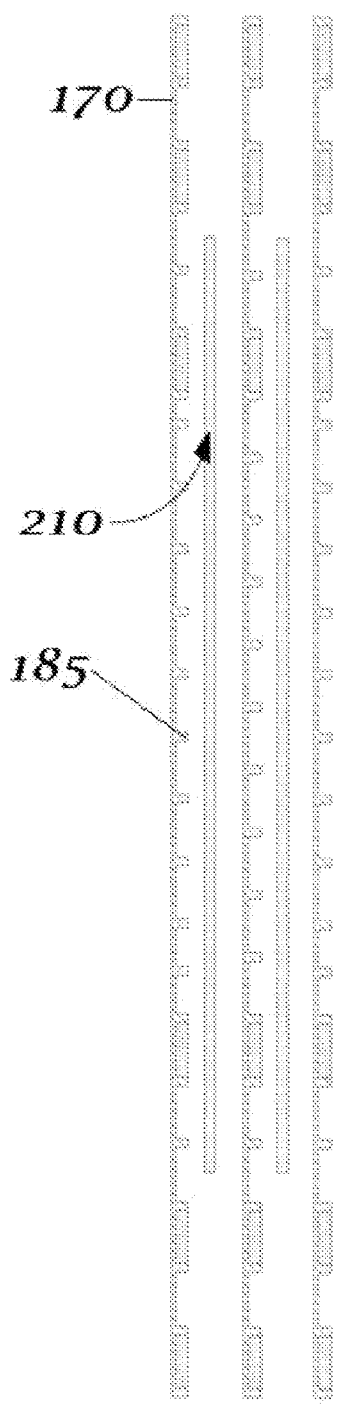

MULTIPHASE POROUS FLOW REACTORS AND METHODS OF USING SAME

CROSS-REFERENCE TO RELATED APPLICATIONS

This application is a National Phase entry under 35 U.S.C. Section 371 of PCT Application No. PCT/US12/64896, filed on Nov. 13, 2012, entitled "MULTIPHASE POROUS FLOW REACTORS AND METHODS OF USING SAME", which claims benefit of priority under 35 U.S.C. §119(e) to both U.S. Provisional Patent Application No. 61/600,661, entitled, "MULTIPHASE POROUS FLOW REACTORS AND METHODS OF USING SAME," filed Feb. 19, 2012, and to U.S. Provisional Patent Application No. 61/559,277, entitled, "MULTIPHASE POROUS FLOW REACTORS AND METHODS OF USING SAME," filed Nov. 14, 2011. The foregoing PCT application and provisional applications are herein incorporated by reference in their entirety.

STATEMENT REGARDING FEDERALLY-SPONSORED RESEARCH

The government may have rights in this research pursuant: ARPA-E DE-AR0000007.

BACKGROUND

The demand for alternative sources for fuels and chemicals has been growing significantly over the last years to reduce reliance on petroleum and to lower greenhouse gas emissions. To meet this increasing demand, a number of new bioprocesses have been developed to take advantage of non-traditional feedstocks such as biomass, biological and industrial waste streams, and even just sunlight and carbon dioxide. Some of the most promising of these advanced bioprocesses are syngas fermentation, electro fuels, and the light-driven cultivation of algae and cyanobacteria, all of which require the supply of gaseous feedstocks (e.g. $CO_3$, CD, $H_2$) as the primary input. Effectively supplying these gases to the biological catalysts is one design parameter for any cost-effective bioreactor solution intended to deploy these processes at a commercial scale. The issue of gas mass transfer has been addressed previously with a variety of reactor configurations, such as bubble aerated-stirred tank reactors and air-lift reactors, particularly for submersed aerobic fermentations. In order to ensure sufficient gas transfer to the submersed biocatalyst, energy intensive and technically complex agitation systems, which can be difficult to scale, may be required. Even in less complex trickle bed reactors, which are often used in mixed culture wastewater applications, the organisms are still separated from the gas phase by a significant layer of water, which slows down gas mass transfer to the cells.

SUMMARY

The present disclosure relates to capillary-flow reactors (also referred to as "porous flow reactors" or "PFRs") for performing multiphase chemical and biological transformations, and methods of using the capillary-flow reactors.

Generally, the capillary-flow reactors include three regions: a liquid-contacting region a gas-contacting region and a liquid-collection region. The capillary-flow reactors can have a single chamber, for example within which the three regions may be co-located (see e.g. FIGS. 26-28), or the reactors may have two (see e.g. FIGS. 17, 24 and 25), three (see e.g. FIGS. 1, 3, 13, 14, 16, 21, 22, 29) or more chambers (see e.g. FIGS. 19-20) wherein each chamber includes one or more regions. A porous substrate extends from a liquid-contacting region through a gas-contacting region to a liquid-collection region. For example, a porous substrate extends from within a liquid-contacting region through a gas-contacting region, and may extend into a liquid-collection region. As another example, the porous substrate may extend from within a liquid-contacting region through a gas-contacting region into a liquid-collection region. The porous substrate is capable of wicking liquid and may have reaction facilitators such as catalysts, enzymes, biologically-active microorganisms and/or other substances capable of facilitating reactions present on and/or in (collectively, "coated" or "loaded") the porous substrate in at least the gas-contacting region of the reactor. The capillary-flow reactor also includes a housing enclosing one or more of the regions. In some embodiments, the capillary-flow reactor is configured for continuous porous flow, even after the porous substrate is completely wet.

In some embodiments, the porous substrate may comprise multiple segments of porous substrate spanning one or more of the regions while maintaining fluid contact with the other porous substrate(s) (see, e.g., FIGS. 17-18). In some embodiments, the reactor includes multiple porous substrates (which may comprise multiple segments), each of which span at least from a liquid-contacting region and through a reaction (gas-contacting) region, and in some embodiments also span a liquid-collection region, and are configured in the reactor to prevent or alleviate cross-flow between the porous substrates (see. e.g., FIGS. 1-11, 21-22, 25 and 28). For example, the multiple porous substrates may be spaced apart and arranged in parallel, or as another example the multiple porous substrates may be spaced apart and form a zig-zag pattern. Or as yet another example, the multiple porous substrates may be spaced-apart in the same plane.

In some embodiments, PFRs include: a housing encompassing at least one chamber, which chamber defines at least a gas-contacting region of the reactor; a porous substrate extending through the gas-contacting region of the reactor, wherein the porous substrate includes at reaction facilitator in at least a portion of the gas-contacting region of the reactor; a pair of ports in the housing configured to permit a gas comprising a reactant to circulate through the gas-contacting region of the reactor and to contact the porous substrate; a liquid-contacting region; and, a liquid-collection region, wherein the porous substrate provides fluid communication at least between the liquid-contacting region and the gas-contacting region, and further wherein the reactor is configured to support flow of liquid (which can be continuous or intermittent) through the porous substrate for a desired time period provided there is liquid removed from the porous substrate in the liquid-collection region. In further embodiments, the porous substrate extends from within the liquid-contacting region through the gas-contacting region into the liquid-collection region. In some embodiments, the reactor is configured to operate in a downflow mode. In other embodiments, the reactor is configured to operate in an upflow mode. In some embodiments, the reactor is configured to collect liquid in a portion of the liquid-collection region that is discontinuous from the end of the porous substrate from which liquid is removed. In some embodiments, the reactor is configured to run photosynthetic reactions and one or more of the at least one gas-contacting chambers is configured for light transparency. In other embodiments, the housing encompasses a series of vertically-aligned chambers, with one or more chambers defining gas-contacting regions, a chamber defining a liquid-contacting region, and a chamber defining a liquid-collection region, with the gas-contacting regions located between the liquid-contacting and liquid-collection regions. In some embodiments, the reaction facilitator is chosen from microorganisms, catalysts, enzymes and combinations thereof.

In some embodiments chemical and biological reactions involving a gas are accomplished by: adding liquid, which may contain reactants and/or nutrients for maintaining the viability of the reaction facilitator(s) to the liquid-contacting region; circulating gas, which contains reactants, into and out of the gas-contacting region, and maintaining flow of the liquid through the porous substrate in the gas-contacting region by removing liquid from the liquid-collection region. In some embodiments, liquid may be removed intermittently. In some embodiments, liquid may be removed continuously. When liquid in the liquid-contacting region contacts the porous substrate, it flows at least by porous flow (capillary action) into and through the porous substrate to the gas-contacting region. Chemical or biological transformations occur in the gas-contacting region, where the catalysts, enzymes, and/or microorganisms are present on and/or within the porous substrate to facilitate reactions of reactants in the gas and/or liquid phases. The liquid, which may now include product, continues to travel by porous flow into the liquid-collection region and/or out of the porous substrate.

In some embodiments, wherein the product has an appropriate vapor pressure such that it evaporates in the gas-contacting region, it may be collected in the gas stream flowing out of the gas-contacting region. In some embodiments, products may be produced in the gas phase in the gas-contacting region, the liquid phase in the gas-contacting region, or both phases. In some embodiments, products produced in the gas phase are recovered from the gas-contacting region, for example along with gas that circulates into and out of the gas-contacting region. As described above, in some embodiments, products produced in the liquid phase in the gas-contacting region travel by porous flow to the liquid-collection region, wherein in some embodiments product may be recovered from the liquid leaving the liquid-collection region.

In some embodiments liquid flows out of the porous substrate with the assistance of gravity and/or added or reduced pressure. In some embodiments, products are recovered from the liquid. In some embodiments, the liquid is recycled back into the porous substrate. In yet other embodiments the liquid may pass into additional PFRs having similar or different reaction facilitators. In some embodiments the product is retained in the gas-contacting region on the porous substrate. In some embodiments the product is harvested from the porous substrate. In some embodiments the product is harvested with the porous substrate. In some embodiments the product is harvested from a porous substrate different from that in the gas-contacting region. In some embodiments the product is harvested with a porous substrate different from that in the gas-contacting region.

In some embodiments, liquid can be collected by evaporation after it flows through the gas-contacting region. For example, in some such embodiments, the liquid flows upward through the gas-contacting region of the porous substrate from a first end of the gas-contacting region nearer the bottom of the reactor to a second end of the gas-contacting region nearer the top of the reactor ("upflow mode"), and is evaporated in an evaporation region of the porous substrate at or above the second end of the gas-contacting region. In further embodiments the gas-contacting region and liquid-collection region may overlap (see, e.g. FIG. 26). In other such embodiments, liquid is added at a first end of the porous substrate, flows through a liquid-contacting region of the porous substrate that is at least partially located nearer the bottom of the reactor than the gas-contacting region of the porous substrate, and is evaporated in an evaporation region of the porous substrate that is at least partially located nearer the top of the reactor than the gas-contacting region.

In some embodiments, liquid can be collected directly as liquid after it flows through the gas-contacting region. For example, in some such embodiments, the liquid flows downward through the gas-contacting region of the porous substrate from a first end of the porous substrate nearer the top of the reactor to a second end of the porous substrate nearer the bottom of the reactor ("downflow" mode) and is collected in a liquid-collection region at or below the second end of the porous substrate. In other such embodiments, liquid is added at a first end of the porous substrate, flows through a liquid-contacting region that is at least partially nearer the top of the reactor than the gas-contacting region, and is collected in a liquid-collection region after it flows out of the second, opposite end of the porous substrate.

Regardless of whether the liquid is collected as a gas or liquid, when liquid in the liquid-contacting region contacts the porous substrate, it flows by porous flow (capillary action) through the porous substrate from the liquid-contacting region through at least the gas-contacting region. Chemical or biological transformations occur in the gas-contacting region, where the catalysts, enzymes, and/or microorganisms are present on and/or within the porous substrate to facilitate reactions of reactants in the gas and/or liquid phases. The liquid, which may now include product, continues to travel by porous flow into the liquid-collection region.

In some embodiments, methods of performing gas-liquid phase processes include: driving a continuous flow of liquid through a porous material for a desired time period by providing a first liquid at a first end of the porous material and removing the first liquid from a second end of the porous material, wherein the porous flow material is at least partially enclosed in a housing of a PFR; and, circulating a first gas containing a reactant into a first gas-contacting region of the PFR facilitating a reaction between the reactant and a reaction facilitator coated on at least a portion of the porous material, which produces a product. In further embodiments, the porous material is entirely enclosed within the housing of the PFR. In other embodiments, the process also includes recovering the product: such as in a first liquid as the first liquid flows out of the porous material at the second end of the porous substrate, and/or in the gas phase, and/or by removing product which may crystallize on the porous material by removing the porous material from the reactor and/or by flowing a second liquid over the crystallized product to dissolve the product and remove it from the reactor with the second liquid. In some embodiments, the reaction is a phototrophic reaction. In some embodiments, the reaction is an aerobic reaction and an anaerobic reaction, and includes circulating a second gas comprising a second reactant into a second gas-contacting region of the PFR, wherein the aerobic reaction occurs in one of the first or second gas-contacting region and the anaerobic reaction occurs in the other of the first or second gas-contacting regions. In some embodiments, the reaction facilitator is chosen from photosynthetic algae, cyanobacteria, a purple nonsulfur bacteria and combinations thereof and the product is chosen from intracellular accumulated carbohydrate, lipid and protein-type product, and combinations thereof. In some embodiments, wherein the reactant is carbon dioxide, the reaction facilitator is *Heterococcus coloradii* and the product is an intracellular fatty acid containing omega-3 fatty acids. In some embodiments, wherein the reaction facilitator is chosen from methanotrophic bacteria, the product is chosen from an intracellular accumulated carbohydrate, lipid, protein, and polyhydroxyalkanoate-type product and combinations thereof. In some embodiments, wherein the gas reactant is chosen from natural gas, methane, and combinations thereof, the reaction facilitator is *Methylococcus capsulatus*, and the product is a single cell protein. In some embodiments, the reactant is one or more of carbon dioxide, carbon monoxide, hydrogen, methane, hydrogen sulfide, volatile organics, and combinations thereof. In some embodiments, the product is one or more of ethanol, butanol, acetic acid, butyric acid, amino acid and longer chain fatty acids, alkenes, isoprene and combinations thereof.

The continuous PFR has a wide variety of applications. For example, the PFR may be configured as a bench-top research tool, for example for studying cells immobilized on a porous substrate. As another example, the PFR may be configured as a photobioreactor for cultivation of photosynthetic microorganisms, including large scale and continuous cultivation of photosynthetic microorganisms. As yet another example, the PFR may be configured for production of bioethanol, including large-scale production of bioethanol. As another embodiment, the PFR may be configured to produce fermentable sugar from photosynthetic microorganisms, including large scale production of fermentable sugar. As yet another example the PFR may be used for the biotransformation of methane such as that found in natural gas to products, including the large scale biotransformation of methane to products. As yet a further example, the PFR may be used for syngas fermentation, including large-scale syngas fermentation.

DESCRIPTION OF DRAWINGS

FIG. 6 is an end view of the ribbed support section of the embodiment of FIG. 3.

FIG. 7 is an end view of an alternative embodiment of a ribbed support section suitable for use in the multiphase PFR of FIG. 3.

FIG. 8 is an end view of yet another embodiment of a ribbed support section suitable for use in the multiphase PFR of FIG. 3.

FIG. 10 is an end cut view of the ribbed support section of the multiphase PFR of FIG. 3 taking along line I-I in FIG. 9.

FIG. 11 is a side end view of another embodiment of a ribbed support section suitable for use in the multiphase PFR of FIG. 3.

DETAILED DESCRIPTION

I. Definitions

Figure 1:
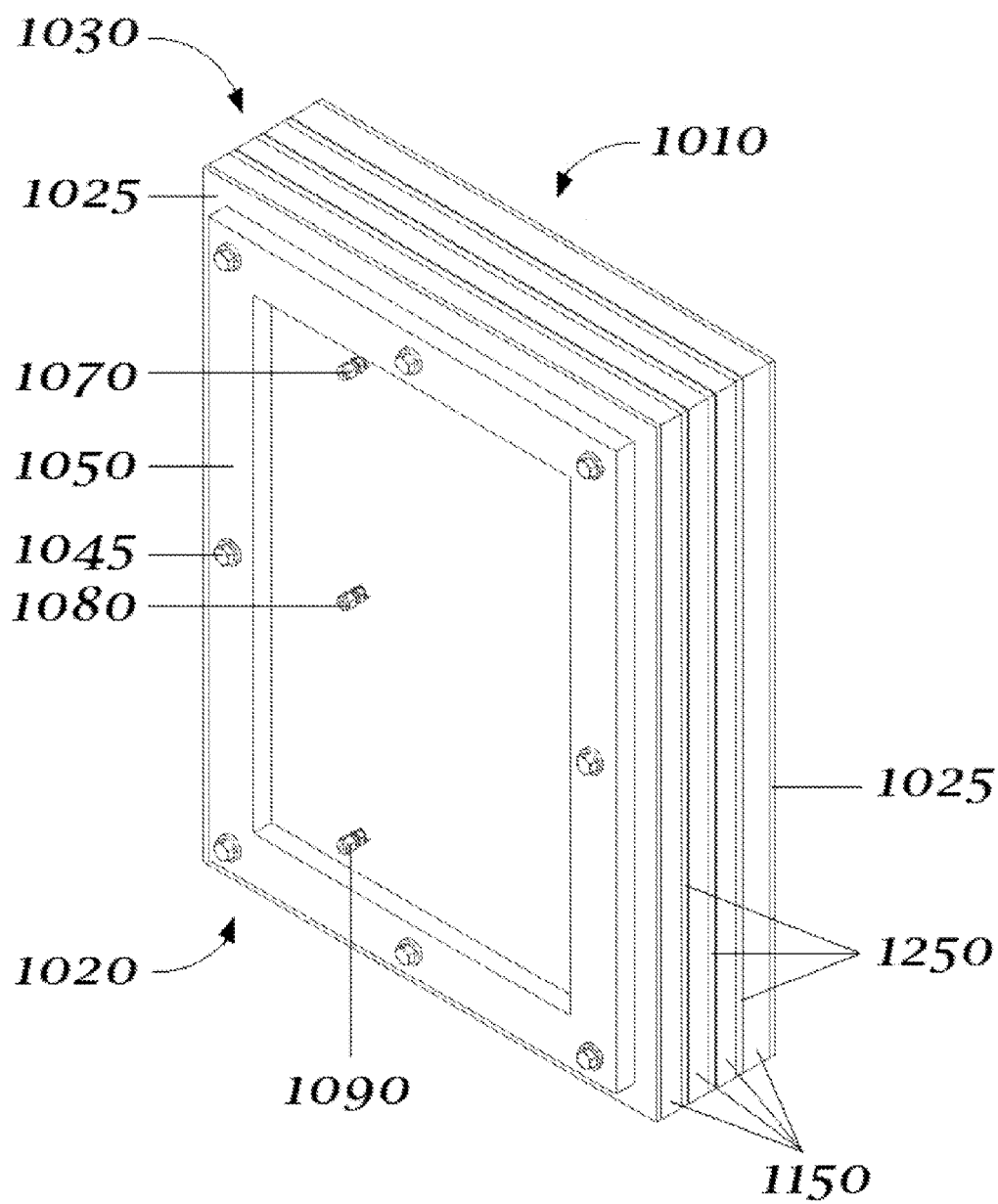
FIG. 1 is a perspective view of an embodiment of a multiphase PFR.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrase "for example," "such as," "including" and the like are used herein, the phrase "and without limitation" is understood to follow unless explicitly stated otherwise. Therefore, "for example ethanol production" means "for example and without limitation ethanol production."

The words "a," "an," "the," and "said" when used in the claims or in the description of "additional embodiments" mean "one or more" unless explicitly stated otherwise. For example, the phrase "a reactor comprising a chamber" means "a reactor comprising one or more chambers."

The terms "comprising" and "including" and "involving" (and similarly "comprises" and "includes" and "involves") are used interchangeably and mean the same thing. Specifically, each of the terms is defined consistent with the common United States patent law definition of "comprising"

and is therefore interpreted to be an open term meaning "at least the following" and is also interpreted not to exclude additional features, limitations, aspects, etc.

The term "substantially" (or alternatively "effectively") is meant to permit deviations from the descriptive term that don't negatively impact the intended purpose and/or deviations from the descriptive term taking into account inherent technological limitations. Descriptive terms are implicitly understood to be modified by the word substantially, even if the term is not explicitly modified by the word substantially.

The term "about" is meant to account for variations due to experimental error. All measurements or numbers are implicitly understood to be modified by the word about, even if the measurement or number is not explicitly modified by the word about. For example, the phrase, "the gas is conditioned to have a relative humidity of 95% or more" means "the gas is conditioned to have a relative humidity of about 95% or more."

The term "substrate" when used in connection with describing the PFR means a porous material, which facilitates porous (capillary) flow. The term "substrate" when used in connection with describing chemical or biological reactions means "reactant."

The term "multiphase" means two or more phases, for example biphasic or triphasic. The phases can be, for example aqueous liquid/gas phase. In some embodiments, a PFR can accommodate only one of each of two or more phases, such as running a biphasic process with a first liquid phase and a first gas phase. In some embodiments, a PFR can accommodate one or more of each of two or more phases, such as running a first biphasic process with a first liquid phase and a first gas phase, in addition to a second biphasic process with the first liquid phase and a second gas phase.

The term "reaction facilitator" is meant to generically encompass any substance that facilitates a chemical or biological process such as a catalyst, enzyme, or microorganism. A "reaction facilitator" can also be a microorganism for cultivation on the porous substrate using the PFR.

The term "catalyst" includes chemical catalysts and biological catalysts (biocatalysts).

The phrases "the porous substrate is loaded with reaction facilitator" and "the porous substrate is coated with reaction facilitator" and similar phrases are used interchangeably to mean that reaction facilitator is located on and/or within at least a portion of the porous substrate, for example at least a portion of the porous substrate is located in the gas-contacting region of the PFR. The phrases do not imply any certain amount or density of reaction facilitator, such as for example that the porous substrate is saturated with reaction facilitator. The phrases also do not imply any particular method of making a porous substrate having reaction facilitator on and/or within it. Non-limiting examples of methods of making a porous substrate loaded/coated with reaction facilitator include the methods described in U.S. Pat. No. 7,132,247, which is hereby incorporated by reference in its entirety, and also Flickinger et. al. Biotechnol. Prog. 2007, 23, 2-17 and Gosse et. al. JIMB. 2012, 39, 1269-78 which are also hereby incorporated by reference in their entirety.

The term "porous substrate" and "porous material" are used interchangeably and have the same meaning. The terms are intended to generically encompass any material that can wick a liquid, i.e. convey a liquid by porous flow and/or capillary action. The material can be, for example, paper, woven and non-woven fabrics made from natural, modified natural, or synthetic fibers which may or may not be of a fibrous composition. In some embodiments, the porous substrate can be from fiberous or nonfiberous materials comprising without limitation rayon, polyester, cellulose, polyethylene, polypropylene, glass fiber, nylon and blends of these in the form of wovens, nonwovens including those wet laid, dry laid, spunbond, thermalbond, flashspun, hydroentangled, melt blown, needle punch and composite fabrics. Examples 8 and 9 exemplify the use of 3 MM CHR chromatography paper as the porous substrate. Suitable alternatives, which may depend in part on compatibility with the specific reaction facilitator, may include paper towels (e.g. Procter & Gamble), glass fiber textile ((Polotsk-Steklovolokno), spunbond or dry laid rayon/polyester blend nonwoven such as Unifil 125 (Midwest Filtration) and the wet laid polyester cellulose blend Uniblend (Midwest Filtration). In some embodiments, the porous substrate can be digested and used in the cultivation process for producing biocatalysts used in the PFRs, for example the porous substrate can be digested and used as a nutrient in the cultivation process.

The phrases "PFR" and "capillary flow reactor" are used in the alternative and have the same meaning. The reactor includes a liquid-contacting "region," a gas-contacting (reaction) "region," and a liquid-collection "region," (which in some embodiments, can be an evaporation "region") and which regions are defined by one or more chambers. A "chamber" is an enclosure or structure (such as only a seal between regions, for example as exemplified in the embodiment of FIG. 18) that prevents or alleviates flow of gas or liquid between chambers except for desired flow, such as porous flow between chambers and/or gas and/or liquid circulation through a chamber via ports in fluid communication with the chamber. For example, a chamber may be a sealed enclosure that prevents or alleviates flow of gas or liquid into and out of the chamber (except for desired flow). As another example, a chamber may be open to the environment but have a sealed boundary preventing or alleviated gas or liquid flow between it and an adjoining chamber (such as exemplified in the two-chamber reactor of FIGS. 17-18). A "chamber" may include only a single region, or two or three regions may be co-located in a single "chamber." Some reactors and methods herein (as well as other reactor and method embodiments) can be described to operate in an "upflow" or "downflow" mode.

The term "upflow" is a term for describing the direction of porous flow in the gas-contacting region of a PFR, and specifically means flow through the porous substrate from a first end of the gas-contacting region that is nearer the bottom of the reactor to a second end of the gas-contacting region that is nearer the top of the reactor (i.e. the liquid flows at least partially against gravity). Consequently, an upflow reactor, also referred to as a reactor that operates in an upflow mode, includes a gas-contacting region in which liquid flows through the porous substrate from a first end of the gas-contacting region nearer the bottom of the reactor to a second end of the gas-contacting region nearer the top of the reactor. The term "downflow" is a term for describing the direction of porous flow in the gas-contacting region of a PFR, and specifically means flow through the porous material from a first end of the gas-contacting region that is nearer the top of the reactor to a second end of the gas-contacting region that is nearer the bottom of the reactor (i.e. the liquid flows at least partially with the assistance of gravity). Consequently, a downflow reactor, or alternatively a reactor that flows in a downflow mode, includes a gas-contacting region in which liquid flows through the porous substrate from a first end of the gas-contacting region nearer the top of the reactor to a second end of the gas-contacting region nearer the bottom of the reactor.

A "liquid-collection" region is a region in which liquid flowing through the porous substrate, at least in part due to porous flow, is intentionally removed from the porous substrate, directly as a liquid or indirectly as a gas, in order to support continuous porous flow through the reactor.

The phrases "capillary flow" and "porous flow" are used in the alternative and have the same meaning, and when used in connection with the reactor designs according to this disclosure, include reactors incorporating porous substrates perpendicular to the surface of the liquid in the liquid-contacting region as well as any other angle of inclination. In other words, the phrases "capillary flow" and "porous flow" are not limited to vertical flow, but include all other angles of inclination as well, provided that the liquid can flow through the substrate in whole or in part due to porous flow through the gas-contacting region from the liquid-contacting region to the liquid-collection region. Although not wishing to be bound by theory, it is believed that this flow is driven by movement from high liquid potential to low liquid potential. Further, the path of the porous substrate through the PFR (and therefore also the direction of porous flow) may be linear, non-linear, or may not follow a single straight-line path, including having one or more changes in direction and/or may involve one or more porous substrates.

The term "housing" when used to describe a component of a PFR refers to an enclosure enabling control of one or more environmental parameters in the reactor such as temperature, pressure, and humidity. For example, in FIG. 24, the cuboid enclosure 601 corresponds to the PFR housing.

When describing the dimensions of certain embodiments of PFRs, the term "depth" refers to the horizontal dimension of the reactor, which is substantially normal to the surface of the porous substrate. The term "height" refers to the vertical dimension of the reactor. The term "width" refers to the other horizontal dimension of the PFR.

II. Introduction

An embodiment according to the present disclosure provides PFRs for performing multiphase chemical and/or biological transformations, for example a biphasic chemical or biological transformation in which certain reactant(s) are in the gas phase, or as another example certain reactant(s) are in the gas phase and certain reactant(s) are in the liquid phase.

The PFRs comprise one of each of three regions: a liquid-contacting region, a gas-contacting region, and a liquid-collection region, and may include a housing enclosing at least the gas-contacting region. In some embodiments, the housing encloses a gas-contacting region or regions and also one or more liquid-contacting regions and/or one or more liquid-collection regions. In some embodiments, one or more regions are separated by a seal (also referred to a as a "chamber"). Accordingly, in some embodiments, the PFRs are single or multi-chamber (for example two-chamber, three-chamber, four-chamber or more) devices including at least one each of three regions: a liquid-contacting region, a gas-contacting region and a liquid-collection region. As is apparent from the description herein, each chamber of the PFR can include one, two or three regions resulting in numerous permutations all within the scope of this disclosure. For example, in some embodiments, the reactor is a one-chamber reactor including all three regions (see, e.g., FIG. 27). In some embodiments, the reactor is a two-chamber reactor, wherein for example one chamber includes a liquid-contacting region and a gas-contacting region and the second chamber includes a liquid-collection region (see, e.g., FIGS. 24 and 25). In some embodiments, the reactor is a three-chamber reactor, in which for example each chamber includes a distinct region (see, e.g., FIGS. 14, 21 and 22). In some embodiments, the reactor is a four-chamber reactor in which for example a first chamber includes a liquid-contacting region, a second chamber includes a liquid-contacting region, a third chamber includes gas-contacting region, and a fourth chamber includes a liquid-collection region. In some embodiments, the reactor has four or more chambers, wherein for example a liquid-contacting region is in the first chamber, a liquid-collection region, such as an evaporation region is the last chamber, and the middle chambers encompass gas-contacting regions (see e.g., FIG. 19). In some embodiments, the reactor has four or more chambers, such as for example one chamber defining a gas-contacting region, multiple chambers each defining liquid-contacting regions, and multiple chambers each defining liquid-collection regions (and in further embodiments, the reactor can include multiple chambers each defining gas-contacting regions), or for example one chamber defining a liquid-contacting region, one chamber defining a liquid-collection region, and multiple chambers each defining a gas-contacting region.

The PFRs also comprise a porous substrate capable of wicking liquid and providing fluid communication at least between the liquid-contacting region and the gas-contacting region and in some embodiments from the liquid-contacting region through the gas-contacting region to the liquid-collection region. In some embodiments, for example, the porous substrate extends from a liquid-contacting region through a gas-contacting region into a liquid-collection region. As another example, a porous substrate extends from within a liquid-contacting region through two or more gas-contacting regions into a liquid-collection region, which may be an evaporation region. In some embodiments, reaction facilitators, such as catalysts, enzymes, biologically-active microorganisms and/or other substances capable of facilitating reactions are coated on and/or within the porous substrate, generally in the gas-contacting region of the reactor. In PFRs having more than one gas-contacting regions (or more than one chamber enclosing a gas-contacting region), each gas-contacting region can include the same reaction facilitators, different reaction facilitators, or some of the same reaction facilitators as other regions/chambers. Each of the gas-contacting regions can be exposed to the same, different, or some of the same gas-phase reactants as the other chambers.

In some embodiments, the PFRs are downflow single or multi-chamber (for example two-chamber, three-chamber, four-chamber or more) devices including at least one each of three regions: a liquid-contacting region, a gas-contacting region, and a liquid-collection region. In some embodiments, the PFRs are upflow single or multi-chamber (for example two-chamber, three-chamber, four-chamber or more) devices including at least one each of three regions: a liquid-contacting region, a gas-contacting region, and a liquid-collection region, which may be an evaporation region.

Further, PFRs can be adapted for a wide variety of applications. Whereas they were first conceived as a small upflow device for studying cells immobilized on a surface, specifically, *Clostridium ljungdahlii*, it was unexpectedly discovered that capillary flow reactors can be scaled-up for commercial applications, and used for a wide variety of applications, with or without an evaporation region as the liquid-collection region, including photosynthetic reactions, dark (i.e., non-photosynthetic) reactions, reactions in which substrate is in the gas phase only, and reactions in which substrate is in the gas phase and the aqueous phase.

Also contemplated are PFRs that can run multiple processes and/or multi-step reactions. In some embodiments, for example, the capillary flow reactor is a four-chamber reactor having a liquid-contacting chamber, a first and a second gas-contacting chamber and a liquid-collection chamber. In some embodiments, such reactors may be configured to run a different process in each gas-contacting chamber, for example by circulating gas with a different set of reactants through each gas-contacting chamber and/or by loading the porous substrate within each gas-contacting region with a different set of reaction facilitators. In some embodiments, such reactors may be configured to run a multi-step process, wherein the reaction in the first gas-contacting chamber produces a product or products, which are the substrates for the reaction in the second gas-contacting chamber. In some embodiments, running multi-step reactions or multiple processes in multi-chamber reactors has the advantage of preventing or alleviating reactants or substrates from one process from contaminating the other process, especially wherein the reactants and/or substrates of one process or step may be detrimental to the other process or step.

Also contemplated are reactors having multiple-reaction zones connected by porous flow, encompassing a variety of embodiments such as reactors having an aerobic zone followed by an anaerobic zone and vice versa, and reactors having a phototrophic zone followed by a heterotrophic zone and vice versa. In some embodiments, the capillary flow reactor can be configured to run multiple different multi-phasic reactions. Also contemplated is a system of multiple capillary flow reactors, wherein each reactor runs the same or different multiphasic reactions as another PFR in the system.

As other examples of design flexibility, in some embodiments, the PFRs are useful for performing multiphase reactions in which the reactant(s) is/are present in both gas and aqueous phases. In such embodiments, the aqueous phase reactant(s) can be, for example, sugars and sugar alcohols such as sorbitol, and the gaseous phase reactant(s) can be, for example, $O_2$, $CO_2$, CO, $H_2S$ and volatile organics. In some embodiments wherein the reactant(s) is/are in the gas and aqueous phases, the target products can be in the aqueous phase (such as sorbose from sorbitol), primarily in the aqueous phase, or in both the aqueous and gas phases.

Alternatively, in some embodiments wherein the reactant(s) is/are both in the gas and aqueous phases, the target products can be primarily in the aqueous phase, primarily in the gas phase, or in the gas and aqueous phases. The partitioning of a given target product into the liquid phase or into the gas phase may change depending on the temperature and/or pressure at which the reaction takes place.

As yet another example of design flexibility, in some embodiments, the PFRs are suitable for multiphase reactions wherein the reactant(s) is/are in the gas phase only. Here too, in some embodiments, the target products can be primarily in the liquid phase, in both the gas phase and the liquid phase, or primarily in the gas phase.

In some embodiments, the PFRs are configured to run phototrophic reactions, or reactions which otherwise require light. In some embodiments, the phototrophic reactions involve photosynthetic microorganisms as reaction facilitators and the gas phase substrate can be, for example, carbon dioxide. In some embodiments involving photosynthetic microorganisms as reaction facilitators, the target product may accumulate within the cells immobilized on the porous substrate (such as triglycerides, fatty acids including laurate, palmitate, and omega-3s), or may be secreted into the liquid phase (such as fatty acids including laurate, palmitate, sucrose, ethanol, and butanol), or may be primarily in the gas phase (such as isoprene, ethylene, propylene, and butylene).

In some embodiments, the PFRs are suitable for running reactions which do not require light ("dark" reactions). In some embodiments, the dark reactions involve organisms as reaction facilitators and the gas phase substrates can be, for example, carbon dioxide, carbon monoxide, hydrogen, methane, hydrogen sulfide and/or volatile organics. In some dark reaction embodiments involving organisms as reaction facilitators, the target products can be secreted into the liquid phase (such as ethanol, butanol, acetic acid, butyric acid, amino acids and longer chain fatty acids such as laurate and palmitate). In some dark reaction embodiments involving organisms as reaction facilitators, the target products can be primarily in the gas phase (such as isoprene, ethylene, propylene, and butylene).

III. Multiphase PFRs

Figure 2:
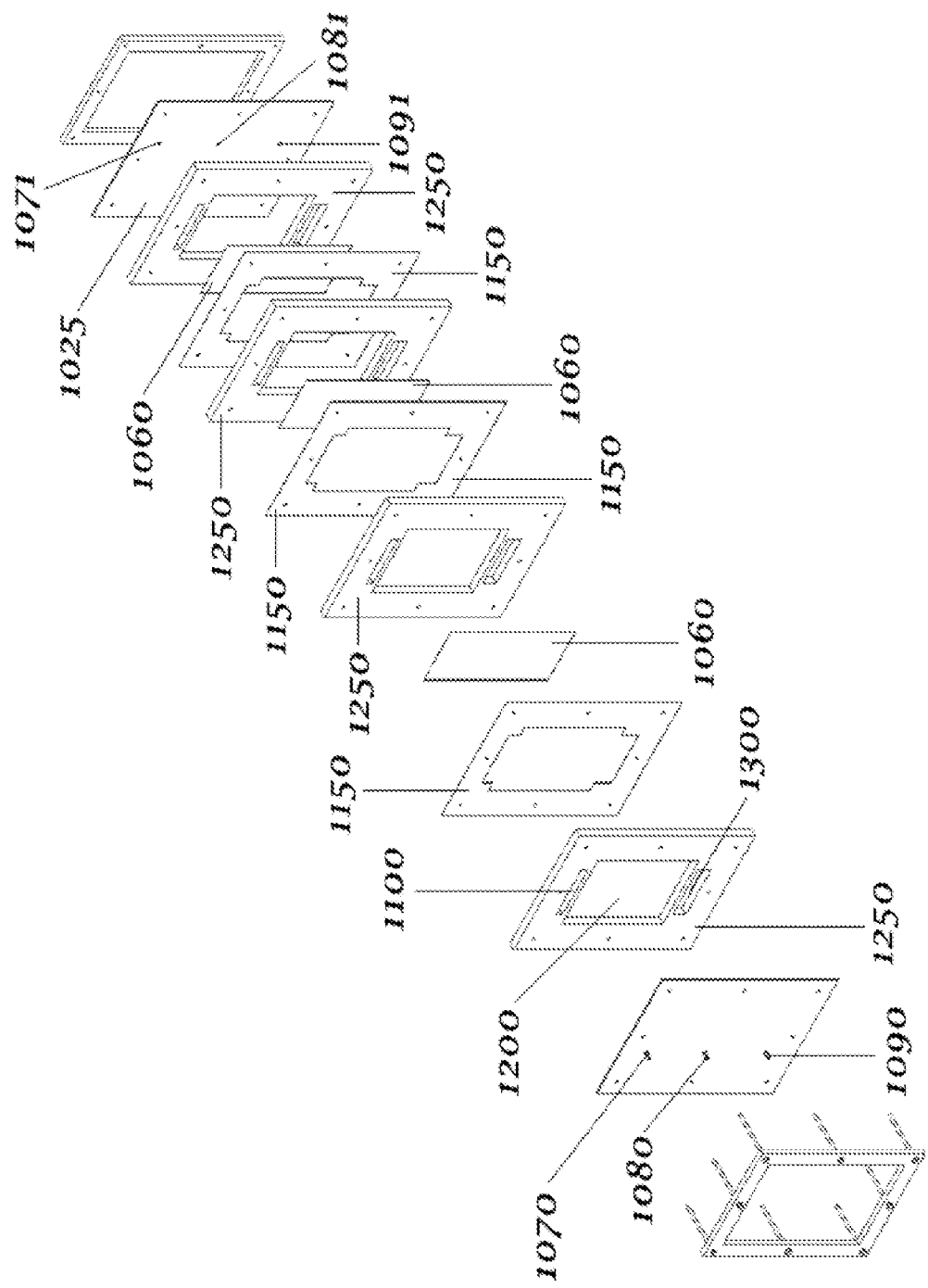
FIG. 2 is an exploded view of the embodiment of FIG. 1

Referring now to the figures wherein like reference numerals indicate like elements, FIGS. 1 and 2 illustrate an embodiment of a three-chamber PFR 1010. The PFR 1010 includes: a housing 1020 having side plates 1025 and optional structural components 1050. The housing encloses multiple chamber spacers 1250, multiple porous substrate spacers 1150 and multiple sheets of porous substrate 1060. The chamber spacers 1250 have three openings defining a first region 1100, which is a liquid-contacting region, a second region, which is a gas-contacting region 1200, and a third region 1300, which is a liquid-collection region. When the PFR 1010 elements are assembled and secured together with the system of nuts, washers and bolts 1045, the chamber spacer elements 1250 define three chambers (each defining one of the three regions). The porous substrate spacers 1150 help prevent or alleviate cross-flow between sheets of porous substrate 1060 and, in addition to structural components 1050 impart strength and alleviate distortion of the side plates 1025.

The PFR 1010 also includes three pairs of ports, a first pair 1090, 1091, a second pair 1080, 1081 and a third pair 1070, 1071 for providing and removing fluid to the reactor. In some embodiments ("downflow" embodiments), wherein, for example the PFR 1010 is oriented in operation to position the first pair of ports 1090, 1091 below the third pair of ports 1070, 1071, the first pair of ports 1090, 1091 provides and removes liquid, which may contain product, to/from the liquid-collection region 1300; the second pair of ports 1080, 1081 provides and removes gas, which may contain reactants, to/from the gas-contacting region 1200; and the third pair of ports 1070, 1071 provides and removes liquid, which may contain nutrients for the reaction facilitators and/or reactants, to/from the liquid-contacting region 1100. Thus, in these downflow embodiments, liquid is moved through the system of FIGS. 1 and 2 and the porous substrate 1060 by first entering the system as a liquid from port 1070 into the a liquid-contacting region 1100 through the gas-contacting region 1200 to a liquid-collection region 1300 and then out of port 1090 and 1091 as a liquid. Accordingly continued movement of liquid through the porous substrate 1060 is maintained by fluid leaving the porous substrate at the bottom of the reactor.

In other embodiments (e.g. certain "upflow" embodiments), the first pair of ports 1090, 1091 provides and removes liquid, which may contain nutrients for the reaction facilitators and/or may contain reactants, to the region 1030, now a liquid-contacting region; the second pair of ports 1080, 1081 still provides and removes gas, which may contain reactants, to/from the gas-contacting region 1200; and the third pair of ports 1070/1071 provides and removes gas (and optionally may alternatively provide and remove liquid), to/from region 1100, now a liquid-collection (evaporation) region. Accordingly, in these upflow embodiments, liquid is moved through the system of FIGS. 1 and 2 and the porous substrate 1060 by first entering the system as a liquid from port 1090 into the first region, now a liquid-contacting region 1300, through the gas-contacting region 1200 to the third region, now liquid-collection region (evaporation region) 1100 and then out of port 1071 as a gas. Accordingly, fluid leaves the top of the reactor to allow for the continued movement of liquid through the porous substrate 1060. The liquid may be collected and in some embodiments potentially cleaned and recycled.

A skilled person basis reading this specification should recognize that there are a wide variety of possible design changes. For example, the configuration of the pairs of ports 1070, 1071, 1080, 1081, 1090, 1091 in FIG. 1 and FIG. 2 represents one possible embodiment among a number of possible embodiments. For example, although the ports 1070, 1071 are shown to be positioned not directly opposite one another on either side of the housing 1020, in some embodiments, the ports 1070, 1071 are exactly opposite one another, and in some embodiments the ports 1070, 1071 may be on the same side of the housing 1020. As another example, although the gas-contacting region is illustrated as including only one set of ports 1080, 1081, in some embodiments, the gas-contacting region could include, for example, two sets of ports—one set dedicated to delivering and removing gas and another set dedicated to delivering and removing liquid. As another example, the above first-described embodiment, wherein liquid runs in a downflow mode, could be reconfigured with a liquid delivery system at the top of the device. This, in one embodiment, may be envisioned as a header portion in which the tops of each porous substrate slightly overlap, such that when liquid is delivered to the header portion, it is distributed among the porous substrates through a wicking action. The device could also be configured with a liquid delivery system that includes pressure and volume controls to provide rate control.

Figure 3:
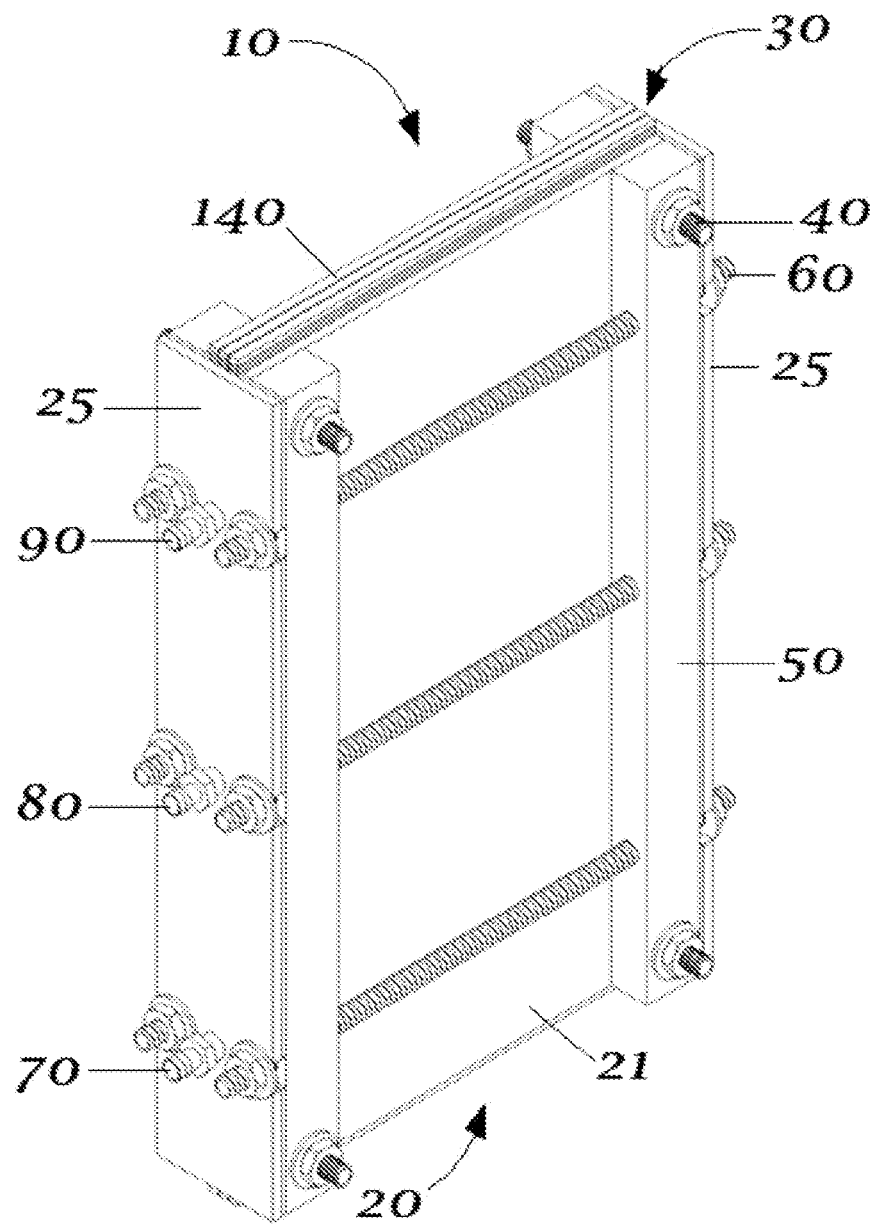
FIG. 3 is a perspective view of an embodiment of a multiphase PFR.

FIG. 3 illustrates an embodiment of a three-chamber PFR 10. The PFR 10 includes: a housing 20 having side plates 21 and end plates 25; a ribbed support section 30 including two or more sheets of ribbed support material 140 (three sheets for the embodiment of FIG. 3 further illustrated in FIGS. 4-7); a system of nuts, washers and bolts (in the embodiment shown, one nut-washer pair at either end of a bolt) 40 for securing together the side plates 21 and the ribbed support section 30; optional vertical structural components 50 for imparting strength and alleviating distortion of the side plates 21, which in the embodiment of FIG. 3 are also secured together with the system of nuts, washers and bolts 40 and a system of nuts, washers and bolts (in the embodiment shown, one nut washer pair at either end of a bolt) 60 for securing together the end plates 25 and alleviating bowing of the end plates 25.

The PFR 10 of FIG. 3 also includes pairs of ports 70, 71, 80, 81, 90, 91 (71, 81 and 91 shown in FIG. 5) for each of the three regions of the reactor 10. The ports 70, 71 are positioned in communication relationship with the liquid-contacting region such that liquid can be delivered to the liquid-contacting region through one port 70 and liquid not removed by the porous substrate 150 (or e.g. porous substrates, such as in the embodiment shown in FIGS. 4-12) can be removed through a port 71 on the opposite end plate. The ports 80, 81 are positioned in communication relationship with the gas-contacting region such that gas is delivered to the gas-contacting region through one port 80 and removed through another port 81. Finally, the ports 90, 91 are positioned in communication relationship with the liquid-collection region such that gas and/or liquid are delivered to the liquid-collection region through one port 90 and removed through the other port 91.

Figure 4:
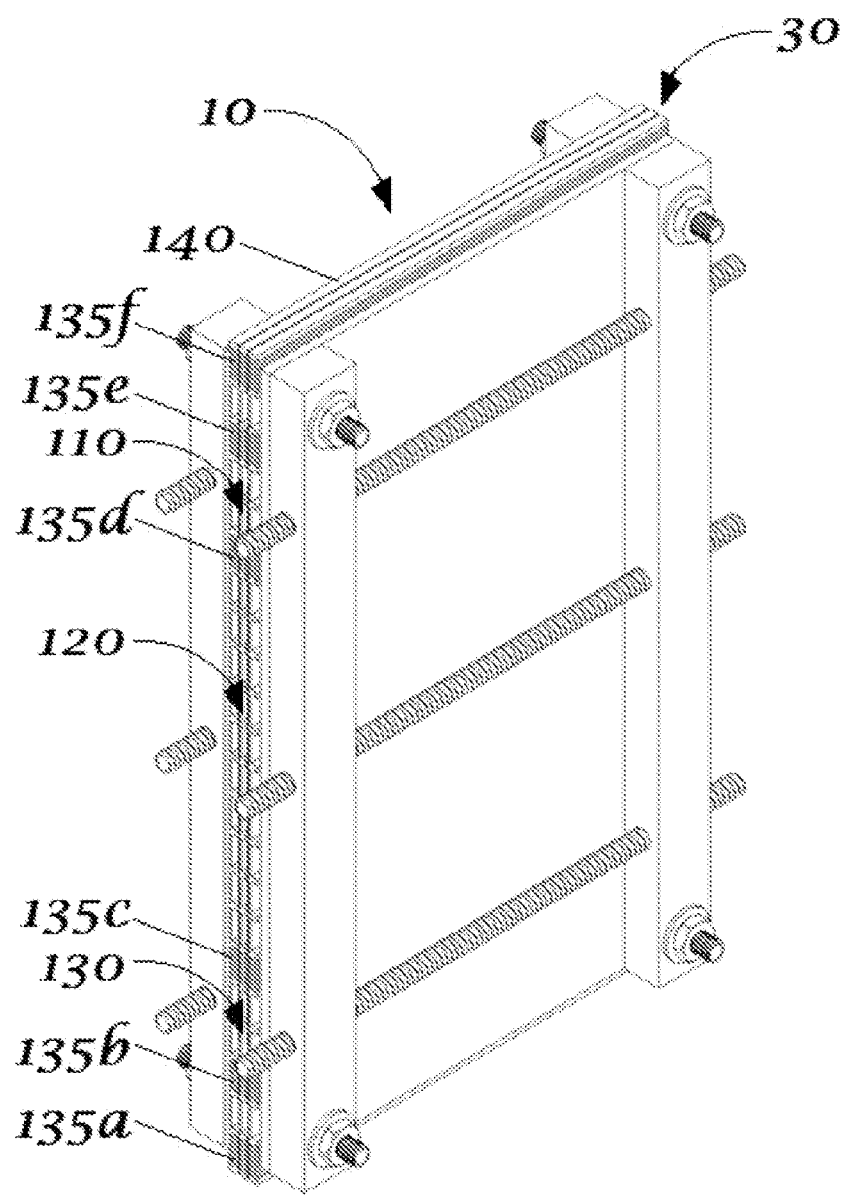
FIG. 4 is a perspective view of the embodiment of FIG. 3 with the end plates removed to expose the internal ribbed support section.
Figure 5:
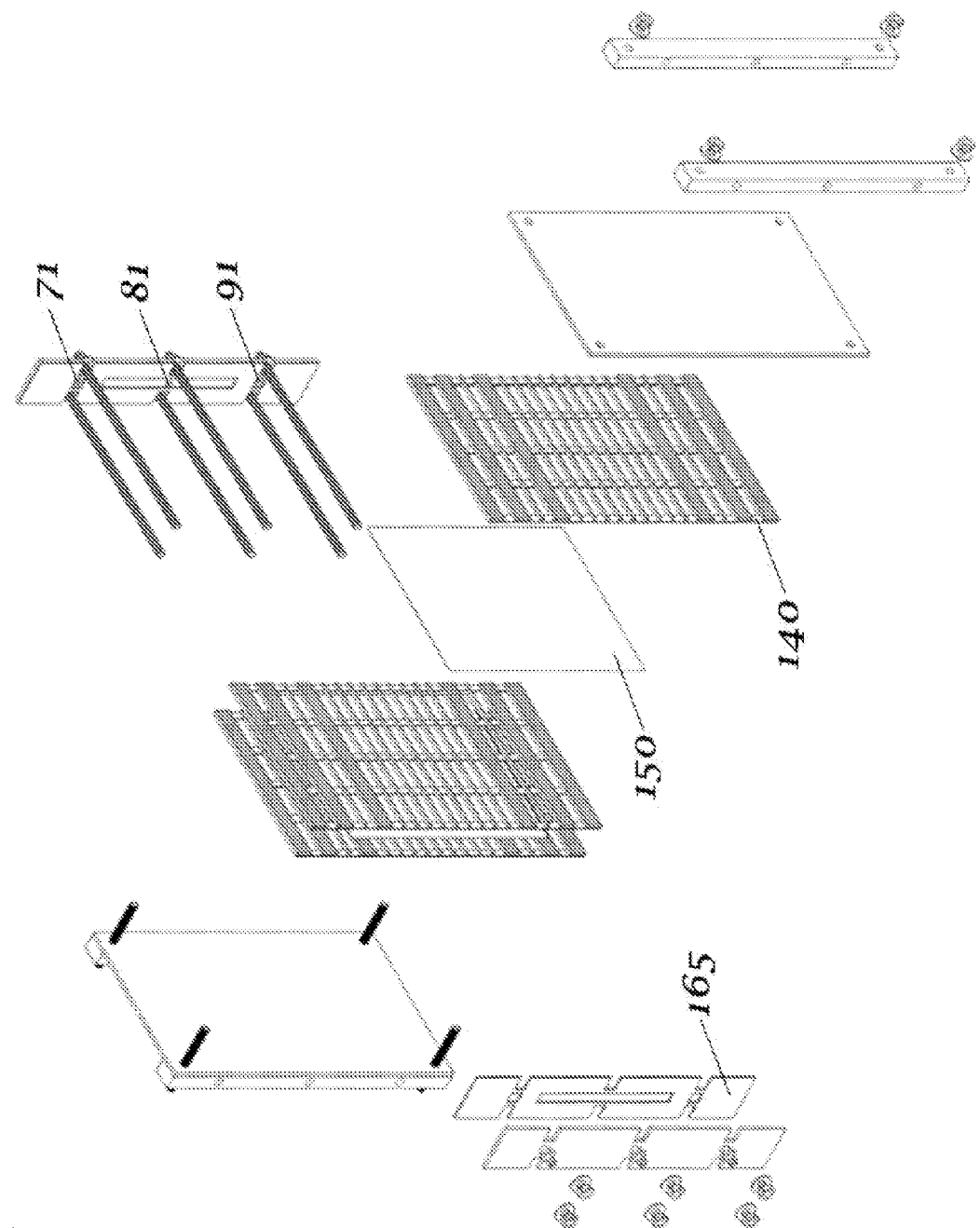
FIG. 5 is an exploded view of the embodiment of FIG. 3.

The PFR 10 also includes one or more porous substrates 150 (two porous substrates in the embodiment shown in FIGS. 3-5), which are not discernable in FIG. 3, but can be better observed, for example in FIGS. 5 and 6. The porous substrate 150, ribbed support section 30, and ribbed support materials 140, will be discussed in further detail in connection with FIGS. 5 and 6.

The illustrated specifics are exemplary only, and a person of skill could appreciate suitable alternatives. For example, the illustrated means for securing the side plates 21 and the end plates 25 are exemplary only. As can be appreciated from FIG. 3 the use of nuts and bolts in the illustrated embodiment, releasably secure together the side plates 21 and the end plates 25. In some embodiments, however, for example wherein the reactor is for one time use, the housing may not need to be releasably fastened together. Further, a person of ordinary skill in the art could readily understand from this disclosure that other means for securing together the side plates 21 and end plates 25, including other means for releasably securing together the side plates 21 and the end plates 25, are possible.

A skilled person could also appreciate, for example, that the configuration of the pairs of ports 70, 71, 80, 81, 90, 91 represents one possible embodiment among a number of possible embodiments. For example, although the ports 70, 71 are shown to be positioned directly opposite one another on either side of the housing 20, in some embodiments, the ports 70, 71 are not exactly opposite one another, and in some embodiments the ports 70, 71 may be on the same side of the housing 20. As another example, although the liquid-collection region is illustrated as including only one set of ports 90, 91, in some embodiments, the liquid-collection region could include, for example, two sets of ports—one set dedicated to delivering and removing gas and another set dedicated to delivering and removing liquid.

As yet another example of design flexibility, the number of vertical 50 and horizontal 60 structural components can be chosen to balance the cost of materials with the need or desire to alleviate or prevent distortion of the side plates 21 and end plates 25 of the housing 20 when the housing 20 is fastened together. However, some embodiments may have less than the depicted number of vertical 50 and/or horizontal 60 structural components, more than this number of vertical 50 and/or horizontal 60 structural components, or no vertical 50 and/or horizontal 60 structural components. Thus, for example, in some embodiments, the end plates 25 may be releasably secured together, but rather than using the horizontal 60 structural component as the bolt for securing the end plates together, each opposing end plate 25 can have its own set of nuts and bolts and can be secured directly to a side plate 21 or vertical structural component 50.

As another example of modifications within the skill of the art, although the housing 20 and structural components 50, as exemplified, are made from aluminum, a person of ordinary skill could easily make appropriate design choices regarding suitable housing materials.

FIG. 4 is a perspective view of the PFR 10 of FIG. 3, with the end plates of the reactor 10 intentionally left out of the illustration in order to show the internal structure of the PFR 10 of FIG. 3. The reactor 10 includes three sheets of ribbed support materials 140 and two sheets of porous substrate 150. Seals 135 (Labeled 135a-f) are integrated into the ribbed support material 140, defining three chambers: the upper and lower boundaries of the liquid-contacting chamber 130, the upper and lower boundaries of the gas-contacting chamber 120 and the upper and lower boundaries of the liquid-collection chamber 110. Specifically seals 135a form a barrier along the bottom side of the reactor 10 and seals 135f form a barrier along the top side of the reactor 10. Seals 135b, 135c together define the liquid-contacting chamber 130, seals 135c, 135d together define the gas-contacting chamber 120, and seals 135d, 135e together define the liquid-collection chamber 110. Once assembled, liquid is wicked from the liquid-contacting chamber 130 through the gas-contacting chamber 120 and into the liquid-collection chamber 110 by the porous substrate 150, but otherwise the seals 135 prevent or alleviate liquid and/or gas residing in each region to flow into another chamber of the reactor. In the reactor embodiment of FIG. 3, each region (i.e. liquid-contacting, gas-contacting, liquid-collection) is located in a distinct chamber of the reactor 10.

Figure 9:
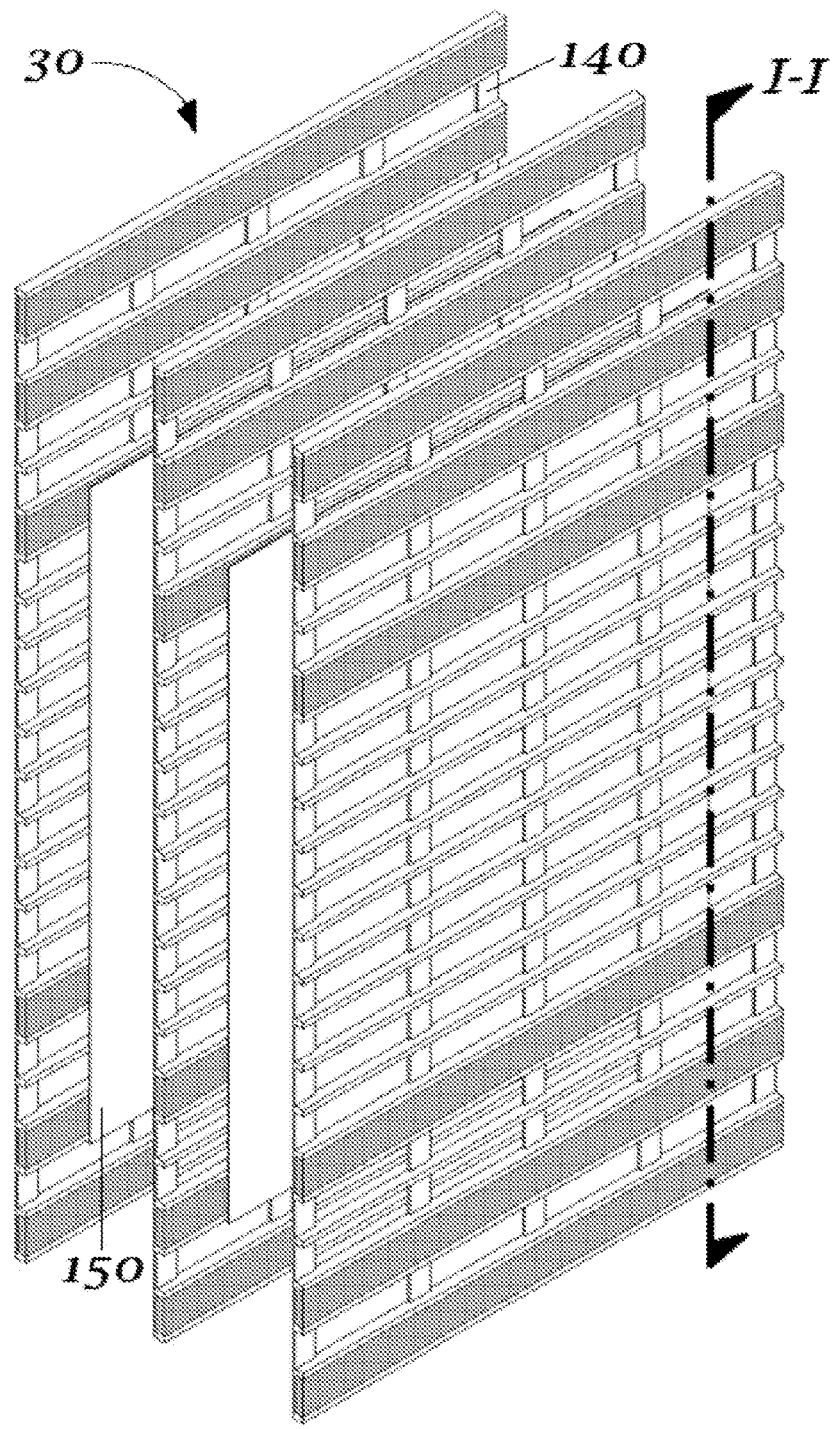
FIG. 9 is an exploded view of the ribbed support section of the multiphase PFR of FIG. 3.

FIG. 5 is an exploded view of the embodiment of FIG. 3 illustrating further details of the internal structure of the PFR 10 and how the particular PFR 10 is assembled. FIG. 9 is a perspective view of the internal structure of the reactor 10 of FIG. 3. As shown in FIG. 5 and in FIG. 9, sheets of porous substrate 150 are spaced apart from each other and from the side plates 21 of the reactor 10 by sheets of ribbed support material 140. As shown in FIGS. 4 and 6 among others, in the embodiment of FIG. 3, the seals 135 on a given sheet of ribbed support material 140 align with the seals 135 on the other sheets of ribbed support material 140 defining chambers within the reactor 10. More specifically, when the reactor 10 is assembled, the seals 135 from one sheet of ribbed support material 140 press against the corresponding seals 135 on the adjacent sheet(s) of ribbed support material 140 defining chambers within the reactor 10 to form a barrier that prevents or reduces gas or liquid leakage outside of the reactor 10 and cross flow between chambers of the reactor 10 beyond that which is intentionally a result of the porous substrate 150. The end plate gasket 165 is also shown.

FIG. 6 is an end view of the ribbed support section 30 of the PFR 10 of FIG. 3, again showing the alternating structure of porous substrate 150 and ribbed supports 140. FIG. 9 is an exploded view of the ribbed support section 30 of FIGS. 3, 4, and 5, also shown as an end view in FIG. 6. The ribbed support material 140 is configured with spaced-apart raised ribs on one side of the material 140 (and is flat on the other side of the material 140). In addition, as shown in FIG. 5, the spaced-apart raised ribs extend horizontally across the ribbed support material 140 and define channels 190 through which gas can flow, facilitating contact with the entire porous substrate 150 surface area.

In the illustrated embodiment, when the reactor 10 is assembled, the ribbed support materials 140 are positioned such that the spaced-apart ribs on each of the ribbed support materials 140 all face the same side plate 21 of the reactor and align. This orientation of the ribbed support materials 140 prevents or alleviates damage to the porous substrates 150, for example assisting in preventing the porous substrates 150 from crumpling when pressure is applied to them as the reactor 10 components are fastened together. Orientating all of the ribbed supports 140 in the same direction helps ensure the flat surface 170 of the ribs 185 form channels and do not damage the porous substrate. Also as a result of the orientation of the ribbed support materials 140 and the alternating layers of sheets of porous substrate 150 with sheets of ribbed support material 140, a gap is created between porous substrate materials 150 (and between the porous substrate materials 150 and the side plates 21). The gap can prevent or alleviate cross-flow between adjacent sheets of porous substrate 150 as well as prevent or alleviate contact between the porous substrate 150 and side plates 21 of the reactor 10.

FIG. 7 is an end view of an alternative configuration of the internal structure of a reactor, and which can be used with reactors such as that shown in FIG. 3. In some embodiments, when a plurality of ribbed supports 140 and porous substrates 150 are used, a nonporous spacer/gasket 155 can be incorporated between the integrated gaskets 135 that do not have porous substrate 150 between them. In some embodiments, the additional nonporous spacer/gaskets 155 shown in FIG. 7 are of approximately the same thickness as the porous substrate 150. This thickness is chosen to provide a uniform thickness across the entire ribbed spacer section 30, resulting in more uniform pressure and sealing when the side plates 21 are fastened together compared to when they are not used. In some embodiments, the nonporous spacer/gasket 155 is composed of a nonporous substance, or is composed of a substance treated in such a way as to render it nonporous, or is composed of any substance that ensures creation of a seal to prevent or alleviate gas flow out of the evaporation chamber 110 and liquid flow out of the liquid-contacting chamber 130, as a leak, or by wicking through the nonporous spacer/gasket 155. In some embodiments, the nonporous spacer/gasket 155 does not, however, impede liquid flow out of the liquid-contacting chamber 130 through the porous substrate 150. For example, as shown in FIG. 8, the porous substrate extends from the bottom to the top of the ribbed support material 140 but portions of the porous substrate, specifically between gaskets 135a, 135b and 135e, 135f are coated with latex to create a nonporous spacer. In the embodiment of FIG. 8, the inner structure of the reactor includes 5 pieces (three ribbed support materials 140 and two, partially latex-coated porous substrate materials 150), as compared to the embodiment of FIG. 7, which comprises 9 pieces (three ribbed support materials 140, two porous substrate materials 150, and four non-porous spacers 155.

FIG. 10 is a cross-section view taken along the dashed line "I-I" in FIG. 9, showing a side view of the inner structure of the reactor of FIG. 3. As is apparent from FIG. 10, the flat surface 170 of the ribbed support material 140 is discontinuous, creating channels between the flat surfaces 170. Consequently, both sides of the porous substrate 150 are accessible to gas flowing through the reactor—via the channels created by the spaces between the flat surfaces 170 on one side of the ribbed support material 140 and via the channels created by the raised-apart ribs on the opposite side of the ribbed support material 140.

FIG. 11 is an exploded end view of an alternative configuration of the inner structure of a PFR, such as that shown in FIG. 3. According to the embodiment of FIG. 11, the raised ribs of one sheet of ribbed support material 140 are not in register, i.e. do not exactly align, with the raised ribs of an adjacent sheet of ribbed support material 140. Nonetheless, the flat surfaces 170 prevent or alleviate the raised ribs from damaging the porous substrate 150.

Figure 12:
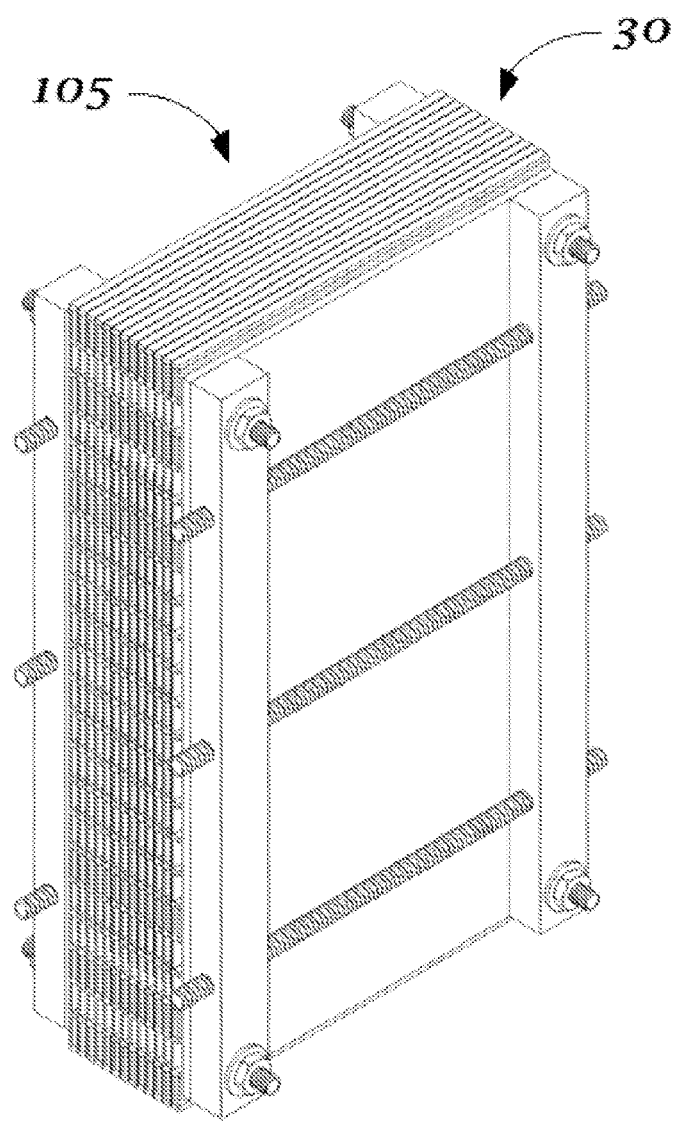
FIG. 12 is a perspective view of a scaled-up embodiment of a multiphase PFR similar to that of FIG. 3, wherein the end plates of the reactor are intentionally not shown to illustrate the internal ribbed support section.

FIG. 12 shows an embodiment of a "scale-up" version of the reactor of FIG. 3. In the illustrated embodiment of FIG. 12, the end plates have been intentionally left out of the illustration of the PFR 105 to show a larger ribbed support section 30 which contains a plurality of porous substrates 150 and ribbed supports 140. Generally speaking, the depth (number of porous substrates) and width of the PFR 105 are driven by economics—for example the costs of materials for the reactor components and putting the components together, the cost of reactant materials, the costs of flowing liquid into the liquid-contacting region versus the value of the product. Theoretically, for a very high value product and very low cost of materials, the width of the PFR could be very long, for example 1 meter or more, or for example 5 meters or more, or for example 10 meters or more. The depth of the chambers is similarly only theoretically limited by cost, and therefore the chamber could contain at least 2 porous substrates or more, or for example 10 porous substrates or more, or for example 25 porous substrates or more, or for example 50 substrates or more, or for example 100 substrates or more.

Figure 13:
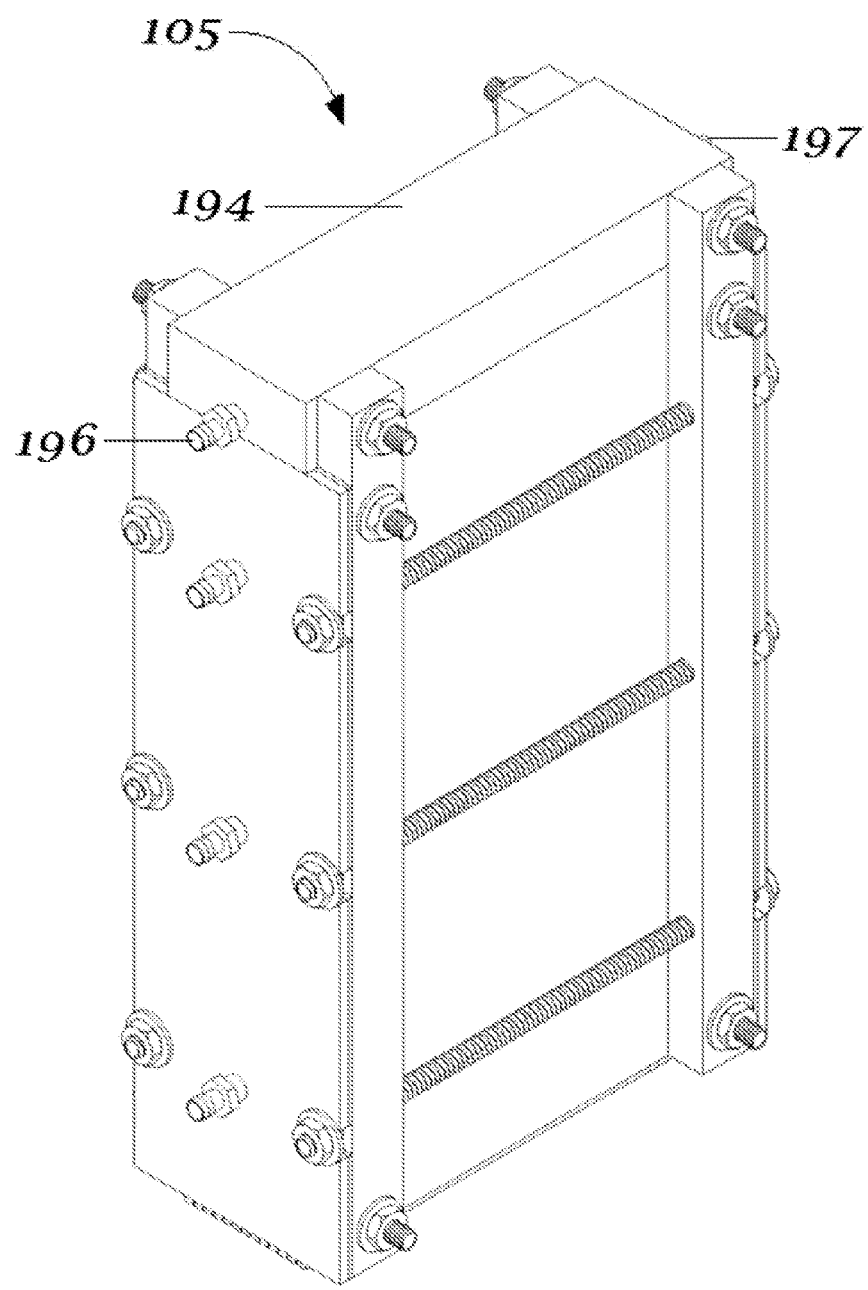
FIG. 13 is a perspective view of another embodiment of a multiphase porous flow similar to that of FIG. 12, wherein an integrated circulating heat supply has been added.

Increasing the depth or the width of the PFR may require removing more water from the liquid-collection chamber. In some embodiments using evaporation as a mechanism for removing liquid an extra housing component which provides heat to the liquid-collection chamber may be beneficial. For reference, FIG. 13 illustrates the reactor in FIG. 12 with the end plates on the reactor. In addition this embodiment of FIG. 13 includes a housing component 194 which provides heat to the liquid-collection chamber. The housing component for heating has ports 196 and 197 which enable the addition and removal of heated liquid from the heating unit. The heated liquid heats the heating unit which is in direct communication with the liquid-collection chamber thereby heating the liquid-collection chamber. Heat may be brought to the housing component by any number of different means including but not limited to hot gases such as from a gasifier, steam, hot water or hot oil. The heat may be generated from within the housing component by a number of different means including but not limited to heat generated using electricity or by combustion.

On the other hand, generally speaking, the maximum height of an upflow PFR (more specifically the maximum liquid flow path length 180 illustrated in FIG. 6), such as exemplified in FIGS. 3-13, can be calculated by a person of ordinary skill using equations defining porous flow. In some embodiments, the maximum liquid flow path length is not used but rather a shorter length is chosen such that a sufficient flow of liquid is provided along the liquid porous flow path 180 to maintain the activity of the reaction facilitator. In another example, the liquid porous flow path 180 length would be such that liquid flow reaching the evaporation chamber 110 would result in a desired amount of product reaching the liquid-collection chamber 110 in a specified amount of time. In practice, in some embodiments, the length of the liquid flow path 180 is expected to be 110 cm or less. In some embodiments, the length of the liquid flow path 180 is expected to be 100 cm or less, 95 cm or less, 90 cm or less, 85 cm or less, 80 cm or less, 75 cm or less, 70 cm or less, 65 cm or less, 60 cm or less, 55 cm or less, 50 cm or less, 45 cm or less, 40 cm or less, 35 cm or less, 30 cm or less, 25 cm or less, 20 cm or less, 15 cm or less, or 10 cm or less.

Figure 14:
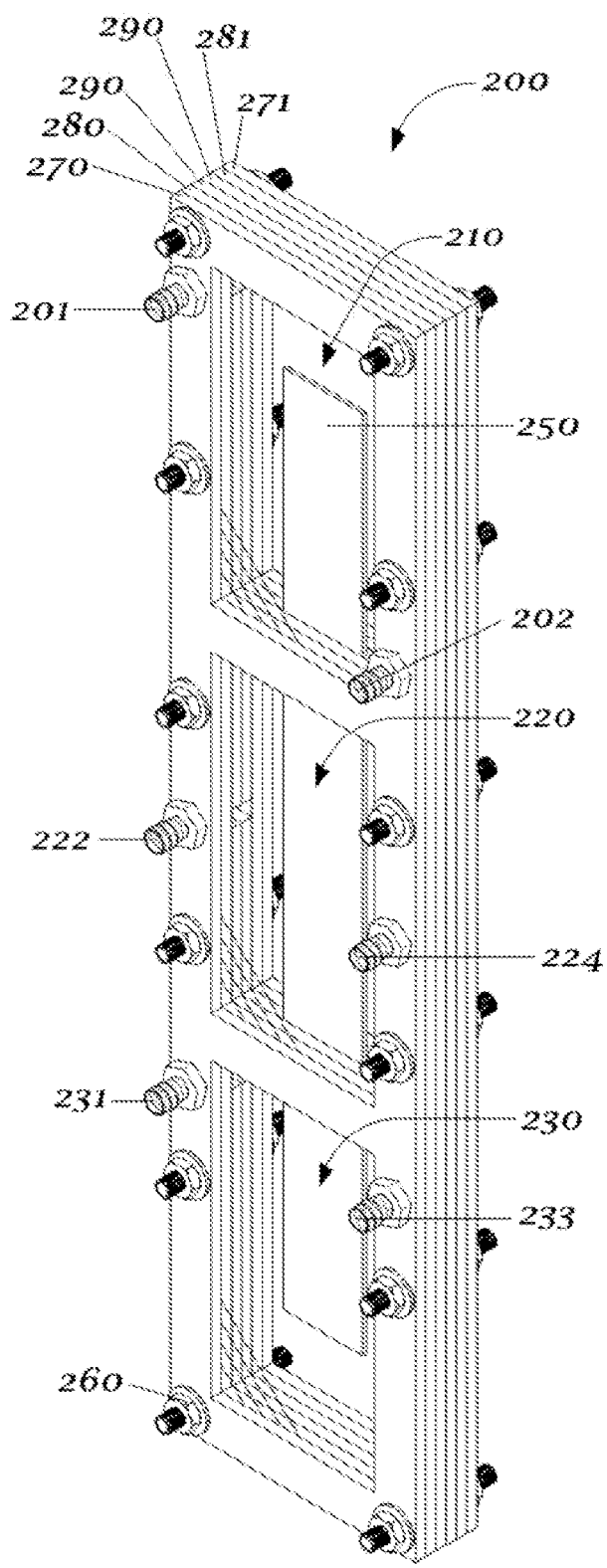
FIG. 14 is a perspective view of another embodiment of a multiphase PFR.
Figure 15:
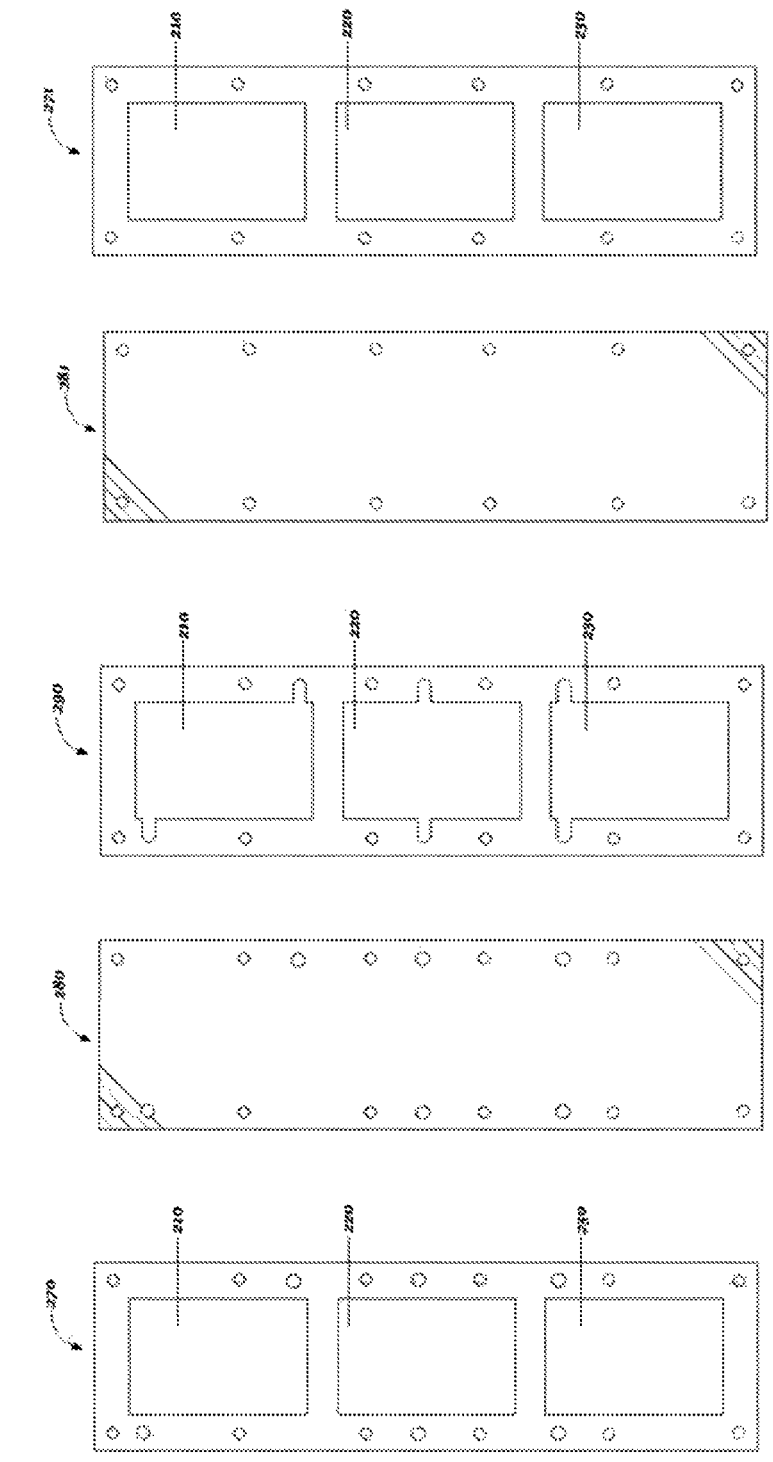
FIG. 15 is an illustration of certain components making up the reactor of the embodiment of FIG. 14

FIGS. 14-28 are additional embodiments of PFRs consistent with the disclosure. FIG. 14 is a perspective view of a three-chamber PFR 200 suitable for running photosynthetic or other reactions or processes requiring light. FIG. 15 illustrates the components of the reactor, in their respective order: side plate 270, clear plate 280, a pair of seals 290, clear plate 281 and side plate 271. When assembled, and run in the upflow mode, openings in the side plates 270, 271 and corresponding openings in the seals 290 align to define three chambers—a liquid-contacting chamber 230, a gas-contacting chamber 220, and an evaporation chamber 210. A porous substrate material 250 extends from within the liquid-contacting chamber 230 through the gas-contacting chamber 220 into the liquid-collection chamber 210. Various nuts and bolts 260 are used to releasably fasten the side plates 270, 271, clear plates 280, 281 and seals 290 together. Port 231 enables delivery of liquid and port 233 allows for removal of gas displaced by the liquid. Port 222 allows for the delivery of gas and port 224 enables the removal of gas. Port 201 permits the delivery of gas and/or liquid and port 202 permits the removal of gas and/or liquid. As with the embodiment described in FIG. 3, numerous design changes are possible, including many correlating to the various modifications suggested in connection with the reactor 10.

Figure 16:
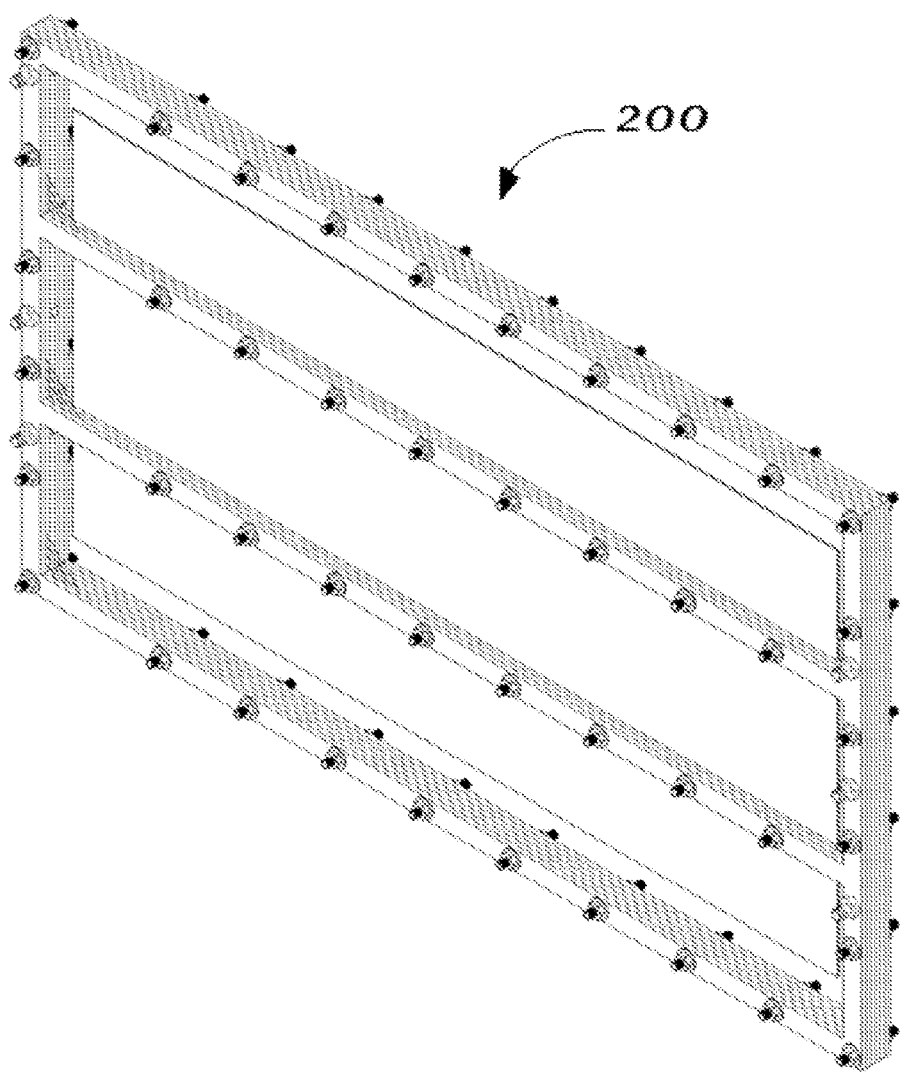
FIG. 16 is a perspective view of a scaled-up embodiment of a multiphase PFR similar to that of FIG. 14.

FIG. 16 is an embodiment of a "scale-up" version of the reactor of FIG. 15. In contrast to the reactor embodiment of FIG. 3, because the reactor 200 of FIGS. 15 and 16 are designed to operate photosynthetic reactions or other light-requiring processes, the depth of the reactors is limited by the ability to expose the relevant internal portions of the reactor (generally the gas-contacting region of the porous substrate) to light. On the other hand, generally speaking, the width of the PFR 200 are driven by economics—for example the costs of materials for the reactor components and putting the components together, the cost of reactant materials, the costs of flowing liquid into the liquid-contacting region versus the value of the product. Theoretically, for a very high value product and very low cost of materials, the width of the reactor could be very wide, for example 1 meter or more, or for example 5 meters or more, or for example 10 meters or more. Regarding the height of the reactor, as with the reactor embodiment of FIG. 3, and as with upflow PFRs generally, the maximum height of a PFR (more specifically the liquid flow path length 180 maximum) can be calculated by a person of ordinary skill using equations defining porous flow.

Figure 17:
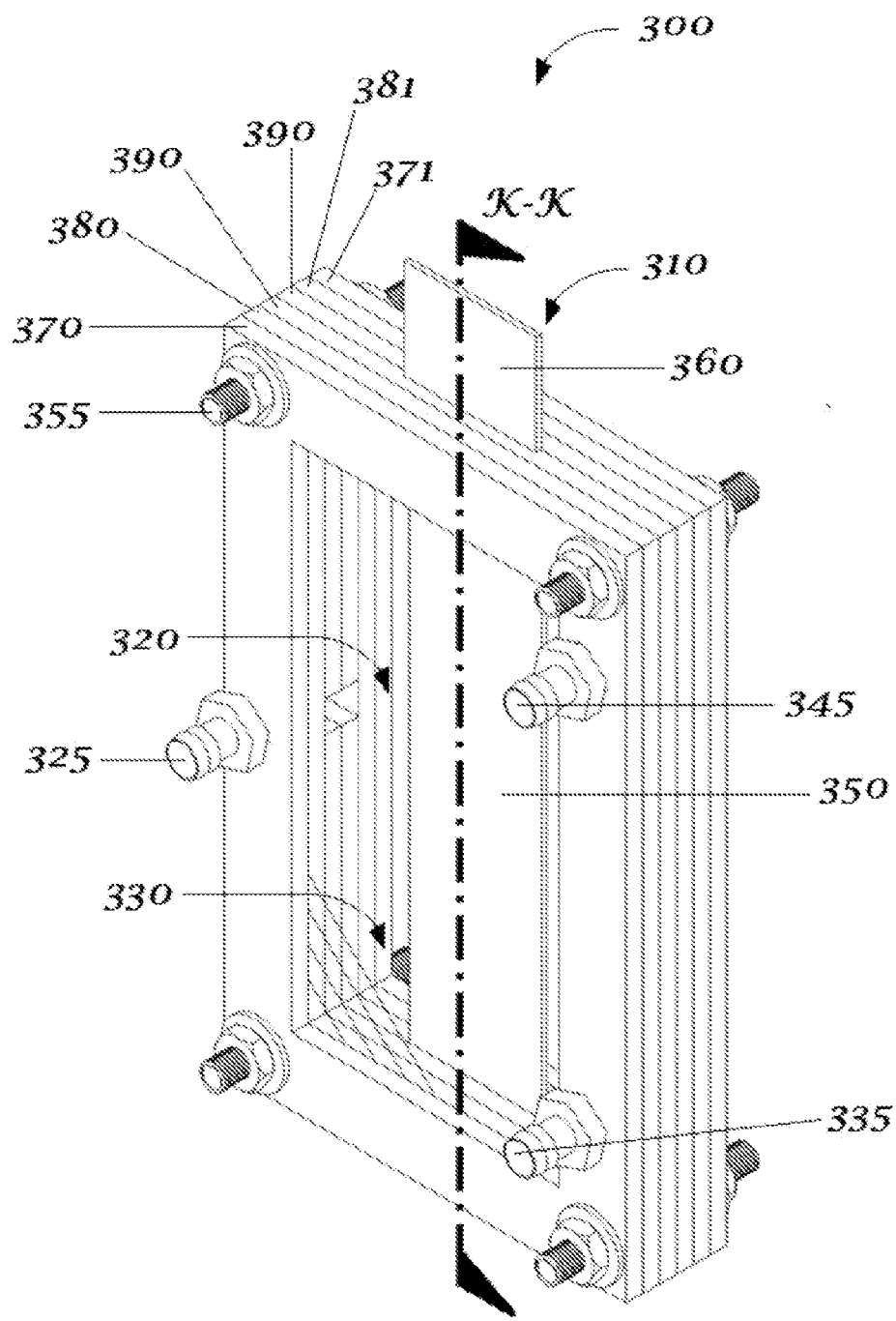
FIG. 17 is a perspective view of another embodiment of a multiphase PFR.
Figure 18:
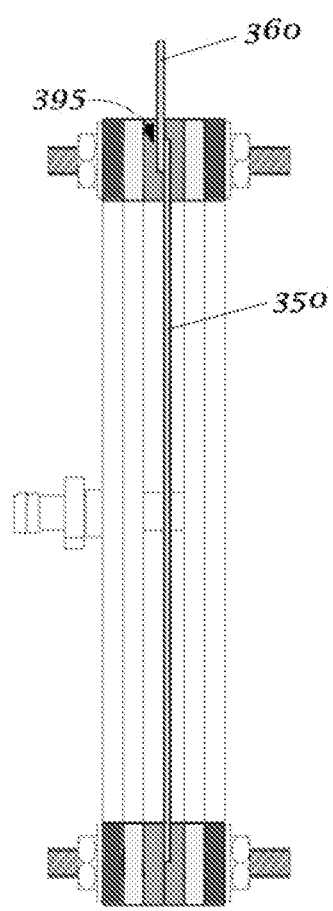
FIG. 18 is a side end cut view of the multiphase PFR of FIG. 15 taken along the line in FIG. 17.

FIG. 17 is a perspective view of an embodiment of a two-chamber PFR, which chambers are separated by a seal 390, and a first chamber (corresponding to the gas-contacting region 320 and liquid-contacting region 330) is enclosed within the housing (formed by fastening together the side plates 370, 371 and clear plates 380, 381) and the second chamber (corresponding to the liquid-collection region 310) is outside the housing. FIG. 18 is a cross section view of FIG. 17 taken along the dashed line "K-K". As illustrated in FIG. 18, a first porous substrate material 350 extends from within the liquid-contacting region 330 through the gas-contacting region 320 and overlaps 395 a second removable porous substrate 360 which extends into the liquid-collection chamber 310. Various nuts and bolts 355 are used to releasably fasten the side plates 370, 371, clear plates 380, 381 and seals 390 together. Port 335 enables delivery of liquid, port 325 allows for the delivery of gas, and port 345 enables the removal of gas. As with the embodiments described in FIG. 3 and FIG. 16, numerous design changes are possible, including many correlating to the various modifications suggested in connection with reactors 10 and 200.

Figure 19:
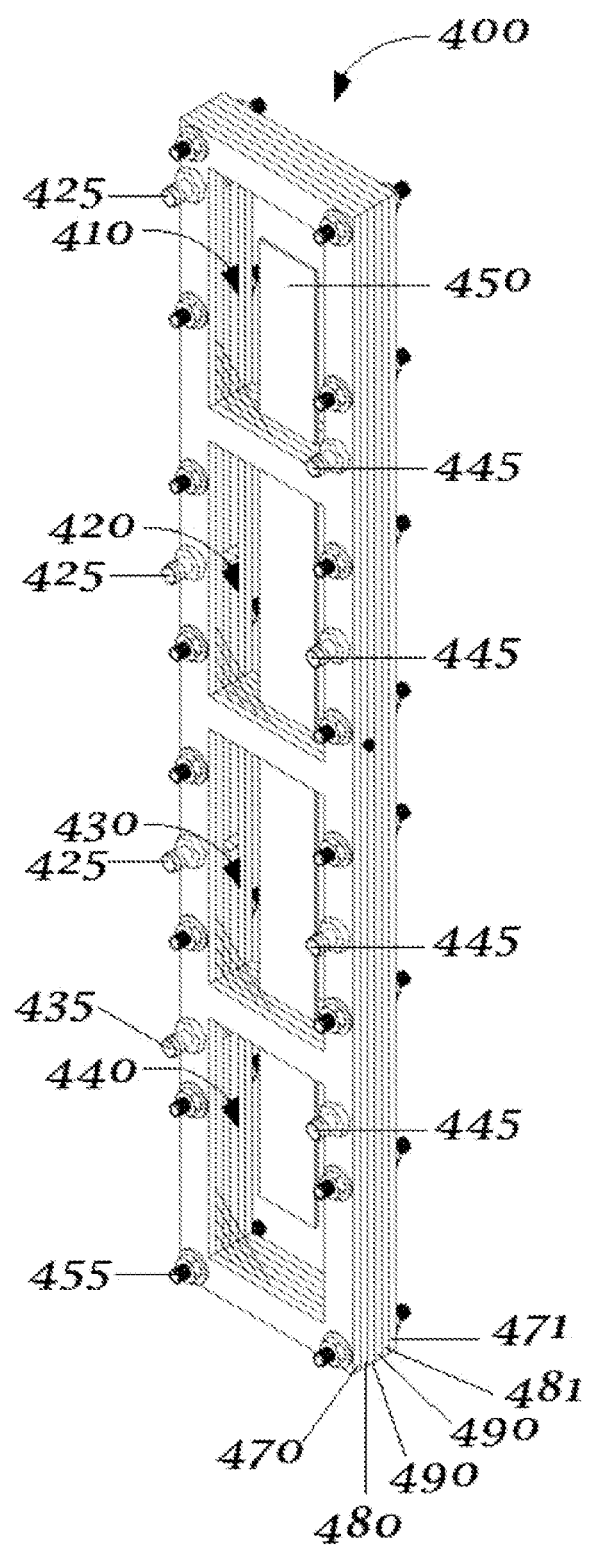
FIG. 19 is a perspective view of another embodiment of a multiphase PFR.

FIG. 19 is a perspective view of an embodiment of a four-chamber PFR 400 having a porous substrate 450 extended from a liquid-contacting chamber 440, spanning a first gas-contacting chamber 430 and a second gas-contacting chamber 420, and then extending into a liquid-collection chamber 410. Port 435 enables delivery of liquid, ports 425 allows for the delivery of gas, and ports 445 enable the removal of gas. Various nuts and bolts 455 are used to releasably fasten the side plates 470, 471, clear plates 480, 481 and seals 490 together. The gas-contacting chambers 430 and 420 can be two distinct regions, wherein the porous substrate is loaded with a different overall set of reaction facilitators in the first gas-contacting chamber 430 as compared to the second gas-contacting chamber 420. In some embodiments, the porous substrate 450 in the first gas-contacting chamber 430 is loaded with the same reaction facilitator(s) as the porous substrate 450 in the second gas-contacting chamber 420. In some embodiments, the porous substrate 450 in the first gas-contacting chamber 430 is loaded with some of the same reaction facilitator(s) as the porous substrate 450 in the second gas-contacting chamber 420. In some embodiments, the porous substrate 450 in the first gas-contacting chamber 430 is loaded with different reaction facilitators as are loaded on the porous substrate 450 in the second gas-contacting chamber 420.

Figure 20:
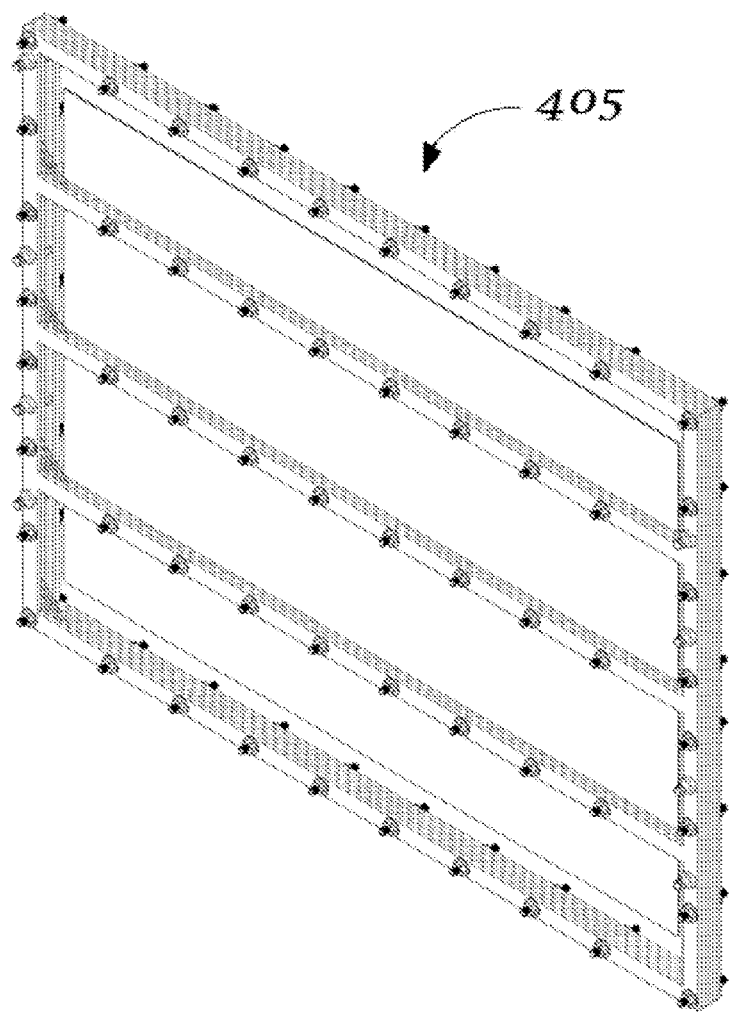
FIG. 20 is a perspective view of a scaled-up embodiment of a multiphase PFR similar to that of FIG. 19.

FIG. 20 is a perspective view of a "scale up" version of the reactor of FIG. 19, wherein at least the width of the reactor 405 is elongated as compared to the embodiment of FIG. 19.

Figure 21:
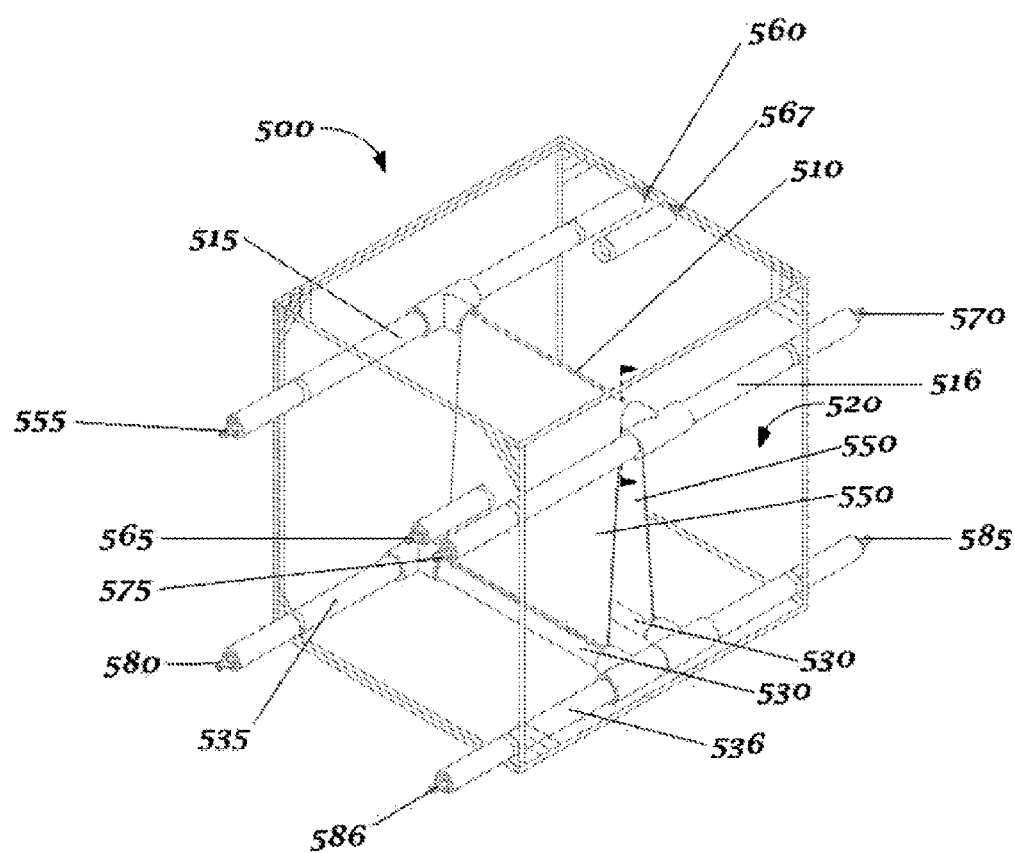
FIG. 21 is a perspective view of another embodiment of a multiphase PFR.

FIG. 21 is a perspective view of another embodiment of a three-chamber PFR 500 suitable for use with photosynthetic or other reactions or processes requiring light. The reactor 500 includes an evaporation chamber 510, a gas-contacting chamber 520, a liquid-contacting chamber 530, two sheets of porous substrate material 550, each extending from within the liquid-contacting chamber 530 through the gas-contacting chamber 520 into the liquid collecting chamber 510. In some embodiments, the reactor may contain only a single sheet of porous substrate material 550 that extends from one well of the liquid-contacting chamber 530 through the gas-contacting chamber 520 to and through the liquid-collection chamber 510 back through the gas-contacting chamber 520 and into a second well of the liquid-contacting chamber 530. Gas is delivered to the gas-contacting chamber by a gas port 565 and removed from the gas-contacting chamber by a port 567. In some embodiments in which the reactor is used for photosynthetic reactions or other reactions or processes requiring light, the porous substrate material 550 is oriented at any angle of inclination which permits light shining into the reactor to contact an entire surface of the porous substrate material 550 within the gas-contacting chamber 520. For example, the angle of inclination can be from about 0 to about 90°.

The reactor 500 also includes: first and second liquid reservoirs 535, 536; a gas distribution tube 515; a gas collection tube 516; a liquid entry port 580, liquid exit port 586, and a gas exit port 585 associated with the liquid-contacting chamber 530; a gas entry port 565 and corresponding gas exit port 575 associated with the gas-contacting chamber; and, a first pair of ports 555, 560 and a second pair of ports 575, 570 associated with the liquid-collection chamber 510. The first and second liquid reservoirs 535, 536 are in fluid communication with the liquid-contacting chamber 530. The gas distribution tube 515 and the gas collection tube 516 are in fluid communication with the liquid-collection chamber 510. The liquid entry port 580 is in fluid communication with the liquid reservoir 535 and the liquid exit port 586 and gas exit port 585 are in fluid communication with the liquid reservoir 536 such that liquid added through port 580 flows from the first liquid reservoir 535 through a well of the liquid-contacting chamber 530 where the substrate 550 removes a portion of the liquid by porous flow/wicking action through the gas-contacting region 520 into the liquid-collection chamber 510. The remaining liquid moves through another well of the liquid-contacting chamber 530 to a second liquid reservoir 536 where it is removed through a port 586 to be recycled back to the first liquid reservoir 535. Gas, displaced by the liquid, can be removed through port 585. Ports 555 and 560 are in fluid communication with the gas distribution tube 515 and ports 570, 575 are in fluid communication with the gas collection tube 516 such that gas is supplied to the liquid-collection chamber 510 through a port 555 in gas distribution tube 515 and when it leaves the liquid-collection chamber 510, is collected in a gas collection tube 516 and exits the flow reactor 500 through port 570. In some embodiments, the liquid-collection chamber 510 is oriented at an angle sufficient to drain liquid from the chamber 510 into the gas collection tube 516. Ports 565, 567 are in fluid communication with the gas-contacting chamber for circulating gas into and out of the gas-contacting chamber.

Figure 23:
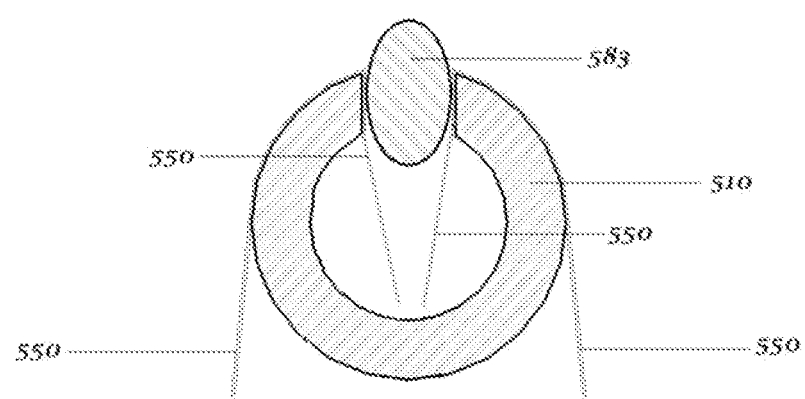
FIG. 23 is an end cut view of the evaporation chamber of the multiphase PFR of FIG. 21 showing a resealable fastener.

In some embodiments, the paper 550 is held in the liquid-contacting chamber 530 and the liquid-collection chamber 510 by a releasable means for securing 581 the porous substrate 550 into the chamber 510 as illustrated in FIG. 23. FIG. 23 is a cross section expanded end view cut of an embodiment of a releasable securing system for holding the porous substrate 550 within the liquid-collection chamber 510. According to FIG. 23, a removable rubber cord or tubing 583 is pressed into the opening in the tube 510 such that the porous substrate 550 is releasably pressed against the walls of the opening and held in place. Other methods of supporting the porous substrate 550 within the liquid-collection chamber 510 can be envisioned including but not limited to hose clamps or internal pressure seals.

Figure 22:
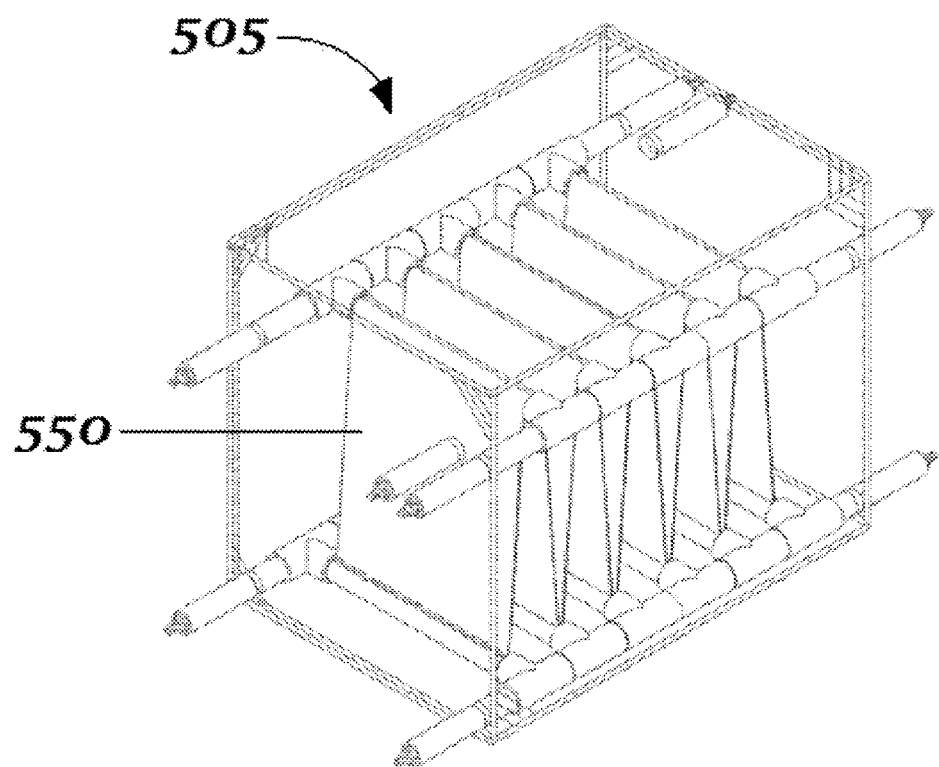
FIG. 22 is a perspective view of a scaled-up embodiment of a multiphase porous flow similar to that of FIG. 21.

FIG. 22 is a perspective view of another embodiment of a PFR 505, particularly a "scale-up" version of the reactor of FIG. 21. As shown in FIG. 22, orienting the porous substrate material 550 at an angle permits this reactor style to be scaled-up, i.e. to be lengthened indefinitely (although practically only as long as economics permits) and still run photosynthetic reactions. While this embodiment has been described in connection with a three-chamber embodiment, a person of skill in the art can envision adapting this embodiment to a multi-chamber device, for example the liquid-contacting chamber can be divided into multiple liquid-contacting chambers, i.e. in some embodiments the liquid chambers 530 may not all be in fluid communication with one another.

Figure 24:
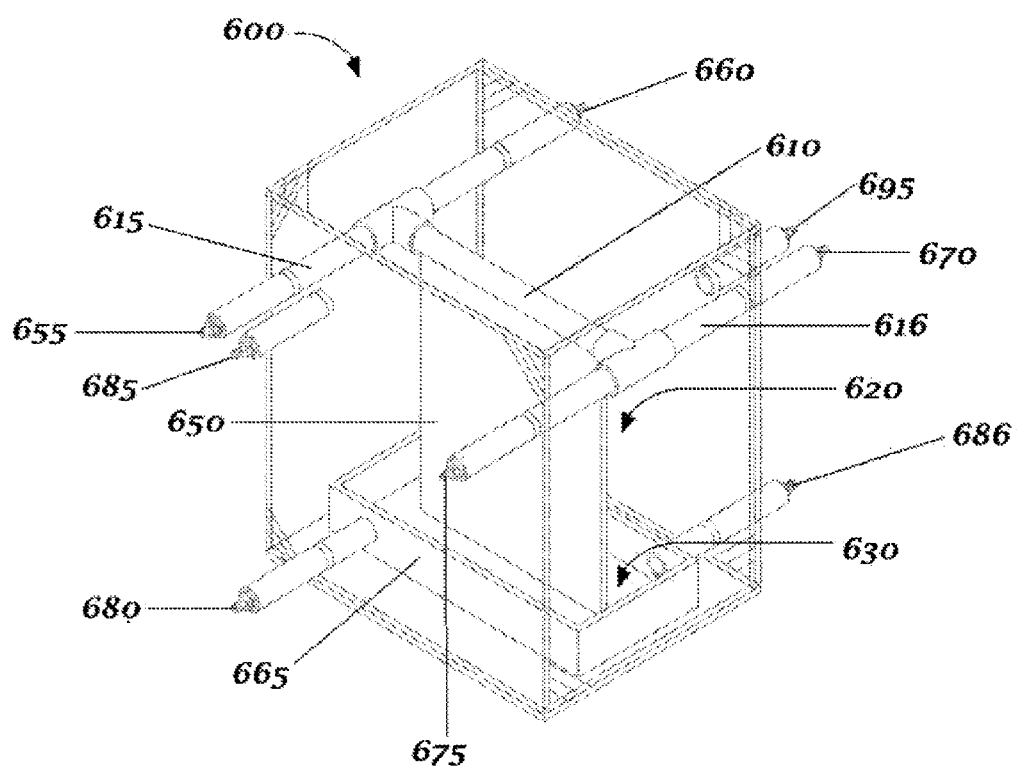
FIG. 24 is a perspective view of another embodiment of a multiphase PFR.
Figure 25:
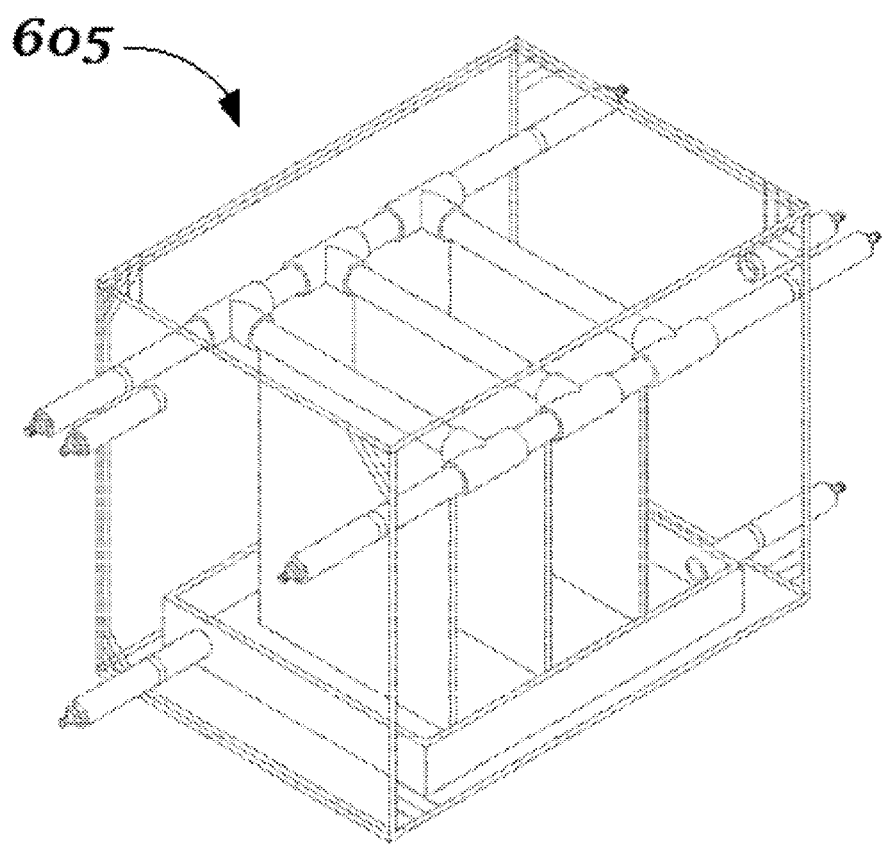
FIG. 25 is a perspective view of a scaled-up embodiment of a multiphase PFR similar to that of FIG. 24.

FIG. 24 is a perspective view of an embodiment of a two-chamber PFR 600 suitable for use with photosynthetic reactions or other light-requiring processes. In this embodiment, the porous substrate 650 moves liquid from the liquid-contacting region 630 into the gas-contacting region 620 which are co-located in one chamber of the reactor 600, and the liquid-collection chamber 610 is a distinct second chamber in the reactor 600. The reactor 600 also includes a liquid reservoir 665, a gas distribution tube 615, a gas collection tube 616, a liquid entry port 680, and a corresponding liquid exit port 686. Gas is added to the gas-contacting region by a port 685 and removed by a port 695. The liquid-collection chamber has a gas entry port 655 and corresponding gas exit port 670, a liquid entry port 660 and corresponding liquid exit port 675. The gas distribution tube 615 and the gas collection tube 616 are in fluid communication with the liquid-collection chamber 610. FIG. 25 is a perspective view of a "scale-up" version 605 of the two-chamber PFR 600 of FIG. 24.

Figure 26:
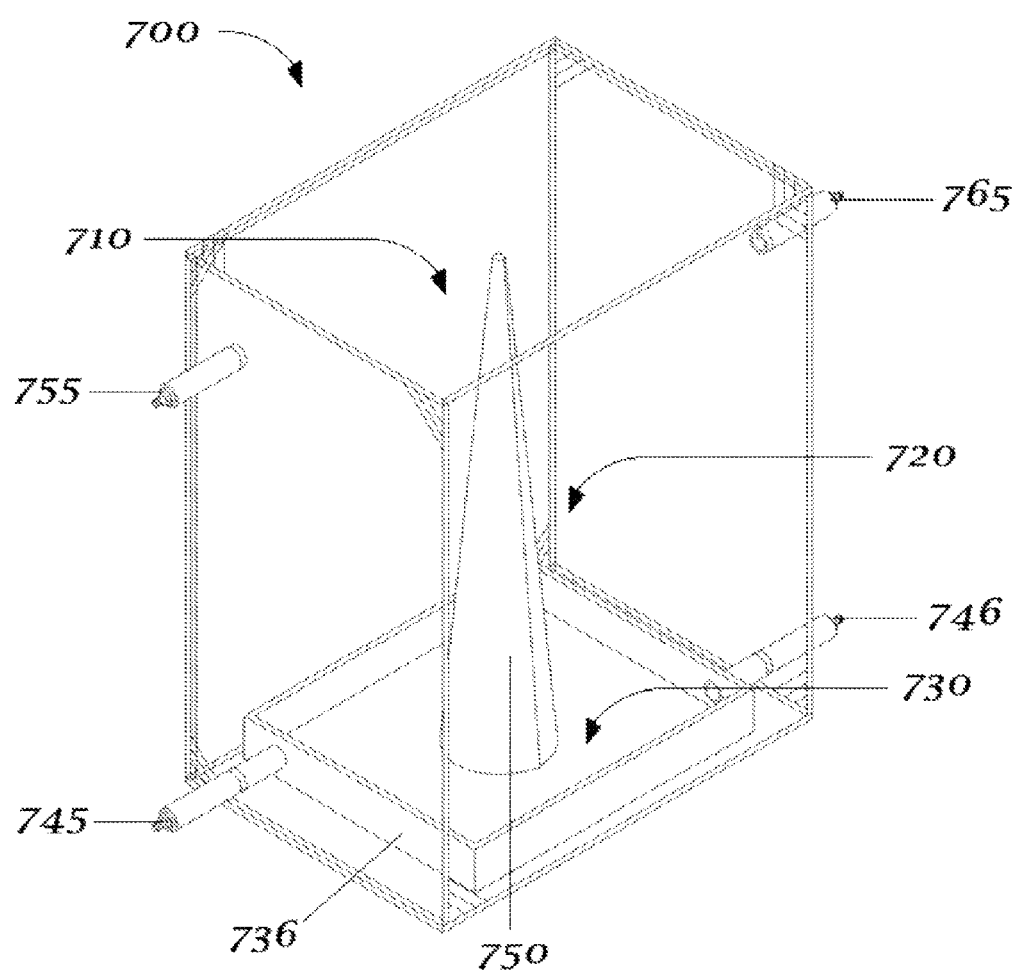
FIG. 26 is a perspective view of another embodiment of a multiphase PFR.
Figure 27:
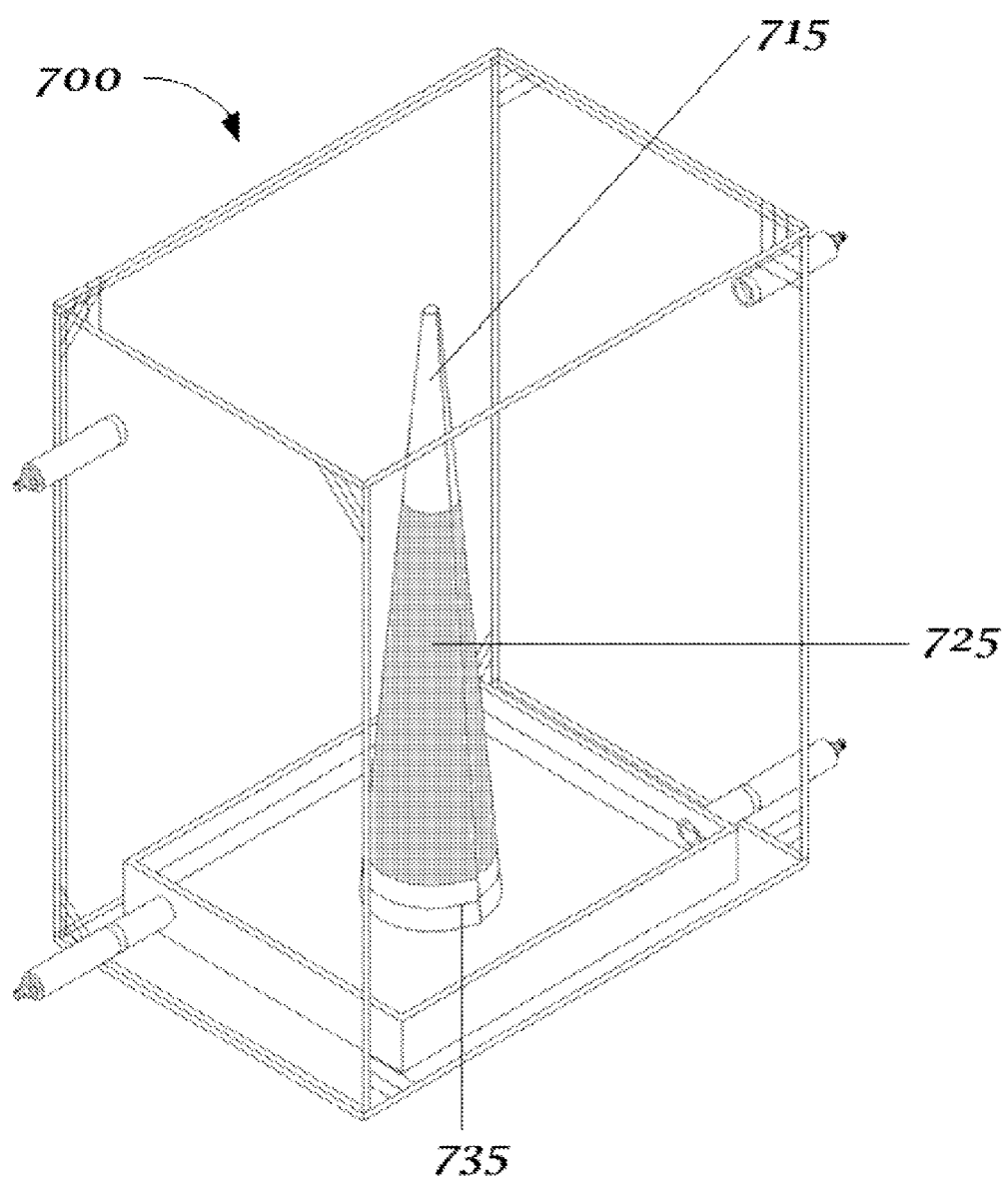
FIG. 27 is a perspective view of the reactor of FIG. 26 with the gas-contacting region identified by shading.

FIG. 26 is a perspective view of an embodiment of a one-chamber PFR 700 suitable for use with photosynthetic reactions or other light-requiring processes. In this embodiment, the liquid-contacting region 730, the gas-contacting region 720, and the liquid-collection region 710 are all co-located in the reactor 700. In the embodiment of FIG. 26, the porous substrate 750 is folded into a cone shape, providing a self-supporting structure. Liquid is added to the liquid reservoir 736 through a port 745. Liquid is removed from the liquid reservoir through a port 746. Gas is added to the PFR 700 through a port 755 and removed through a port 765. FIG. 27 is another view of the same one-chamber PFR 700 of FIG. 26, wherein shading and lines are provided to better illustrate the regions of the reactor 700. Specifically, line 735 delineates the upper boundary of the liquid-contacting region, the shaded region 725 delineates the gas-contacting region, and the non-shaded region above the gas-contacting region 715 delineates the liquid-collection region. In some embodiments, reaction facilitators are loaded onto or into the porous substrate within the shaded region 725.

Figure 28:
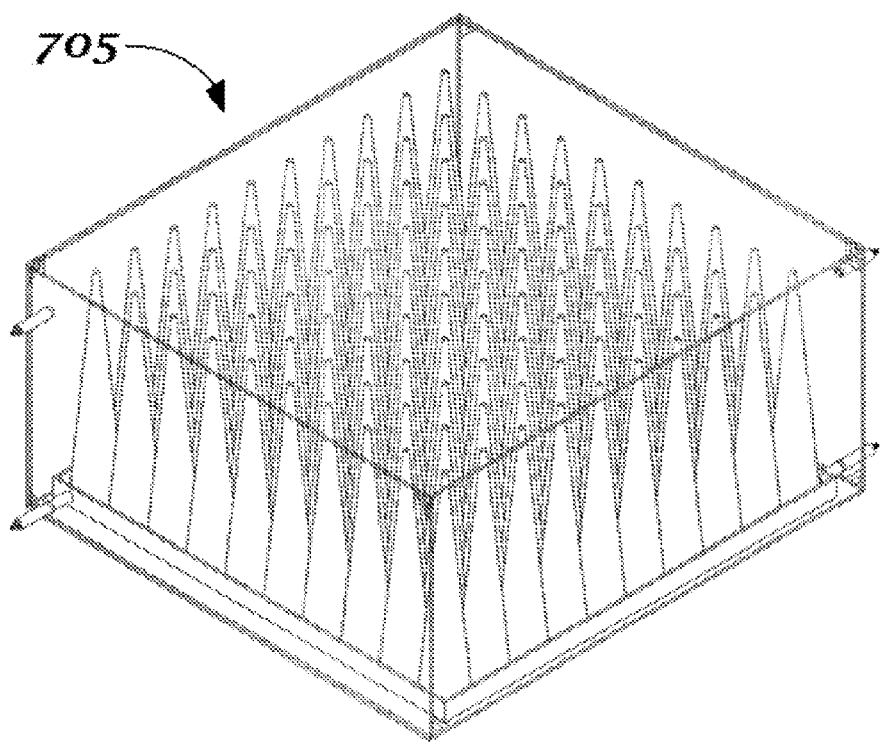
FIG. 28 is a perspective view of a scaled-up version of a reactor similar to FIG. 26.

FIG. 28 is a perspective view of another embodiment of a PFR 705, particularly a "scale-up" version of the reactor of FIG. 26. The length and width of the reactor, as well as the height of the porous substrate are limited by the same considerations discussed in connection with other embodiments of upflow PFRs.

Figure 29:
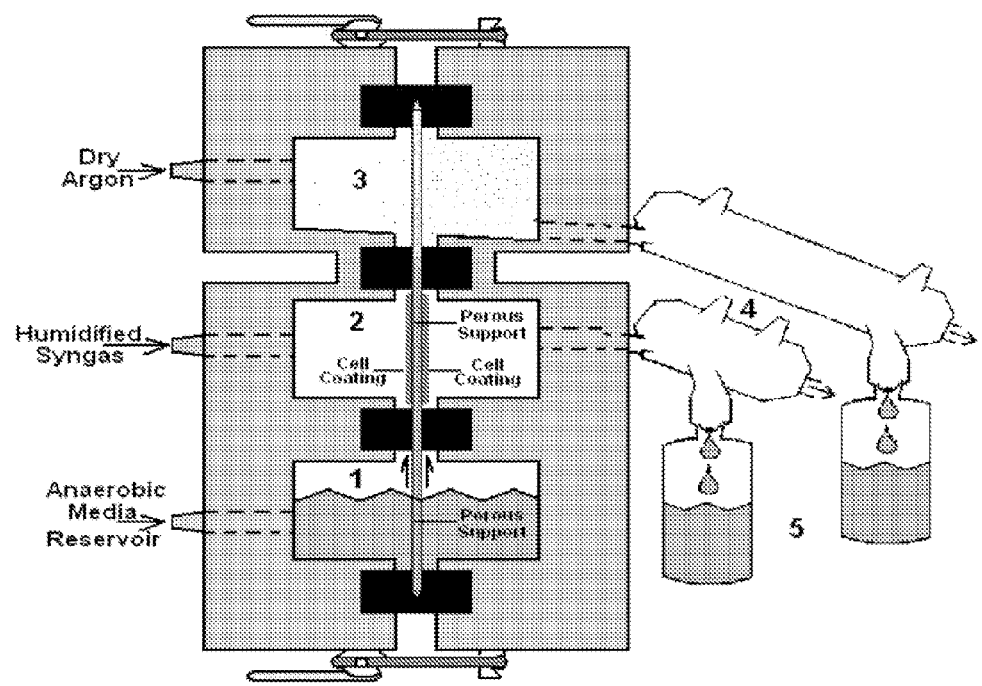
FIG. 29 is a perspective view of a bench-scale embodiment of a PFR.

FIG. 29 illustrates the initial porous flow device, developed to study cells immobilized on a surface, specifically, *Clostridium ljungdahlii*. The device is a bench-top device including three regions in three distinct chambers. Both the gas-contacting chamber and the evaporation chamber has an inlet and outlet to permit the flow of gas through each chamber, the outlets are fluidly connected condensers for condensing gas flowing out of the chambers.

A number of PFR embodiments have been described. However a person of skill can readily appreciate from a review of this specification and figures that other embodiments are also possible, and thereby are also within scope of the invention.

In one such example, as a person of skill can appreciate by reading this specification, many of the described "upflow" devices can be run as "downflow" devices or can be reconfigured to run as downflow devices (and vice versa). For example, the devices of FIGS. 21, 24 and 25 could operate by liquid moving in the opposite direction as previously described. In a reconfigured embodiment of FIG. 21, the pipes 510, 515, 516 could supply liquid to the porous substrate and the liquid could be recovered in pipes 530, 535, 536. Alternatively, or in combination, the liquid could be evaporated. Similarly, in a reconfigured embodiment of Figs. FIGS. 24 and 25, the liquid-collection region 610 would be the liquid-contacting region, and the liquid-contacting region 630 would be the liquid-collection region. Media would be supplied through the pipes and ports connected to the now liquid-contacting region 610 and removed from the now liquid-collection region 630 through the ports and pipes associated with the liquid-collection region 630. In fact, Example 6 was run on the device of FIG. 24 in the downflow mode, Example 8 was run on the device of FIG. 25 in the downflow mode, and Example 9 is run on a device according to FIGS. 1, 24 and/or 25 in the downflow mode. For clarity, it should be stated that in the downflow mode the porous substrate does not have to be in physical contact with the liquid in the liquid-collection region.

As another example, as a person of skill may appreciate, possible dimensions of gravity-assist devices may differ from devices where porous flow is generally defined in an upward direction. For example, in the upward flow devices, gravity is a constraint on the vertical length of the device, which is not the case in a gravity-assist device where porous flow would be generally described as downward. On the other hand, a pressure gradient that may develop due to liquid loading may impact the operation of a gravity-assist device but this constraint can be addressed by modifications to the system such as inlet flow control to prevent over saturation of the porous flow substrate. It is also conceived that the rate at which liquid exits the porous substrate in the liquid-collection region could constrain the rate of porous flow through the porous substrate and the exit of liquid from the liquid-collection region in some embodiments should be sustained such that the collection of liquid does not unnecessarily impede liquid flow through the porous substrate.

IV. Methods

PFRs, generally, operate according to the same basic principles. For example, chemical and biological transformations are accomplished by: adding liquid, which may contain reactants (and/or nutrients for reaction facilitators when applicable or desirable), to the liquid-contacting region(s); flowing gas, which may also contain reactants, into the gas-contacting region(s); and maintaining flow of the liquid through the gas-contacting region by removing liquid from the system, such as by collecting the liquid directly as it flows out of the porous substrate, or by collecting the liquid by evaporating it off of the porous substrate. When liquid in the liquid-contacting region contacts the porous substrate, it flows through the substrate in whole or in part due to porous flow (capillary action) through the gas-contacting region and may be assisted for example by gravity and/or added pressure. The continuous flow of liquid through the porous substrate (which may be intermittent) is maintained provided liquid is present in the liquid-contacting region and liquid is continuously (e.g. intermittently) removed from the porous substrate in the liquid-collection region and then the liquid is removed from the liquid-collection region.

Chemical or biological transformations occur in the gas-contacting region, where the catalysts, enzymes, and/or microorganisms are present on and/or within the porous substrate facilitate reactions between the liquid and/or gas reactants. Products may be partitioned into the gas phase, the liquid phase or both. Products partitioned into the gas phase may be removed from the gas-contacting region, for example with gas being circulated into and out of the gas-contacting region. Product portioned into the liquid phase may travel into the liquid-collection region by porous flow or may travel outside of the porous substrate with the liquid, which flows out of the porous substrate due to for example porous flow, gravity and/or added pressure. The liquid, with or without product, may be recycled back into the system.

Evaporation of liquid, which may be at least partially driven by the flow of gas through the liquid-collection region, enables a continuous flow of liquid in the reactor via the porous substrate (so long as, for example, liquid is present in the liquid-contacting region and the porous substrate and the reaction facilitators thereon and/or therein maintain porous flow functionality). If the product (which has travelled into the liquid-collection region) has an appropriate vapor pressure and liquid is being evaporated in the liquid-collection region, it may be collected as the gas stream flows out of the liquid-collection region along with the gas flowing through the liquid-collection region to encourage evaporation. If the product instead (or in addition) crystallizes on or in the porous substrate when the liquid evaporates in the case of liquid-collection regions which are evaporating liquid, a different or similar additional liquid may be periodically streamed through the liquid-collection region. The crystallized product dissolves in the liquid and may be collected in the liquid stream as it leaves the liquid-collection region. Alternatively, or in addition, product may be recovered by removing the porous substrate from the reactor. In some embodiments, for example as shown in FIGS. 17 and 18, product is recovered by removing only the portion of porous substrate in the liquid-collection region from the reactor. In some embodiments, therefore, rather than periodically flowing liquid through the liquid-collection region, the porous substrate, which constitutes the liquid-collection region, can simply be removed and replaced by another piece of porous substrate material (or the same piece of porous substrate material may be reused after removing products and other substances, as desired, from the porous substrate material).

Figure 30:
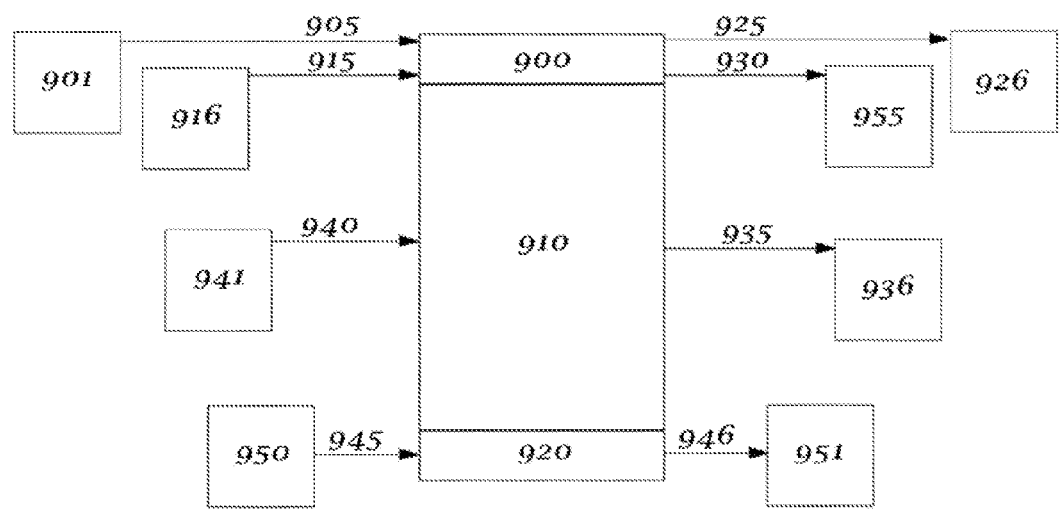
FIG. 30 is a process flow diagram for an embodiment of the use of a PFR.

FIG. 30 is a process flow diagram illustrating several embodiments of a generalized operation of a PFR. The operation of one embodiment of a PFR would be represented by a liquid-collection chamber 920, a gas-contacting chamber 910 and liquid-contacting chamber 900. The liquid-contacting chamber 900 is supplied with liquid from a medium preparation and holding reservoir 916 by pumps, pipes, controllers, regulators and fittings 915, as necessary or desirable. In some embodiments, liquid is supplied in excess to the liquid-contacting chamber 900 such that the excess is collected in an over flow reservoir 955 by pumps, pipes, controllers, regulators and fittings 930. The gas-contacting chamber 910 is supplied with conditioned gas from the conditioned gas supply source 941 by pumps, pipes, controllers, regulators and fittings 940, as necessary or desirable. In some embodiments, the gas-contacting chamber gas is conditioned to have 95% relative humidity or more. In some embodiments, the gas is conditioned to have 90% relative humidity or more, 80% relative humidity or more, 70% relative humidity or more, 60% relative humidity or more, 50% relative humidity or more, or a relative humidity such that the porous flow of liquid through the gas-contacting chamber is not impeded by the relative humidity of the gas supplied to the gas-contacting chamber 910. The gas from the gas-contacting chamber 910 is removed to an exhaust gas handling system 936 for treatment if needed by the pumps, pipes, controllers, regulators and fittings 935, as necessary or desirable.

Liquid is collected from the PFR from the liquid-collection chamber 920 through pumps, pipes, controllers, regulators and fittings 946, as desirable or necessary, to a reactor effluent reservoir 951. In some embodiments additional liquids such as antimicrobials or sterilants such as bleach may be added to the liquid-collection chamber 920 from the optional reservoir 950 through pumps, pipes, controllers, regulators and fittings 945, as necessary or desirable. The liquid in the reactor effluent reservoir 951 may optionally be cleaned, separated from one another, and/or recycled back into the system (not shown). For this embodiment the process flow diagram items 901, 905, 925 and 926 would not be used.

The operation of another embodiment of a PFR using the process flow diagram of FIG. 30 would be represented by a liquid-collection chamber 900, a gas-contacting chamber 910 and liquid-contacting chamber 920. The liquid-contacting chamber 920 is supplied with liquid from a medium preparation and holding reservoir 950 by pumps, pipes, controllers, regulators and fittings 945, as necessary or desirable. In some embodiments liquid is supplied in excess to the liquid-contacting chamber 920 such that the excess is collected in an over flow reservoir 951 by pumps, pipes, controllers, regulators and fittings 946, as necessary or desirable. The gas-contacting chamber 910 is supplied with conditioned gas from the conditioned gas supply source 941 by pumps, pipes, controllers, regulators and fittings 940, as necessary or desirable. In some embodiments, the gas-contacting chamber gas is conditioned to have 95% relative humidity or more. In some embodiments the gas is conditioned to have 90% relative humidity or more, 80% relative humidity or more, 70% relative humidity or more, 60% relative humidity or more, 50% relative humidity or more, or a relative humidity such that the porous flow of liquid through the gas-contacting chamber is not impeded by the relative humidity of the gas supplied to the gas-contacting chamber 910. The gas from the gas-contacting chamber 910 is removed to an exhaust gas handling system 936 for treatment if needed by the pumps, pipes, controllers, regulators and fittings 935, as necessary or desirable.

Conditioned gas is supplied to the liquid-collection chamber 900 from a gas supply source 901 by pumps, pipes, controllers, regulators and fittings 905, as necessary or desirable. In some embodiments, the gas for the liquid-collection chamber 900 is conditioned to have a relative humidity of 10% or less. In some embodiments the gas is conditioned to have 15% relative humidity or less, 20% relative humidity or less, 30% relative humidity or less, 50% relative humidity, or less. In some embodiments, the gas supplied to the liquid-collection chamber 900 is conditioned to be 40° C. or more. In some embodiments the gas is conditioned to be 50° C. or more, 60° C. or more, 70° C. or more, 80° C. or more, 90° C. or more, 110° C. or more, or 120° C. or more. The evaporated liquid may then be removed from the liquid-collection chamber 900 to a collection chamber 926, which may be a condenser, by pumps, pipes, controllers, regulators and fittings 925, as necessary or desirable. The collected liquid (which may optionally be cleaned) may optionally be recycled back into the system (not shown). Liquid from the extraction reservoir 916 is supplied to the liquid-collection chamber 900 by pumps, pipes, controllers, regulators and fittings 915, as necessary or desirable, for the extraction of substances and residues left after evaporation in the liquid-collection chamber upon the evaporation of the liquid supplied by porous flow from the liquid-contacting chamber 920. The extraction liquid is removed from the liquid-collection chamber 900 to a product recovery unit 955 by pumps, pipes, controllers, regulators and fittings 930, as necessary or desirable.

In operation, the porous substrate of reactors such as those illustrated in FIGS. 1, 3, 13, 14, 16, 21, 22 and 29 are loaded with reaction facilitators appropriate for the desired process. Liquid is circulated into and out of the liquid-contacting chamber through ports in the PFR. The porous substrate wicks liquid out of the liquid-contacting chamber, through the gas-contacting chamber and into the liquid-collection chamber.

In some embodiments, the liquid flow rate through the liquid-contacting chamber is greater than the amount of liquid removed by the wicking of the liquid into the porous substrate(s). In some embodiments, the liquid supplied to the liquid-contacting chamber contains some or all of the necessary compounds to sustain the reactivity of one or more of the reaction facilitators in the gas-contacting chamber. In some embodiments, the liquid supplied to the liquid-contacting chamber contains some or all of the necessary compounds to sustain the reactivity of one or more of the reaction facilitators loaded on or in the porous substrate. In some embodiments, the liquid supplied to the liquid-contacting chamber contains one or more reactants. In some embodiments, the liquid supplied to the liquid-contacting chamber contains one or more reactants and some or all of the necessary compounds to sustain the reactivity of one or more of the reaction facilitators in the gas-contacting chamber, or loaded on or in the porous substrate.

Gas is circulated into and out of the gas-contacting region through ports in the PFR. Reactants in the gas stream interact with substances loaded on or in the porous substrate to produce product. In some embodiments, the substances are reaction facilitators. In some embodiments, the substances loaded on or in the porous substrate facilitate reactions between reactants in the gas stream and reactants in the liquid, which are introduced into the gas-contacting chamber through the wicking action of the porous substrate. Products partitioned into the gas phase may be removed from the gas-contacting region together with gas circulating out of the gas-contacting region. Products partitioned into the liquid phase may be delivered to the liquid-collection chamber also through the wicking action of the porous substrate. In some embodiments, product is recovered in the liquid-collection chamber with the aid of gas circulating into and out of the liquid-collection chamber through ports and/or with the aid of liquid circulating into and out of the liquid-collection chamber through the same or dedicated ports. The circulating gas may encourage evaporation of liquid from the porous substrate. Product in the gas phase may be swept out with the circulating gas. Any product in the liquid phase retained on the porous substrate may be solubilized in the circulating liquid and swept out by that liquid.

In some embodiments, for example in some upflow embodiments, the evaporation of liquid from the porous substrate in the liquid-collection chamber may sustain capillary flow, operating essentially as a reactor motor, driving the flow of liquid to allow the reaction to continue as long as there is, for example, sufficient liquid supplied to the liquid-contacting chamber, and sufficient liquid leaving the reactor from the porous substrate in the liquid-collection (evaporation) chamber. Examples of the use of this type of PER are provided in Examples 1 and 2. In other embodiments, for example, some other downflow embodiments, the removal of liquid from the porous substrate directly (i.e. without evaporation) in the liquid-collection chamber may also sustain capillary flow, operating essentially as a reactor motor, driving the flow of liquid to allow the reaction to continue as long as there is, for example, sufficient liquid supplied to the liquid-contacting chamber, and sufficient liquid leaving the reactor from the porous substrate in the liquid-collection chamber. Examples of the use of this type of PFR are provided in Examples 8 and 9.

In operation, upflow reactors such as those illustrated in FIG. 24, run similarly to those in FIG. 3. The liquid added through a port 231 flows from the liquid-contacting chamber 230 in the porous substrate through the gas-contacting region 220 into the liquid-collection region 210. A reaction facilitator(s) on and/or in the porous substrate 250 in the gas-contacting chamber 220 catalyzes the reaction of reactants in the gas phase to produce products. Flow of liquid through the three regions is enabled by wicking action/capillary action of the porous substrate. Continuous flow is enabled by removing the liquid from the porous substrate material 250 in the liquid-collection chamber 210, which in these embodiments is by the removal of the evaporated liquid from the liquid-collection chamber 210.

In some embodiments of running the reactor of FIG. 14 in the upflow mode, reactants may be found in the liquid. In some embodiments the reaction facilitator is light reactive such as a phototrophic microorganism. In such cases light is provided from an external source and is able to enter the gas-contacting chamber through the clear plates 280 and 281. The liquid in the liquid-contacting chamber enters the gas-contacting chamber by porous flow enabled by the porous substrate material. Gas is supplied to the gas-contacting chamber through a port 222 and is removed by a port 224 in the side plate 270. Reactants, carried by the gas stream, react with the reaction facilitators in or on the porous substrate to produce product. In some embodiments, wherein the liquid supplied to the liquid-contacting chamber also includes reactants, the gas stream reactants may also interact with liquid stream reactants introduced into or onto the porous substrate in the gas-contacting region by porous flow. The porous substrate 250, which now may be carrying product, enters the liquid-collection chamber 210. Product is recovered in the gas phase, if applicable, by circulation of gas in the liquid-collection chamber, which may facilitate the evaporation of liquid off the porous substrate. Product can also be recovered in the liquid phase, if applicable, by circulating liquid (e.g. by intermittently circulating liquid) in the liquid-collection chamber. Or, product may be recovered by removing the porous substrate from the reactor if the product is on and/or in the porous substrate or on and/or in the reaction facilitator. Porous flow is enabled by the porous flow/wicking action of the porous substrate material 250. Gas is supplied for the liquid-collection chamber of the PFR 200 through a port 201 and is removed by a port 202 in the side plate 270. Liquid is supplied to the liquid-collection chamber through the same or through dedicated ports.

In operation, reactors such as those illustrated in FIGS. 21 and 22, also run similarly to the reactors shown in FIGS. 3 and 14 when run in the upflow mode. Specifically, in some embodiments, liquid added through a port 580 flows from a first liquid reservoir 535 through the liquid-contacting chamber 530 where the porous substrate 550 removes a portion of the liquid to be transported by porous flow/wicking action through the gas-contacting region 520 into the liquid-collection chamber 510. The remaining liquid moves through the liquid-contacting chamber 530 to a second liquid reservoir 536 were it is removed through a port 586 to be recycled back to the first liquid reservoir. A reaction facilitator(s) on and/or in the porous substrate 550 in the gas-contacting region 520 catalyzes the reaction of reactants in the gas phase to produce products. In some embodiments, reactants may also be found in the liquid. In some embodiments the reaction facilitator is light reactive such as a phototrophic microorganism. In such cases light is provided from an external source and is able to enter the gas-contacting chamber 520 and illuminate at least one side of the porous substrate 550. Gas is supplied to the liquid-collection chamber 510 through a port 555 in a gas distribution tube 515. Gas leaves the liquid-collection chamber 510 and is collected in a gas collection tube 516 prior to leaving the PFR 500 through a port 570. The deposited solids on the porous substrate 550 in the liquid-collection chamber 510 are extracted by periodic circulation of an extraction liquid through the liquid-collection chamber 510. Liquid is introduced in to the gas distribution tube through a port 560 where it then flows into the gas-contacting chamber 510 before being collected in the gas collecting tube 516. In some embodiments the liquid may reside in the gas-contacting chamber 510 for some period of time before being emptied into the gas collecting tube 516 while in other embodiments the extraction may be a continuous flow through type process. After the predetermined extraction time has elapsed or the predetermined amount of extraction liquid has flowed through the system, the liquid is drained from the gas distribution tube 515 and gas collection tube 516 through ports 555 and 575 respectively. The gas-contacting chamber 510 may be maintained at an angle sufficient to drain liquid from the chamber into the gas collection tube 516. Gas flow to the liquid-collection chamber 510 is then turned back on to remove any access liquid and to reinitiate porous flow in the PFR 500. Any excess extraction liquid remaining in the gas distribution tube 515, liquid-collection chamber 510 and gas collection tube 516 is evaporated.

The reactor of FIGS. 17 and 18 can operate similarly to the reactors previously described, except that the liquid-collection region of the porous substrate can be separately removed and replaced (for example either with the original piece of porous substrate after removing product and/or other chemicals or with a new piece of porous substrate). An example of the use of this type of PFR is provided in Examples 2-4.

Reactors, such as those shown in FIG. 19, which include more than one gas-contacting zone, can be used to run multiple processes or multi-step processes. Similar to the operations previously described, liquid, optionally containing reactant(s) and/or nutrients, is added to the liquid-contacting chamber through a port. The porous substrate, in contact with liquid in the liquid-contacting region wicks liquid upward through the gas-contacting chambers and into the liquid-collection chamber. The porous substrate in the first gas-contacting chamber is loaded with one or more types of reaction facilitators. The porous substrate in the second gas-contacting chamber is also loaded with one or more types of reaction facilitators. The reaction facilitator(s) loaded on porous substrate in the first chamber may be the same, different, or partially the same as the reaction facilitator(s) loaded onto the porous substrate in the second gas-contacting chamber. A first gas, containing one or more types of reactants, flows into and out of the first gas-contacting chamber through ports in fluid communication with the first gas-contacting chamber. Another gas, which may be the same or different as the first gas, and containing one or more types of reactants, which may be the same, different, or partially the same as reactants in the first gas, flows into and out of the second gas-contacting chamber through ports in fluid communication with the second gas-contacting chamber. Substrates provided by the gas, and optionally liquid, react in the gas-contacting region and form products, which may be wicked by porous flow to the liquid-collection chamber, if the product is in the liquid phase. The gas, reactants, and reaction facilitators, are chosen to accomplish a desired reaction or reactions. In some embodiments, different processes occur in the first gas-contacting chamber and in the second gas-contacting chamber. In some embodiments, the process in the first gas-contacting chamber is the first step in a multi-step process and the process in the second gas-contacting chamber is the second step in a multi-step process. Thus, for example, the product or products produced in the first chamber flow into the second chamber and are the substrate or substrates (or some of the substrates) for the reaction in the second chamber. In some embodiments, one or the other of the processes in each chamber may include substances that negatively impact the other process. In some embodiments the flow of detrimental substances between the chambers is prevented or sufficiently alleviated such that the individual reactions in each chamber can still proceed at a desired rate. An example of the use of this type of PFR (although operated in downflow mode) is provided in Example 6.

Reaction conditions, including the liquid, any additions to the liquid such as nutrients, light, temperature, humidity, etc. may be chosen to maintain the viability of the reaction facilitators loaded onto the porous substrate for a desired time, and to meet at least the minimum needed reaction conditions. Liquid that is wicked into the liquid-collection region, is evaporated off the porous substrate. In some embodiments, gas flows into and out of the liquid-collection region to improve evaporation. In some embodiments, product or other substances enter the gas phase by evaporation and are removed from the chamber by flowing gas through the liquid-collection chamber. Alternatively, products or other substances may be dissolved into a liquid phase and removed from the liquid-collection chamber by flowing liquid into and out of the liquid-collection chamber through ports in the chamber.

Two-chamber reactors, such as those illustrated in FIGS. 24 and 25, also can operate as generally described with the liquid supplied in the liquid-contacting region 610. However, product or substances that are produced in and/or on the reaction facilitator, or are otherwise found on and/or in the porous substrate, may be harvested by removing the porous substrate from the reactor itself. In some embodiments, two-chamber reactors can be one-time use reactors—that is, used to run a desired process for a desired time period, or so long as the porous substrate material can permit (e.g. until saturated with product or other substances). In these cases, the porous flow substrate may be harvested along with the product and/or the reaction facilitator such as in Example 8 (which was run on a reactor according to FIG. 25 but in downflow mode) and Example 9 (which is run on a reactor according to FIGS. 1, 24 and/or 25 in either upflow or downflow mode).

One-chamber reactors, such as those illustrated in FIGS. 26 and 28 also can operate as generally described. However, product or substances that precipitate onto the porous flow substrate, or are otherwise found on or in the porous substrate are harvested by removing the porous substrate from the reactor itself. In some embodiments, one-chamber reactors can be one-time use reactors—that is, used to run a desired reaction or process for a desired time period, or so long as the porous substrate material can permit (e.g. until saturated with product or other substances).

Certain porous substrates, after having been harvested along with the product, may be converted into additional useful products. This conversion may take place before or after the original products has been separated from the porous substrate.

A number of embodiments of operation have been described. However a person of skill can readily appreciate from a review of this specification and figures that other embodiments are also possible, and thereby are also within scope of the invention. For example, a number of the reactor embodiments have been described as operating in upflow mode, however they may also operate in downflow mode or be reconfigured to operate in downflow mode such as by providing liquid to the what is the upflow liquid-collection region (now a downflow liquid-contacting region) and removing liquid at what is the upflow liquid-contacting region (now the downflow liquid-collection region).

V. Examples

Example 1. L-Sorbose Production

In this example, *Gluconobacter oxydans* ATCC621 catalyzed the partial oxidation of D-sorbitol to L-sorbose with the stoichiometric consumption of oxygen in a PFR similar to FIG. 3 run in upflow mode. A *G. oxydans* culture was grown at 30° C. and 200 rpm in growth medium to an $OD_{600}$ of 2.2, centrifuged at 4° C., 5,000 rpm, for 10 minutes. The 3 g wet cell pellet was resuspended in 7 ml SPP medium. The cells were then directly immobilized on the porous substrate 15×17.5 cm 3 MM CHR chromatography paper (Cat. 3030-153; Whatman, part of GE Healthcare) with a paint brush. The liquid-contacting chamber of the PFR was supplied with SPP medium daily. The gas-contacting chamber was continuously supplied with humidified air generated by sparging through water prior to being sent through the gas-contacting chamber. The liquid-collection chamber was continuously flushed with air. Table 1 shows the liquid volumes of each liquid addition, cumulative D-sorbitol added, and the results of the extraction.

TABLE 1

Results of D-sorbitol conversion to L-sorbose. Only L-sorbose was detected in the liquid collection chamber indicating 100% conversion by the *G. oxydans* in the PFR.

| | | | Extraction | | |
|---|---|---|---|---|---|
| Time (hr) | Medium (ml) | D-sorbitol (g) | D-sorbitol (g) | L-Sorbose (g) | Conversion (%) |
| 0 | 0 | 0 | | | |
| 15 | 4 | 0.12 | | | |
| 16.5 | 6 | 0.18 | | | |
| 18 | 7.5 | 0.225 | | | |
| 22.5 | 11 | 0.33 | | | |
| 24.5 | 12.5 | 0.375 | | | |
| 42 | 23 | 0.69 | | | |
| 47 | 26 | 0.78 | | | |
| 54 | 32 | 0.96 | | | |
| 73 | 41 | 1.23 | | | |
| Total 93 | 68 | 2.04 | 0 | 0.57 | 100 |

Example 2. Laurate Production

In this example, a strain of the cyanobacterium *Synechocystis* sp. PCC6803 capable of producing laurate was used to catalyze the production of laurate in a PFR similar to FIG. 17. The cells were harvested by centrifugation at 3000 rpm and 4° C. for 10 minutes. The cell pellet was re-suspended in BG11 medium and re-centrifuged with the same conditions for 10 minutes in a 50 ml conical tube. The pellet was resuspended 1:1 (w/v) in BG11 and vortexed until a homogeneous cell suspension was achieved (15 seconds). The cell suspension was immobilized on the porous substrate 3 MM CHR chromatography paper (Whatman, part of GE Healthcare) using a paint brush. BG11 medium was periodically added to the liquid-contacting region and the porous substrate in the headspace was periodically removed for extraction of products and a new piece of 3 MM CHR chromatography paper was put in its place.

TABLE 2

Cumulative laurate production in the PFR. Laurate was continuously produced for 6 days from $CO_2$ by the cyanobacteria in the PFR.

| Time (Days) | Laurate (mg) |
|---|---|
| 0.29 | 0.01 |
| 1.96 | 0.22 |
| 4.77 | 0.40 |
| 6.79 | 0.69 |

Example 3. Fructose and Glucose Production

In this example, a strain of the cyanobacterium *Synechococcus* sp. PCC 7942 capable of excreting fructose and glucose catalyzes the production of fructose and glucose in a PFR similar to FIG. 24 run in downflow mode. The fructose and glucose secreting *Synechococcus* sp. PCC7942 is grown in BG11 medium. The culture is centrifuged at 3000 rpm and 4° C. for 10 minutes. The initial cell pellet is resuspended in BG11 medium and re-centrifuged with the same conditions for 10 minutes in a 50 ml conical tube. The pellet is resuspended 1:1 (w/v) in BG11 and vortexed until a homogeneous cell suspension is achieved (15 seconds). The cell suspension is applied to the porous substrate 3 MM CHR chromatography paper (Whatman, part of GE Healthcare) using a paint brush. BG11 medium is continuously supplied to the liquid-contacting region to initiate porous flow and sustain porous flow.

Example 4. Sucrose Production

In this example, a strain of the cyanobacterium *Synechococcus* sp. PCC 7942 capable of excreting sucrose catalyzed the production of sucrose in a PFR similar to FIG. 21. The sucrose secreting *Synechococcus* sp. PCC7942 is grown in BG11 medium. The culture is centrifuged at 3000 rpm and 4° C. for 10 minutes. The initial cell pellet is resuspended in BG11 medium and re-centrifuged with the same conditions for 10 minutes in a 50 ml conical tube. The pellet is resuspended 1:1 (w/v) in BG11 and vortexed until a homogeneous cell suspension is achieved (15 seconds). The cell suspension is applied to the porous substrate 3 MM CHR chromatography paper (Whatman, part of GE Healthcare) using a paint brush. BG11 medium is continuously supplied to the liquid-contacting region to initiate porous flow and sustain porous flow.

Example 5. Synthesis Gas Fermentation (Carbon Monoxide Utilization)

In this example, an acetogenic ethanologen such as *Clostridium ljungdahlii* or another microorganism capable of utilizing any or all of $H_2$, CO and $CO_2$ such as a strain *Ralstonia eutropha* is immobilized in a way similar to the previous examples as the reaction facilitator in a PFR similar to that illustrated in FIG. 1. The organisms catalyze the conversion of gaseous $CO_x$ compounds to liquid products such as ethanol or butanol. The products transported to the liquid-collection chamber are collected along with the liquid transported from the liquid-contacting chamber through the porous substrate. Product is then recovered from the liquid. Additional products which may have been evaporated in the gas-contacting chamber are condensed from the gas exiting the gas-contacting chamber using a condenser.

Example 6. Ethanol Production

In this example, a strain of yeast such as *Saccharomyces cerevisiae* capable of fermenting sugars catalyzed the production of ethanol in a PFR similar to FIG. 24, operating in a downflow mode (This example can also be run in an upflow mode). The yeast was grown according to the respective protocols for producing biomass for the culture. The culture was centrifuged at 3000 rpm and 4° C. for 10 minutes. The initial cell pellet was re-suspended in fresh growth medium and re-centrifuged with the same conditions for 10 minutes in a 50 ml conical tube. The 1.94 g wet cell pellet was re-suspended in polyurethane dispersion formulation C1003 (Bayer) and vortexed until a homogeneous cell suspension was achieved (15 seconds). The cell suspension was applied to the porous substrate 2668 (Whatman, part of GE Healthcare) using an air brush (Badger model #150-2-F). Media containing 50 g/L of sucrose was supplied to the PFR at a rate of 3.42 ml/h. Table 3 shows the cumulative sucrose conversion to ethanol in the PFR, for which the sucrose is continuously converted to ethanol for six (6) days by the yeast in the PFR.

TABLE 3

| Time [h] | Sucrose [g] | Ethanol [g] |
| --- | --- | --- |
| 0.0 | 0.0 | 0.0 |
| 24.0 | 2.6 | 1.0 |
| 48.0 | 5.5 | 2.1 |
| 72.0 | 8.4 | 3.3 |
| 96.0 | 11.6 | 4.6 |
| 120.0 | 15.0 | 5.9 |
| 148.0 | 18.3 | 7.2 |

Example 7. Ethanol Production by Two Reaction Facilitators

In this example, a PFR similar to FIG. 19 run in downflow mode contains a phototrophic first reaction facilitator such as cyanobacterium *Synechococcus* sp. PCC 7942 capable of secreting sucrose for the production of sucrose, which is a substrate for a second reaction facilitator capable of producing ethanol from sucrose such as a yeast *Saccharomyces cerevisiae* capable of producing ethanol from sucrose. Both reaction facilitators are grown according to the respective protocols for producing biomass for each culture. The cultures are independently harvested to retrieve the wet cell pellet as described in the prior examples. The cell suspensions are then applied to the porous substrate such that the phototroph (or first product producer) is applied to the porous substrate region corresponding to the first gas-contacting chamber. The secondary producer is applied to the region of the porous substrate corresponding to the second gas-contacting chamber. Once the reactor is assembled, porous flow is initiated with the medium which supports the activity of both reaction facilitators. Both gas-contacting chambers are flushed with an anaerobic 1% $CO_2$ containing gas stream. In the first chamber sucrose is produced which is then carried to the second chamber by porous flow of the medium where it is converted to ethanol by the second organism. The ethanol is collected from the liquid in the liquid-collection chamber and the exhaust gas of the second gas-contacting chamber.

Example 8. Production of Products Contained within a Photosynthetic Reaction Facilitator In this example, an algae such as *Heterococcus coloradii*, capable of producing and accumulating an omega-3 containing oil, catalyzed the photosynthetic production of the omega-3 containing oil from $CO_2$ in a PFR similar to FIG. 25 operating in a downflow mode. The omega-3 containing oil accumulating strain *Heterococcus coloradii* was grown in BG11 medium at 5° C. The culture was centrifuged at 3000 rpm and 4° C. for 10 minutes. The initial cell pellet was re-suspended in BG11 medium and re-centrifuged with the same conditions for 10 minutes in a 50 ml conical tube. The pellet was resuspended 1:10 (w/v) in BG11 and vortexed until a homogeneous cell suspension was achieved (15 seconds). The cell suspension was applied to the porous substrate 3 MM CHR chromatography paper (Whatman, part of GE Healthcare), Bounty Basic paper towel, 2668 (Whatman, part of GE Healthcare), Viva paper towel or other porous flow substrate using a paint brush or squirt bottle. BG11 medium was continuously supplied to the liquid-contacting region while the reaction facilitator *Heterococcus coloradii* catalyzed the production of oil in the PFR incubated in light at approximately 5° C. for 60 days. The porous substrate along with the reaction facilitator was dried by stopping the flow of media to the liquid-contacting chamber. After the porous substrate has dried the reaction facilitator and porous substrate are harvested together and the reaction product extracted.

TABLE 4

Accumulation of omega-3 containing oil in the reaction facilitator using a PFR. Oil was accumulated in the algae *Heterococcus coloradii* in the PFR over 60 days. Fat was analyzed by standard gas chromatography method AOAC 996.06.

| Porous Flow Substrate | Algae Weight $(gm^{-2})$ | Total Fat (%) | Omega-3 (% algae) |
| --- | --- | --- | --- |
| 2668 | 18.89 | 67.88 | 8.21 |
| Bounty Basic | 33.29 | 11.63 | 1.88 |

Example 9. Production of Products in a Reaction Facilitator

In this example, a methanotrophic bacteria such as *Methylococcus capsulatus* or *Methylomicrobium alkaliphilum* or another methanotrophic bacterium capable of producing and accumulating protein, catalyzes the methanotrophic production of protein containing biomass from natural gas or methane in a PFR similar to FIGS. 1, 24 and/or 25 running in a downflow mode. The protein accumulating strain is grown in medium typical for that strain. The culture is centrifuged at 5000 rpm and 4° C. for 10 minutes. The initial cell pellet is re-suspended in medium and re-centrifuged with the same conditions for 10 minutes in a 50 ml conical tube. The pellet is re-suspended 1:10 (w/v) in medium and vortexed until a homogeneous cell suspension is achieved (15 seconds). The cell suspension is applied to the porous substrate 3 MM CHR chromatography paper (Whatman, part of GE Healthcare), Bounty Basic paper towel, 2668 (Whatman, part of GE Healthcare), Viva paper towel or other porous flow substrate using a paint brush, squirt bottle or other acceptable application method. Medium is continuously supplied to the liquid-contacting region while the reaction facilitator catalyzes the production of biomass in the porous flow. The porous substrate along with the reaction facilitator is dried by stopping the flow of media to the liquid-contacting chamber. After the porous substrate has dried the reaction facilitator and porous substrate are harvested together and the reaction product extracted.

Example 10. Conversion of Porous Substrate to Ethanol and Single Cell Protein

In this example, 100 g of the extracted porous substrate and reaction facilitator from Example 8 is homogenized in 1 Liter of 0.05 M citrate buffer adjusted to pH 4.8, which also contains 1% w/v yeast extract and 2% w/v peptone. The resulting suspension is poured into a 4 L Erlenmeyer flask equipped with a water trap and sterilized by autoclaving at 121° C. for 60 minutes. After cooling to room temperature, a commercial cellulase formulation, e.g. DuPont's Accelerase or Novozymes Cellic CTec, is added at a concentration of 10-15 Filter Paper Units (FPU) per gram of cellulose. The suspension is then inoculated with a seed culture of *Saccharomyces cerevisiae* to achieve an initial cell density of approximately 0.5 OD (measured at 600 nm) and then incubated in an orbital shaker at 120 rpm at 30-35° C. for 72-120 hours. Upon completion of the fermentation, the ethanol is removed in a stripper column and the protein-rich cell material is recovered from the resulting stillage by centrifugation and then dried.

VI. Additional Embodiments

A number of embodiments have been described but a person of skill understands that still other embodiments are encompassed by this disclosure. For example, another embodiment includes providing multiple non-adjacent sheets of porous material in a single layer, rather than a single sheet of porous material, extending from the liquid-contacting region through the gas-contacting region to the liquid-collection region in one or more of the embodiments described above. In some permutations of this embodiment, there are multiple liquid-contacting regions outside the housing and the liquid-collection region is either inside or outside the housing. Alternatively, the liquid-contacting region can be divided into multiple wells or multiple liquid-contacting regions within the housing, each well or region including one of the strips of non-adjacent porous materials.

Non-limiting methods and devices within the scope of the disclosure can also be defined in accordance with the below embodiments.

1. A device for studying cells immobilized on a surface, comprising:
   a. An aluminum housing defining a channel connecting a first, second and third chamber, the chambers are vertically-oriented one above the other, and the first chamber is a liquid-contacting chamber, the second chamber is a gas-contacting chamber, and the third chamber is an evaporation chamber;
   b. A set of four gaskets positioned within the channel, a first gasket is located below the liquid-contacting chamber, a second gasket is located between the liquid-contacting chamber and the gas-contacting chamber, a third gasket is located between the gas-contacting chamber and the evaporation chamber, and a fourth gasket is located above the evaporation chamber;
   c. A single sheet of porous material supported within the housing by the gaskets and extending through the channel from the liquid-contacting chamber through the gas-contacting chamber to the evaporation chamber, wherein cells are immobilized on or in the porous material in the gas-contacting region, wherein the porous material is capable of wicking liquid from the liquid-contacting chamber through the gas-contacting chamber to the evaporation chamber and the gaskets seal the chambers one from the other but still permit wicking of liquid by the porous material from the liquid-contacting region through the device to the evaporation region;
   d. A port in fluid connection with the liquid-contacting chamber for providing liquid to the liquid-contacting chamber;
   e. An entry port and an exit port in fluid connection with the gas-contacting chamber for flowing gas containing one or more reactants through the gas-contacting chamber;
   f. An entry port and an exit port in fluid connection with the evaporation chamber for flowing inert gas through the evaporation chamber;
   g. A condenser connected to the exit port of the gas-contacting chamber; and,
   h. A condenser connected to the exit port of the evaporation chamber; wherein the device is sized to fit on a desk-top.
2. A device according to embodiment 1, wherein the cells are *Clostridium ljungdohlii* cells.
3. A PFR, comprising:
   a. a porous material capable of wicking liquid;
   b. A housing having at least one chamber and enclosing at least a portion of the porous material;
   c. Three classes of regions: a liquid-contacting region, a gas-contacting region, and a liquid-collection region, wherein the liquid-collection region is optionally an evaporation region and wherein at least the gas-contacting region is located within the at least one chamber of the housing, and the porous material maintains fluid communication, directly or indirectly, between the liquid-contacting region, the gas-contacting region liquid-collection region; and,
   d. a port for flowing gas into and out of the gas-contacting region.
4. A PFR according to embodiment 3, wherein the porous material and each of the three classes of regions is within the housing.
5. A PFR according to embodiment 3 or 4, wherein the liquid-collection region is an evaporation region.
6. A PFR according to any of embodiments 3-5, wherein the porous material is one or more porous materials, and each of the porous materials extends from at least one liquid-contacting region through at least one gas-contacting region to at least one liquid-collection region.
7. A PFR according to embodiment 6, wherein each of the porous materials comprises one or more sheets of porous material which together maintain the fluid communication.
8. A PFR according to embodiment 3, wherein the housing has one chamber, the PFR has one liquid-contacting region, one gas-contacting region, and one evaporation region, the chamber defines the gas-contacting region, and the liquid-contacting region and liquid-collection region are outside the housing on either side of the gas-contacting region, the liquid-collection region is an evaporation region, and the porous material is one porous material comprising a first sheet of porous material and a second sheet of porous material, which overlap between the gas-contacting region and evaporation region.
9. A PFR according to embodiment 8, wherein the chamber defines the gas-contacting region and the liquid-contacting region, and the liquid-collection region is outside the housing.

10. A PFR according to embodiment 8 or 9, wherein the second sheet of porous material is releasably secured in the housing.
11. A PFR according to embodiment 4, wherein the housing comprises at least three chambers and each of the regions is located in its own chamber.
12. A PFR according to any of embodiments 3-11 wherein the housing further comprises a photic zone, and the photic zone permits the flow of light through the gas-contacting region.
13. A PFR according to any of embodiments 3-11, wherein at least the chamber defining the gas-contacting zone has a first and second transparent side on either end side of the chamber enabling the flow of light into the at least gas-contacting chamber.
14. A PFR according to any of embodiments 3-11, wherein the housing is configured to permit the flow of light into and out of the housing.
15. A PFR according to any of embodiments 3-14, wherein the gas-contacting region comprises one or more gas-contacting regions and the housing is configured to permit the flow of light into and out of at least one of the one or more gas-contacting regions.
16. A PFR according to any of embodiments 3-15, wherein the housing comprises a first side opposite a second side, wherein each of the first and second side have transparent portions.
17. A PFR according to embodiment 4, wherein the height of the PFR corresponding to the region of porous flow ranges from about 0.001 to 10 m, the width of the PFR ranges from about 0.001 to 10 m, and the depth of the PFR ranges from about 0.001 to 5 m.
18. A PFR similar to embodiment 4, wherein the height of the PFR corresponding to the region of porous flow ranges from about 5 to 10 m, the width of the PFR ranges from about 5 to 10 m, and the depth of the PFR ranges from about 1 to 10 m.
19. A PFR similar to embodiment 4, wherein the height of the PFR corresponding to the region of porous flow ranges from about 0.25 to 5 m, the width of the PFR ranges from about 5 to 10 m, and the depth of the PFR ranges from about 1 to 10 m.
20. A PFR similar to embodiment 4, wherein the height of the PFR corresponding to the region of porous flow ranges from about 0.01 to 1 m, the width of the PFR ranges from about 1 to 10 m, and the depth of the PFR ranges from about 0.5 to 1 m.
21. A PFR similar to embodiment 4, wherein the height of the PFR corresponding to the region of porous flow ranges from about 0.01 to 1 m, the width of the PFR ranges from about 0.2 to 5 m, and the depth of the PFR ranges from about 0.25 to 1 m.
22. A PFR similar to embodiment 4, wherein the height of the PFR corresponding to the region of porous flow ranges from about 0.001 to 0.1 m, the width of the PFR ranges from about 0.001 to 0.025 m, and the depth of the PFR ranges from about 0.001 to 0.01 m.
23. A PFR according to embodiment 18, wherein the liquid-collection region comprises a portion of porous material protruding from the housing.
24. A PFR according to embodiments 3 or 4, wherein the PFR comprises a single chamber and all of the regions are located within the single chamber.
25. A PFR according to any of embodiments 3-7 and 11-16 wherein the liquid-contacting region is at least one liquid-contacting region, the gas-contacting region is at least one gas-contacting region, and the liquid-collection region is at least one liquid-collection region.
26. A PFR according to embodiment 25, wherein the at least one liquid-contacting region is at least two liquid-contacting regions, and at least one of the at least two liquid-contacting regions is located outside the single chamber and at least one of the at least two liquid-contacting regions is located in the single chamber.
27. A PFR according to any of embodiments 3-7 and 11-16, wherein the at least one chamber is a first chamber and a second chamber.
28. A PFR according to any of embodiments 3-7 and 11-16, wherein the at least one chamber is a first chamber, a second chamber and a third chamber.
29. A PFR according to embodiment 3 or 4, wherein the chamber is more than one chamber vertically arranged one above the other, the liquid-contacting region is one liquid-contacting region, the liquid-collection region is one-liquid-collection region, the gas-contacting region is more than one gas-contacting region, and each region is in a different chamber, with the gas-contacting regions located between the liquid-collection region and the liquid-contacting region.
30. A PFR according to embodiment 3 or 4, wherein the housing is reusable and the porous substrate is single use.
31. A PFR according to any of embodiments 3-7 and 11-16, wherein the liquid-contacting region is one or more liquid-contacting regions, the gas-contacting region is one or more gas-contacting regions, and the liquid-collection region is one or more liquid-collection regions, and each chamber can include one class of region, or more than one class of region, provided that at least one chamber includes at least a gas-contacting region.
32. A PFR according to embodiment 31, wherein the chamber is four or more chambers, the liquid-contacting region is one or more liquid-contacting regions, the gas-contacting region is one or more gas-contacting regions and the liquid-collection region is one or more liquid-collection regions, and each chamber includes one class or more than one class of regions, provided that at least one chamber includes a gas-contacting chamber.
33. A PFR according to any of the proceeding embodiments, further comprising a reaction facilitator on or within at least a portion of the porous flow material.
34. A PFR according to embodiment 33, wherein the reaction facilitator is located on the portion of the porous flow material located in the gas-contacting region.
35. A three-chamber reactor for running multiphasic processes, comprising:
    a. A housing;
    b. An porous flow region at least partially supported within the housing, the porous flow region comprising alternating layers of porous material and support material starting and ending with support material, and comprising at least one porous material and at least two support materials, wherein the porous material is capable of wicking liquid, the support material includes integrated ribbing and gaskets, the ribbing defining channels for fluid flow, the gaskets defining seals when the reactor is assembled, wherein the support material includes a number of gaskets sufficient to define the boundaries of the three chambers, wherein the three chambers are a liquid-contacting chamber, a gas-containing chamber, and liquid-collection chamber;
c. At least one pair of ports in fluid communication with the liquid-contacting chamber enabling the flow of liquid into and out of the liquid-contacting chamber;
d. At least one pair of ports in fluid communication with the gas-containing chamber enabling the flow of gas into and out of the gas-containing chamber; and,
e. At least one pair of ports in fluid communication with the liquid-collection chamber allowing enabling the flow of gas or liquid or both into and out of the liquid-collection chamber.

36. A three-chamber reactor according to embodiment 35, wherein the housing and porous flow region are releasably secured together.

37. A three-chamber reactor according to embodiments 35 or 36, wherein the porous flow region is located entirely within the housing.

38. A three-chamber reactor according to any of embodiments 35-37, further comprising exterior supports to alleviate bowing of the housing.

39. A three-chamber reactor according to any of embodiments 35-38, wherein the three chambers are vertically aligned, the liquid-collection chamber is an evaporation chamber, and the gas-contacting chamber is located below the evaporation chamber and the liquid-contacting chamber is located below the gas-contacting chamber.

40. A three-chamber reactor according to any of embodiments 35-39, wherein the support material further comprises integrated spacers above the gaskets defining the liquid-collection chamber and below the gaskets defining the liquid-contacting chamber, or both.

41. A three-chamber reactor according to any of embodiments 35-40, wherein at least a portion of the porous material located in the gas-contacting region is coated with reaction facilitators.

42. A three-chamber reactor according to embodiment 41, wherein the reaction facilitators are chosen from microorganisms, catalysts, enzymes and combinations thereof.

43. A three-chamber reactor for running multiphasic processes requiring light, comprising:
a. A housing defining a first liquid-contacting chamber, a second gas-contacting chamber and a third liquid-collection chamber, wherein at least the gas-contacting chamber is configured to permit a flow of light through it sufficient to sustain a process requiring light;
b. A single porous material supported within the housing extending through the three chambers, wherein the porous material is capable of wicking liquid and is coated with reaction facilitator;
c. A pair of ports in fluid connection with the liquid-contacting chamber to permit a flow of liquid through the liquid-contacting chamber;
d. A pair of ports in fluid connection with the gas-contacting chamber to permit a flow of gas through the gas-contacting chamber; and,
e. A pair of ports in fluid connection with the liquid-collection chamber to permit a flow of gas, a flow of liquid, or both through the evaporation chamber.

44. A three-chamber reactor according to embodiment 43 comprising a second pair of ports in fluid connection with the liquid-collection chamber, wherein the liquid-collection chamber is an evaporation chamber and the first pair of ports permits a flow of gas through the evaporation chamber and the second pair of ports permits a flow of liquid through the evaporation chamber.

45. A three-chamber reactor according to embodiment 43 or 44, wherein each of the three chambers is configured to permit light to flow through the chamber.

46. A three-chamber reactor according to any of embodiments 43-45 wherein the reaction facilitator is a phototrophic microorganism.

47. A three-chamber reactor according to any of embodiments 43-46 wherein the housing is releasably fastened together.

48. A three-chamber reactor according to any of embodiments 43-47, wherein the maximum depth of the reactor is determined by the distance sufficient light can enter and sustain the light-requiring process, the maximum height of the reactor is determined by the distance liquid can be wicked through the porous material, and the maximum width of the reactor is determined by economics relating to the cost of materials for building and running the reactor.

49. A three-chamber reactor according to embodiment 43, wherein the height of the device corresponding to the region of porous flow ranges from about 0.001 to 10 m, the width of the device ranges from about 0.001 to 10 m, and the depth of the device ranges from about 0.001 to 5 m.

50. A three-chamber reactor similar to embodiment 49, wherein the height of the device corresponding to the region of porous flow ranges from about 5 to 10 m, the width of the device ranges from about 5 to 10 m, and the depth of the device ranges from about 1 to 10 m.

51. A three-chamber reactor similar to embodiment 49, wherein the height of the device corresponding to the region of porous flow ranges from about 0.25 to 5 m, the width of the device ranges from about 5 to 10 m, and the depth of the device ranges from about 1 to 10 m.

52. A three-chamber reactor similar to embodiment 49, wherein the height of the device corresponding to the region of porous flow ranges from about 0.01 to 1 m, the width of the device ranges from about 1 to 10 m, and the depth of the device ranges from about 0.5 to 1 m.

53. A three-chamber reactor similar to embodiment 49, wherein the height of the device corresponding to the region of porous flow ranges from about 0.01 to 1 m, the width of the device ranges from about 0.2 to 5 m, and the depth of the device ranges from about 0.25 to 1 m.

54. A three-chamber reactor similar to embodiment 49, wherein the height of the device corresponding to the region of porous flow ranges from about 0.001 to 0.1 m, the width of the device ranges from about 0.001 to 0.025 m, and the depth of the device ranges from about 0.001 to 0.01 m.

55. A three-chamber reactor according to embodiment 43, wherein the reactor is configured for operation in a downflow mode.

56. A three-chamber reactor according to embodiment 55, wherein each of the three chambers is configured for light to flow through the chamber.

57. A three-chamber reactor according to embodiments 55 or 56 wherein the reaction facilitator is a phototrophic microorganism.

58. A three-chamber reactor according to any of embodiments 43-57, wherein the gas-contacting chamber has a transparent front side and a transparent back side.
59. A one-chamber reactor for running multiphasic processes requiring light, comprising:
   a. A housing defining a chamber, wherein the chamber is configured to permit light to flow through it;
   b. A porous material extending through the chamber and outside the housing, wherein at least a portion of the porous material in the chamber is coated with at least one reaction facilitator; and,
   c. At least one pair of ports for flowing a gas, a liquid, or both through the chamber, wherein a liquid-contacting region and a gas-contacting region are co-located in the chamber, and an evaporation region comprises a portion of the porous material that extends outside of the housing.
60. A one-chamber reactor according to embodiment 59, wherein the porous substrate comprises two overlapping sheets of porous material.
61. A one-chamber reactor according to embodiment 60 wherein the sheets overlap within the edges of the housing defining the boundary between the chamber and the evaporation region.
62. A four-chamber reactor for running multiphasic processes requiring light, comprising:
   a. a liquid-contacting region, two gas-contacting regions, and a liquid-contacting region;
   b. A housing defining four chambers, wherein one or more of the chambers is configured for light transparency, each of the regions is located within a chamber and each chamber includes only a single type of region;
   c. A porous material extending through each of the chambers, wherein at least a portion of the porous material is coated with at least one reaction facilitator; and,
   d. At least four pairs of ports, wherein each chamber has at least one pair of ports in fluid communication with it.
63. A four-chamber reactor according to embodiment 62, at least one of the gas-contacting regions is located within the at least one chamber configured for light transparency.
64. A four-chamber reactor according to embodiments 62 or 63, wherein the at least a portion of the porous material coated with at least one reaction facilitator is the portion located in the gas-contacting regions.
65. A four-chamber reactor according to any of embodiments 62-64 wherein the chambers are vertically aligned and are configured for upflow operation, wherein the liquid-collection chamber is an evaporation chamber located above a first gas-contacting chamber, which is located above a second gas-contacting chamber, which is located above a liquid-contacting chamber.
66. A four-chamber reactor according to any of embodiments 62-64 wherein the chambers are vertically aligned and are configured for downflow operation, wherein the liquid-collection chamber is located below a first gas-contacting chamber, which is located below a second gas-contacting chamber, which is located below the liquid-contacting chamber.
67. A four-chamber reactor according to any of embodiments 62-64, wherein each of the four chambers is configured for light transparency, and at least a portion of the sections of porous materials located within the gas-contacting regions are coated with at least one reaction facilitator.
68. A four-chamber reactor according to any of embodiments 62-67, wherein the least one facilitator coating the section of porous material located in the first gas-contacting chamber and the at least one reaction facilitator coating the section of porous material in the second gas-contacting chamber may be the same, different or partially the same.
69. A multi-chamber reactor for running multiphasic process, comprising a housing containing one gas-contacting chamber, one or more evaporation chambers up to a total number of evaporation chambers and two or more liquid-contacting chambers up to a total number of liquid-contacting chambers, provided that the total number of liquid-contacting chambers is one more than the total number of evaporations chambers; hollow supports attached to the housing for supporting the one or more evaporation chambers in an elevated position above the base of the housing and for delivering and removing gas, liquid or both from the one or more evaporation chambers; ducting connecting the two- or more liquid-contacting chambers for delivering and removing liquid from the two or more liquid-contacting chambers; porous material extending from with the two or more liquid-contacting chambers to the one or more evaporation chambers, wherein the two or more liquid-contacting chambers are spaced apart sufficiently to prevent or alleviate cross-flow between the porous material extending from one liquid-contacting chamber and the porous material extending from another liquid-contacting chamber; and, a pair of ports for delivering and removing gas from the gas-contacting chamber.
70. A reactor according to embodiment 69, wherein the housing is configured to permit the flow of light through the gas-contacting chamber.
71. A reactor according to embodiment 69 or 70 wherein the porous material comprises sheets of porous material, wherein a sheet of porous material extends from within one liquid-contacting chamber to an evaporation chamber.
72. A reactor according to embodiment 70 or 71, wherein the porous material has a portion located in the gas-contacting chamber, and the porous material is supported at an angle within the housing such that light entering the housing from the top illuminates the upward facing side of the porous material located in the gas-contacting chamber.
73. A reactor according to any of embodiments 69-72, wherein the one or more evaporation chambers is two or more, three or more, four or more, five or more, six or more seven or more, eight or more, nine or more, ten or more, twenty-five or more, fifty or more, seventy-five or more, or 100 or more evaporation chambers, and the two or more liquid-contacting chambers is three or more, four or more, five or more, six or more, seven or more, ten or more, eleven or more, twenty-six or more, fifty-one or more, seventy-six or more, or 101 or more liquid-contacting chambers.
74. A multi-chamber reactor for running multiphasic processes, comprising:
   a. At least one evaporation region, at least one liquid-contacting region and one gas-contacting region;

b. A chamber for each of the at least one evaporation regions, and a chamber within which the at least one liquid-contacting region and the one gas-contacting region are co-located;
c. A housing containing the chambers;
d. hollow support structures connected to the housing for holding each of the evaporation chambers in an elevated position above the base of the housing;
e. a pair of ports for delivering and removing liquid into and out of the liquid-contacting region;
f. a pair of ports for delivering and removing gas into and out of the gas-contacting region; and,
g. porous material coated with at least one reaction facilitator extending from within the liquid-contacting region through the gas-contacting region into the evaporation chamber.

75. A multi-chamber reactor according to embodiment 74 wherein the housing is configured to permit the flow of light through the gas-contacting region.

76. A multi-chamber reactor according to embodiment 74 or 75, wherein the at least one liquid-contacting region is at least two liquid-contacting regions.

77. A multi-chamber reactor according to embodiment 76 wherein the porous material extending from one liquid-contacting region is coated with the same, some of the same, or different reaction facilitators as the porous material extending from another liquid-contacting region.

78. A multi-chamber reactor according to any of embodiments 74-76, wherein the porous material comprises a total number of sheets of porous material, and the at least one evaporation chamber comprises a total number of evaporation chambers and the total number of sheets of porous material is the same as the total number of evaporation chambers, and further wherein each sheet of porous material is supported in vertical orientation by one of the evaporation chambers.

79. A multi-chamber reactor according to embodiments 74-77, wherein the one or more evaporation chambers is two or more, three or more, four or more, five or more, six or more, seven or more, eight or more, nine or more, or ten or more, twenty-five or more, fifty or more, seventy-five or more, or one hundred or more evaporation chambers.

80. A reactor for running multiphasic processes, comprising:
a. A housing comprising at least one chamber and containing a liquid-contacting region, a gas-contacting region and a liquid-contacting region;
b. porous material capable of wicking liquid and at least partially coated with at least one reaction facilitator, the porous material provides fluid communication between the liquid-contacting region, gas-contacting region and evaporation region; and,
c. one or more ports in the housing for delivering gas, liquid or both into the housing, wherein the reactor is configured to support continuous porous flow from a first end of the porous material to a second, opposite end of the porous material for a desired time period as long as the porous material is in contact with liquid at its first end in the liquid-contacting region and the liquid is removed from the porous material at its second end in the liquid-collection region.

81. A reactor according to embodiment 80, wherein the reactor is configured to operate in a downflow mode.

82. A reactor according to embodiment 81, wherein the reactor is configured to operate in an upflow mode, and the liquid-collection region is an evaporation region.

83. A reactor according to embodiment 82 wherein the reactor is a one-chamber reactor.

84. A reactor according to embodiment 83, wherein the porous material is self-supporting within the housing.

85. A one-chamber reactor according to embodiment 84, wherein the porous material is a sheet of porous material formed into a cone shape.

86. A one-chamber reactor according to embodiment 85, wherein the porous material is more than one sheet of porous material, and each sheet is formed into a cone shape.

87. A PFR, comprising: porous material capable of wicking liquid and a housing configured to receive gas in at least one region of the housing; wherein, the porous material is at least partially coated with at least one reaction facilitator, the porous material is at least partially located within the housing, and the porous material is supported within the housing in a manner such that when the porous material comes in contact with liquid, the porous material wicks the liquid in the direction of the reaction facilitator and through the region of the housing configured to receive gas and the wicking of liquid is continuous as long as the porous material is in contact with liquid at one of its ends and the liquid is removed from the porous material at another of its ends.

88. A method for performing a gas-liquid phase process, comprising:
a. Contacting a porous material of a PFR with a first liquid optionally containing reactants, causing the porous material to wick the first liquid through the porous material;
b. Providing a first gas containing one or more reactants into a gas-contacting region of the PFR containing at least a portion of the porous material, wherein at least a portion of the portion of porous material in the gas-contacting region is coated with at least one reaction facilitator;
c. Allowing the reactants within the first gas to react with the reaction facilitator on or in the porous material and optionally the reactants in the liquid, if present, to form one or more products;
d. Removing the first liquid from a liquid-collection region to drive porous flow; and,
e. Removing at least one of the one or more products from the PFR, the porous flow material or both.

89. A method according to embodiment 88, wherein removing liquid comprises one of: if the PFR includes an evaporation region, maintaining conditions in an evaporation region of the PFR suitable for causing evaporation of the first liquid from at least a portion of the porous material resulting in continuous porous flow for at least a desired time period, wherein the evaporation region is located nearer the top of the reactor than the gas-contacting region; or if the PFR includes a liquid-collection region that is nearer the bottom of the PFR than the gas-contacting region, removing the first liquid directly as it flows out of the porous substrate in a liquid-collection region of the PFR resulting in continuous porous flow for at least a desired time period.

90. A method according to embodiment 88 or 89, wherein the gas-contacting region is maintained at a relative humidity such that porous flow of the first liquid through the gas-contacting region is not detrimentally impeded by the relative humidity of the first gas supplied to the gas-contacting region.

91. A method according to any of embodiments 89-90, wherein removing at least one of the one or more products comprises: providing a second liquid to a region of the porous material in or on which one or more products have crystallized to solubilize the product crystallized; collecting the second liquid after the one or more products have dissolved into the second liquid; and recovering the one or more products from the second liquid.

92. A method according to embodiment 91, wherein the second liquid is provided to the evaporation region of the PFR.

93. A method according to any of embodiments 88-92, wherein removing product comprises: providing a second gas to a region of the porous material containing one or more products under conditions suitable to cause evaporation of the first liquid and vaporization of at least one of the one or more products into the second gas; collecting the second gas containing product; and recovering the product from the second gas.

94. A method according to embodiment 93, wherein the second gas is provided into an evaporation region of the PFR.

95. A method according to any of embodiments 88-94, wherein the first liquid contains some or all of the compounds necessary to sustain reactivity of one or more of the reaction facilitators.

96. A method according to any of embodiments 88-95, wherein the reaction facilitator is light reactive.

97. A method according to embodiment 96, wherein the reaction facilitator is a phototropic microorganism.

98. A method according to any of embodiments 88-96 wherein the process results in L-sorbose production, laurate production, fructose and glucose production, sucrose production, or ethanol production, or involves synthesis gas fermentation.

99. A method according embodiment 88, wherein product is partitioned into a gas phase in a gas-contacting region of the PFR and removing the product comprises recovering product from the first gas.

100. A method according to embodiment 99 wherein the first gas circulates into and out of the PFR in the gas-contacting region, and product is recovered with the first gas when it circulates out of the PFR in the gas-contacting region.

101. A bioreactor for running multiphasic processes, wherein the bioreactor comprises a structure for supporting a porous substrate coated with a reaction facilitator; a liquid-contacting region; a gas-contacting region enclosed in a chamber including a pair of ports for circulating gas within the chamber; and, a liquid collecting region, and wherein the porous substrate extends from the liquid-contacting region through the gas-contacting region to the liquid-collection region and the liquid-collection region is configured to permit removal of liquid from the porous material to support continuous porous flow as long as the porous material is in contact with liquid in the liquid-contacting region.

102. A bioreactor according to embodiment 101, wherein the porous substrate has a top nearer the top of the bioreactor and a bottom nearer the bottom of the bioreactor and the bioreactor is configured to support a flow of liquid from the bottom to the top of the porous substrate.

103. A bioreactor according to embodiments 101 or 102, wherein the liquid collecting region is an evaporation region.

104. A bioreactor according to embodiment 101, wherein the porous substrate has a top nearer the top of the bioreactor and a bottom nearer the bottom of the bioreactor and the bioreactor is configured to support a flow of liquid from the top to the bottom of the porous substrate.

105. A method according to embodiment 89, wherein the reactor comprises a liquid-collection region that is nearer the bottom of the reactor than the gas-contacting region and the reactor is operated in a downflow mode.

106. A method according to embodiment 89, wherein the reactor comprises an evaporation region that is nearer the top of the reactor than the gas-contacting region and the reactor is operated in an upflow mode.

107. A method according to embodiment 88, wherein the first liquid is provided at a top side of the porous material nearer the top of the reactor, and removing at least one of the one or more products comprises removing at least one of the one or more products from the liquid after it flows out of the porous material.

108. A method according to embodiment 88, further comprising collecting the liquid as it flows out of the porous material, removing at least one of the one or more products from the liquid, and recycling the liquid back to the top side of the porous material.

109. A method according to embodiment 88, further comprising converting the porous material into additional products.

110. A method according to embodiment 109, wherein the porous substrate comprises cellulose.

111. A method according to embodiment 110, wherein the cellulose is converted to glucose.

112. A method according to embodiment 111, further comprising converting the glucose into a product chosen from lipids, proteins, carbohydrates, organic acids and alcohols.

113. A method according to embodiment 89 wherein the continuous porous flow is intermittent.

What is claimed is:

1. A method for performing a gas-liquid phase reaction process, comprising:
a. driving a continuous flow of liquid at least in part by gravity through a porous material for a desired time period by providing a first liquid at a first end of the porous material and removing the first liquid from a second end of the porous material, wherein the porous material includes a reaction facilitator coated on at least a portion of the porous material and the porous material is at least partially enclosed in a housing of a porous flow reactor, the housing including a chamber defining a first gas-contacting region through which the porous material extends, a chamber defining a liquid-contacting region above the first gas-contacting region and a chamber defining a liquid-collection region below the first gas-contacting region, and wherein the chambers defining the first gas-contacting region, the liquid-contacting region and the liquid-collection region are vertically-aligned and the chamber defining the first gas-contacting region is sandwiched between the chamber defining the liquid-contacting region and the chamber defining the liquid-collection region and the porous material provides fluid communication at least between the liquid contacting-region and the first gas-contacting region; and, b. circulating a first gas containing a first reactant into the first gas-contacting region of the porous flow reactor via a pair of ports in the housing;

c. contacting the first gas with the porous material; and d. reacting the first reactant and the reaction facilitator in the first gas contacting region to produce a product.

2. The method according to claim 1, wherein the porous material is entirely enclosed within the housing of the porous flow reactor.

3. The method according to claim 1, further comprising, recovering the product.

4. The method according to claim 3, wherein the product is recovered in the first liquid as the first liquid flows out of the porous material at the second end of the porous material.

5. The method according to claim 1, further comprising recycling the first liquid back into the porous flow reactor after the first liquid is removed from the second end of the porous material.

6. The method according to claim 1, wherein reacting the first reactant and the reaction facilitator comprises an aerobic reaction or an anaerobic reaction, and the method further comprises circulating a second gas comprising a second reactant into a second gas-contacting region of the porous flow reactor, wherein the aerobic reaction occurs in one of the first or second gas-contacting region and the anaerobic reaction occurs in the other of the first or second gas-contacting region.

7. The method according to claim 1, wherein the reaction facilitator is chosen from one or more methanotrophic bacteria and the product is chosen from an intracellular accumulated carbohydrate, lipid, protein, and polyhydroxy-alkanoate-type product, and combinations thereof.

8. The method according to claim 1, wherein the first reactant is chosen from natural gas, methane, and combinations thereof, the reaction facilitator is *Methylococcus capsulatus*, and the product is a single cell protein.

9. The method according to claim 1, wherein the first reactant is chosen from carbon dioxide, carbon monoxide, hydrogen, methane, hydrogen sulfide, one or more volatile organics, and combinations thereof.

10. The method according to claim 1, wherein the product is chosen from ethanol, butanol, acetic acid, butyric acid, one or more amino acids, one or more longer chain fatty acids, one or more alkenes, isoprene, and combinations thereof.

11. A downflow reactor for performing gas-liquid reactions, comprising:

a. a housing comprising a chamber defining a gas-contacting region of the reactor, a chamber defining a liquid-contacting region and a chamber defining a liquid-collection region;

b. a porous substrate extending through the gas-contacting region of the reactor, the porous substrate comprises a reaction facilitator in at least a portion of the gas-contacting region of the reactor;

c. a pair of ports in the housing configured to permit a gas comprising a reactant to circulate through the gas-contacting region of the reactor and to contact the porous substrate comprising the reaction facilitator in the gas-contacting region;

d. the liquid-contacting-region positioned above the gas-contacting region; and, e. the liquid-collection region positioned below the gas-contacting region, wherein the porous substrate provides liquid communication at least between the liquid-contacting region and the gas-contacting region, and further wherein, the reactor is configured to support a flow of liquid through the porous substrate driven at least in part by gravity for a desired time period provided liquid is removed from the porous substrate, and wherein the chambers defining the gas-contacting region, the liquid-contacting region and the liquid-collection region are vertically-aligned and the chamber defining the gas-contacting region is sandwiched between the chamber defining the liquid-contacting region and the chamber defining the liquid-collection region.

12. The reactor according to claim 11, wherein the reactor has a top and a bottom and the reactor is configured such that the liquid is collected in a portion of the liquid-collection region that is discontinuous from an end of the porous substrate closest to the bottom of the reactor.

13. The reactor according to claim 11, wherein the porous substrate is two or more porous substrates, each porous substrate extending through the gas-contacting region and providing liquid communication between the liquid-collection region and the liquid-contacting region via the gas-contacting region.

14. The reactor according to claim 11, wherein the reaction facilitator is chosen from one or more microorganisms, one or more catalysts, one or more enzymes, and combinations thereof.

15. The reactor according to claim 11, wherein the gas-contacting region is one or more gas-contacting regions, the liquid-contacting region is one or more liquid-contacting regions, and the liquid-collection region is one or more liquid-collection regions.

16. The reactor according to claim 11, wherein the chamber defining the liquid contacting region is a sealed enclosure.

17. The reactor according to claim 11, wherein the porous substrate provides liquid communication between the liquid contacting region and the liquid collection region and the chamber defining the liquid collection region is a sealed enclosure.

* * * * *